(12) United States Patent
Berme et al.

(10) Patent No.: US 11,712,162 B1
(45) Date of Patent: Aug. 1, 2023

(54) SYSTEM FOR TESTING AND/OR TRAINING THE VISION OF A USER

(71) Applicant: Bertec Corporation, Columbus, OH (US)

(72) Inventors: Necip Berme, Worthington, OH (US); Mohan Chandra Baro, Columbus, OH (US); Cameron Scott Hobson, Powell, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 17/751,531

(22) Filed: May 23, 2022

Related U.S. Application Data

(63) Continuation-in-part of application No. 17/347,503, filed on Jun. 14, 2021, now Pat. No. 11,337,606, which is a continuation-in-part of application No. 16/997,821, filed on Aug. 19, 2020, now Pat. No. 11,033,453, which is a continuation-in-part of application No. 16/940,260, filed on Jul. 27, 2020, now Pat. No. 10,945,599, which is a
(Continued)

(51) Int. Cl.
| | | |
|---|---|---|
| G02B 27/01 | (2006.01) | |
| G06T 7/73 | (2017.01) | |
| A61B 3/113 | (2006.01) | |
| A61B 3/00 | (2006.01) | |

(52) U.S. Cl.
CPC .............. *A61B 3/113* (2013.01); *A61B 3/005* (2013.01); *G02B 27/0172* (2013.01); *G06T 7/73* (2017.01); *G02B 2027/0138* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| | | | |
|---|---|---|---|
| 4,948,371 A | 8/1990 | Hall | |
| 5,919,150 A | 7/1999 | Zanakis | |
| (Continued) | | | |

OTHER PUBLICATIONS

Diaz-Chito et al. (A reduced feature set for driver head pose estimation, Applied Soft Computing, 2016) (Year: 2016).*
(Continued)

*Primary Examiner* — Kyle Zhai
(74) *Attorney, Agent, or Firm* — The Law Office of Patrick F. O'Reilly III, LLC

(57) ABSTRACT

A system for testing and/or training the vision of a user is disclosed herein. The system includes at least one camera, a visual display device having an output screen, and a data processing device operatively coupled to the at least one camera and the visual display device. In one embodiment, the data processing device is programmed to determine a head position, head velocity, and/or head speed of a user during a vision test or vision training routine from a plurality of images of the head of the user captured by the at least one camera. In another embodiment, the data processing device is programmed to determine, based upon an input signal received from a user input device, a contrast display setting for a screen background relative to at least one visual target, the contrast display setting enabling the user to gradually adapt to increasing levels of visual stimulation.

7 Claims, 37 Drawing Sheets

Related U.S. Application Data continuation-in-part of application No. 16/672,485, filed on Nov. 3, 2019, now Pat. No. 10,722,114, which is a continuation-in-part of application No. 16/277,659, filed on Feb. 15, 2019, now Pat. No. 10,463,250, said application No. 16/997,821 is a continuation-in-part of application No. 16/120,237, filed on Sep. 1, 2018, now abandoned, said application No. 16/277,659 is a continuation-in-part of application No. 16/022,061, filed on Jun. 28, 2018, now Pat. No. 10,264,964.

(60) Provisional application No. 62/526,140, filed on Jun. 28, 2017.

(56) References Cited

U.S. PATENT DOCUMENTS

| | | |
|---|---|---|
| 6,038,488 A | 3/2000 | Barnes et al. |
| 6,113,237 A | 9/2000 | Ober et al. |
| 6,152,564 A | 11/2000 | Ober et al. |
| 6,190,173 B1 | 2/2001 | Jenkins et al. |
| 6,295,878 B1 | 10/2001 | Berme |
| 6,331,115 B1 | 12/2001 | Jenkins et al. |
| 6,354,155 B1 | 3/2002 | Berme |
| 6,389,883 B1 | 5/2002 | Berme et al. |
| 6,774,885 B1 | 8/2004 | Even-Zohar |
| 6,936,016 B2 | 8/2005 | Berme et al. |
| 7,540,615 B2 | 6/2009 | Merzenich et al. |
| 8,181,541 B2 | 5/2012 | Berme |
| 8,315,822 B2 | 11/2012 | Berme et al. |
| 8,315,823 B2 | 11/2012 | Berme et al. |
| 8,342,685 B2 | 1/2013 | Yoo et al. |
| D689,388 S | 9/2013 | Berme |
| D689,389 S | 9/2013 | Berme |
| 8,543,540 B1 | 9/2013 | Wilson et al. |
| 8,544,347 B1 | 10/2013 | Berme |
| 8,643,669 B1 | 2/2014 | Wilson et al. |
| 8,646,910 B1 | 2/2014 | Schenkein |
| 8,700,569 B1 | 4/2014 | Wilson et al. |
| 8,704,855 B1 | 4/2014 | Berme et al. |
| 8,764,532 B1 | 7/2014 | Berme |
| 8,847,989 B1 | 9/2014 | Berme et al. |
| D715,669 S | 10/2014 | Berme |
| 8,902,249 B1 | 12/2014 | Wilson et al. |
| 8,915,149 B1 | 12/2014 | Berme |
| 9,032,817 B2 | 5/2015 | Berme et al. |
| 9,043,278 B1 | 5/2015 | Wilson et al. |
| 9,066,667 B1 | 6/2015 | Berme et al. |
| 9,081,436 B1 | 7/2015 | Berme et al. |
| 9,168,420 B1 | 10/2015 | Berme et al. |
| 9,173,596 B1 | 11/2015 | Berme et al. |
| 9,200,897 B1 | 12/2015 | Wilson et al. |
| 9,277,857 B1 | 3/2016 | Berme et al. |
| 9,289,680 B2 | 3/2016 | Yamazaki et al. |
| D755,067 S | 5/2016 | Berme et al. |
| 9,404,823 B1 | 8/2016 | Berme et al. |
| 9,414,784 B1 | 8/2016 | Berme et al. |
| 9,468,370 B1 | 10/2016 | Shearer |
| 9,480,918 B2 | 11/2016 | Hayashi et al. |
| 9,517,008 B1 | 12/2016 | Berme et al. |
| 9,526,443 B1 | 12/2016 | Berme et al. |
| 9,526,451 B1 | 12/2016 | Berme |
| 9,558,399 B1 | 1/2017 | Jeka et al. |
| 9,568,382 B1 | 2/2017 | Berme et al. |
| 9,622,686 B1 | 4/2017 | Berme et al. |
| 9,763,604 B1 | 9/2017 | Berme et al. |
| 9,770,203 B1 | 9/2017 | Berme et al. |
| 9,778,119 B2 | 10/2017 | Berme et al. |
| 9,814,430 B1 | 11/2017 | Berme et al. |
| 9,829,311 B1 | 11/2017 | Wilson et al. |
| 9,854,997 B1 | 1/2018 | Berme et al. |
| 9,911,348 B2 | 3/2018 | Merzenich et al. |
| 9,916,011 B1 | 3/2018 | Berme et al. |
| 9,927,312 B1 | 3/2018 | Berme et al. |
| 10,010,248 B1 | 7/2018 | Shearer |
| 10,010,286 B1 | 7/2018 | Berme et al. |
| 10,085,676 B1 | 10/2018 | Berme et al. |
| 10,117,602 B1 | 11/2018 | Berme et al. |
| 10,126,186 B2 | 11/2018 | Berme et al. |
| 10,216,262 B1 | 2/2019 | Berme et al. |
| 10,231,662 B1 | 3/2019 | Berme et al. |
| 10,264,964 B1 | 4/2019 | Berme et al. |
| 10,331,324 B1 | 6/2019 | Wilson et al. |
| 10,342,473 B1 | 7/2019 | Berme et al. |
| 10,390,736 B1 | 8/2019 | Berme et al. |
| 10,413,230 B1 | 9/2019 | Berme et al. |
| 10,463,250 B1 | 11/2019 | Berme et al. |
| 10,527,508 B2 | 1/2020 | Berme et al. |
| 10,555,688 B1 | 2/2020 | Berme et al. |
| 10,646,153 B1 | 5/2020 | Berme et al. |
| 10,722,114 B1 | 7/2020 | Berme et al. |
| 10,736,545 B1 | 8/2020 | Berme et al. |
| 10,765,936 B2 | 9/2020 | Berme et al. |
| 10,803,990 B1 | 10/2020 | Wilson et al. |
| 10,853,970 B1 | 12/2020 | Akbas et al. |
| 10,856,796 B1 | 12/2020 | Berme et al. |
| 10,860,843 B1 | 12/2020 | Berme et al. |
| 10,945,599 B1 | 3/2021 | Berme et al. |
| 10,966,606 B1 | 4/2021 | Berme |
| 11,033,453 B1 | 6/2021 | Berme et al. |
| 11,052,288 B1 | 7/2021 | Berme et al. |
| 11,054,325 B2 | 7/2021 | Berme et al. |
| 11,074,711 B1 | 7/2021 | Akbas et al. |
| 11,097,154 B1 | 8/2021 | Berme et al. |
| 11,158,422 B1 | 10/2021 | Wilson et al. |
| 11,182,924 B1 | 11/2021 | Akbas et al. |
| 11,262,231 B1 | 3/2022 | Berme et al. |
| 11,262,258 B2 | 3/2022 | Berme et al. |
| 11,301,045 B1 | 4/2022 | Berme et al. |
| 11,311,209 B1 | 4/2022 | Berme et al. |
| 11,321,868 B1 | 5/2022 | Akbas et al. |
| 11,337,606 B1 | 5/2022 | Berme et al. |
| 11,348,279 B1 | 5/2022 | Akbas et al. |
| 2002/0034717 A1 | 3/2002 | Jenkins et al. |
| 2003/0216656 A1 | 11/2003 | Berme et al. |
| 2003/0235332 A1* | 12/2003 | Moustafa ............ G06V 10/242 382/157 |
| 2004/0127337 A1 | 7/2004 | Nashner |
| 2005/0153267 A1 | 7/2005 | Goldman et al. |
| 2005/0187023 A1 | 8/2005 | Miyamoto et al. |
| 2006/0003298 A1 | 1/2006 | Greenshpan et al. |
| 2007/0075985 A1 | 4/2007 | Niida |
| 2007/0166675 A1 | 7/2007 | Atkins et al. |
| 2007/0218439 A1 | 9/2007 | Delahunt et al. |
| 2007/0218440 A1 | 9/2007 | Delahunt et al. |
| 2008/0084427 A1 | 4/2008 | Delahunt et al. |
| 2008/0228110 A1 | 9/2008 | Berme |
| 2008/0261696 A1 | 10/2008 | Yamazaki et al. |
| 2010/0149073 A1 | 6/2010 | Chaum et al. |
| 2010/0248825 A1 | 9/2010 | Toyoda |
| 2011/0027766 A1 | 2/2011 | Yoo et al. |
| 2011/0077088 A1 | 3/2011 | Hayashi et al. |
| 2011/0277562 A1 | 11/2011 | Berme |
| 2012/0058823 A1 | 3/2012 | Minato et al. |
| 2012/0154744 A1 | 6/2012 | Erickson et al. |
| 2012/0154745 A1 | 6/2012 | Yoo et al. |
| 2012/0238831 A1 | 9/2012 | Benford |
| 2012/0266648 A1 | 10/2012 | Berme et al. |
| 2012/0271565 A1 | 10/2012 | Berme et al. |
| 2013/0046206 A1 | 2/2013 | Preminger |
| 2013/0101975 A1 | 4/2013 | Hardy et al. |
| 2013/0155376 A1 | 6/2013 | Huang et al. |
| 2013/0209977 A1 | 8/2013 | Lathan et al. |
| 2013/0219132 A1 | 8/2013 | Ito et al. |
| 2014/0017645 A1 | 1/2014 | Simpson |
| 2014/0081177 A1 | 3/2014 | Eguibar et al. |
| 2014/0335487 A1 | 11/2014 | Hinman et al. |
| 2014/0349724 A1 | 11/2014 | Seitz et al. |
| 2014/0356825 A1 | 12/2014 | Duffy |
| 2015/0031426 A1 | 1/2015 | Alloway |
| 2015/0096387 A1 | 4/2015 | Berme et al. |
| 2015/0187221 A1 | 7/2015 | Hinman et al. |
| 2015/0196232 A1 | 7/2015 | Mitsi et al. |

(56) References Cited

U.S. PATENT DOCUMENTS

| | | | |
|---|---|---|---|
| 2015/0273324 A1 | 10/2015 | Yamamoto | |
| 2015/0302754 A1 | 10/2015 | Kennerly et al. | |
| 2015/0335239 A1 | 11/2015 | MacFougall | |
| 2016/0080720 A1 | 3/2016 | Fullam | |
| 2016/0155353 A1 | 6/2016 | Merzenich et al. | |
| 2016/0220869 A1 | 8/2016 | McBride | |
| 2016/0245711 A1 | 8/2016 | Berme et al. | |
| 2016/0287157 A1 | 10/2016 | Simpson | |
| 2016/0317914 A1 | 11/2016 | Okamoto et al. | |
| 2016/0334288 A1 | 11/2016 | Berme et al. | |
| 2016/0342206 A1 | 11/2016 | Shazly et al. | |
| 2017/0049316 A1 | 2/2017 | Donaldson | |
| 2017/0150907 A1 | 6/2017 | Duffy | |
| 2017/0224210 A1 | 8/2017 | Mori et al. | |
| 2017/0235426 A1 | 8/2017 | Peterson et al. | |
| 2017/0345183 A1* | 11/2017 | Chen | G06T 7/521 |
| 2018/0024015 A1 | 1/2018 | Berme et al. | |
| 2018/0286259 A1 | 10/2018 | Ni | |
| 2018/0286272 A1 | 10/2018 | McDermott et al. | |
| 2018/0336791 A1 | 11/2018 | Delis et al. | |
| 2019/0078951 A1 | 3/2019 | Berme et al. | |
| 2019/0150727 A1 | 5/2019 | Blaha et al. | |
| 2020/0111385 A1 | 4/2020 | Issa et al. | |
| 2020/0139229 A1 | 5/2020 | Berme et al. | |
| 2020/0408625 A1 | 12/2020 | Berme et al. | |
| 2021/0333163 A1 | 10/2021 | Berme et al. | |
| 2022/0178775 A1 | 6/2022 | Berme et al. | |

OTHER PUBLICATIONS

Vicente et al. (Driver Gaze Tracking and Eyes Off the Road Detection System, IEEE, Aug. 2015) (Year: 2015).*
Eye Tracker with Scene Camera, SR Research Website, Web page <http://www.sr-research.com/EL_II_scam.html>, 1 page, dated Apr. 22, 2012, retrieved from Internet Archive Wayback Machine <https://web.archive.org/web/20120422195146/http://www.sr-research.com/EL_II_scam.html> on Oct. 15, 2014.
Eye Gaze Tracking Under Natural Head Movements, Zhiwei Zhu and Qiang Ji, 2005 IEEE.
Efficient real-time algorithms for eye state and head pose tracking in Advanced Driver Support Systems, Riad L. Hammoud, Andrew Wilhelm, Phillip Malawey, and Gerald J. Witt, 2005, IEEE.
Combined Head and Eye Tracking System for Dynamic Testing of the Vestibular System, Robert S. Allison, Moshe Eizenman, and Bob S. K. Cheung, IEEE Transactions on Biomedical Engineering, vol. 41, No. 11, Nov. 1996.
Active Eye-Tracking System by Using Quad PTZ Cameras, Chao-Ning Chan, Shunichiro Oe, Chern-Sheng Lint, IEEE 2007.
A Cascaded Scheme for Eye Tracking and Head Movement Compensation, X. Xie, R. Sudhakar, H. Zhuang, Systems and Humans, vol. 28, No. 4, Jul. 1998.
Wii Fit Body Test; YouTube; Sep. 1, 2013; https://www.youtube.com/watch?v=oYc5E1EeG78 (Year: 2013).
Stern; "Maintenance of Response Readiness in Patients With Parkinson's Disease: Evidence From a Simple Reaction Lime Task"; 2005; http://www.columbia.edu/~jam144/pdf/StemMangels(2005).pdf (Year: 2005).
"Meyend Vision + Performance: Nathan Conley Senaptec Multiple Object Tracking Assessment"; Jun. 2, 2016; https://www.youtube.com/watch?v=gETKm9ZAOiw (Year: 2016).
First office action on the merits (Non-Final Rejection) in U.S. Appl. No. 16/120,237, dated Aug. 13, 2019.
Second office action on the merits (Final Rejection) in U.S. Appl. No. 16/120,237, dated Oct. 29, 2019.
Third office action on the merits (Non-Final Rejection) in U.S. Appl. No. 16/120,237, dated Feb. 10, 2020.
Fourth office action on the merits (Final Rejection) in U.S. Appl. No. 16/120,237, dated May 19, 2020.
First office action on the merits (Non-Final Rejection) in U.S. Appl. No. 16/997,821, dated Nov. 16, 2020.
Notice of Allowance in U.S. Appl. No. 16/997,821, dated Feb. 19, 2021.
First office action on the merits (Non-Final Rejection) in U.S. Appl. No. 17/347,503, dated Aug. 20, 2021.
Notice of Allowance in U.S. Appl. No. 17/347,503, dated Jan. 21, 2022.

* cited by examiner

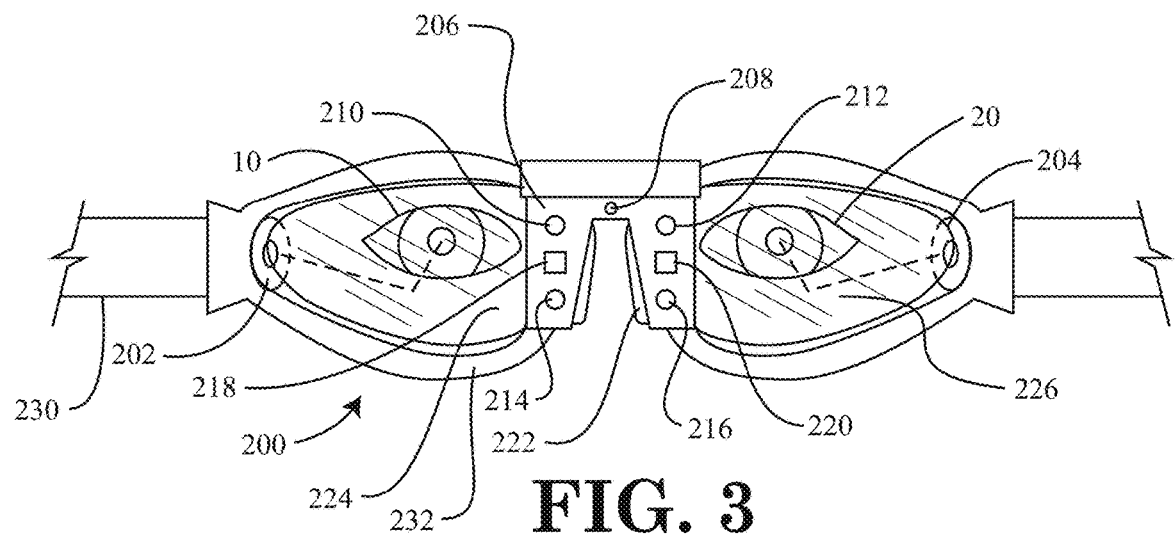
FIG. 3
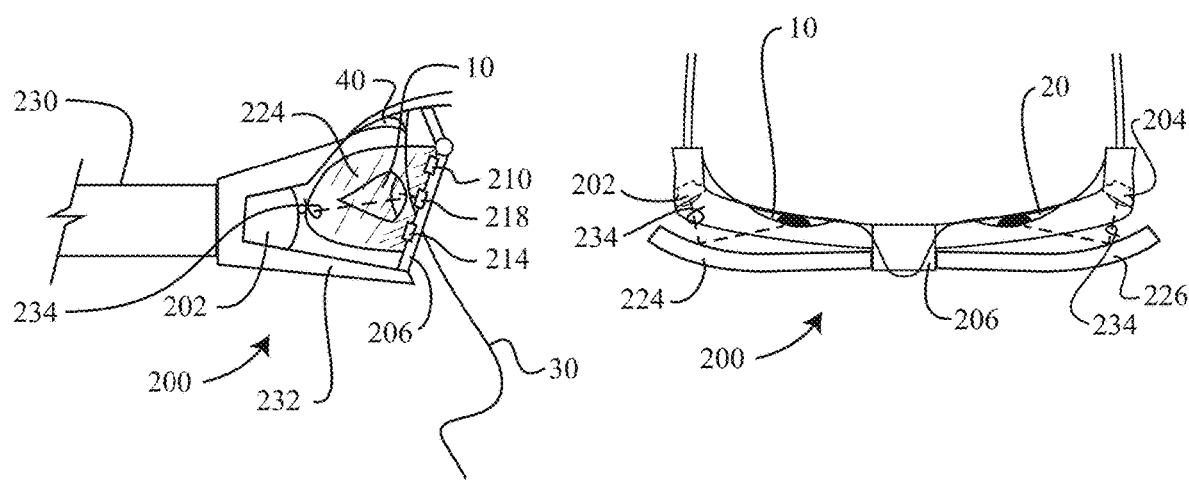
FIG. 4
FIG. 5

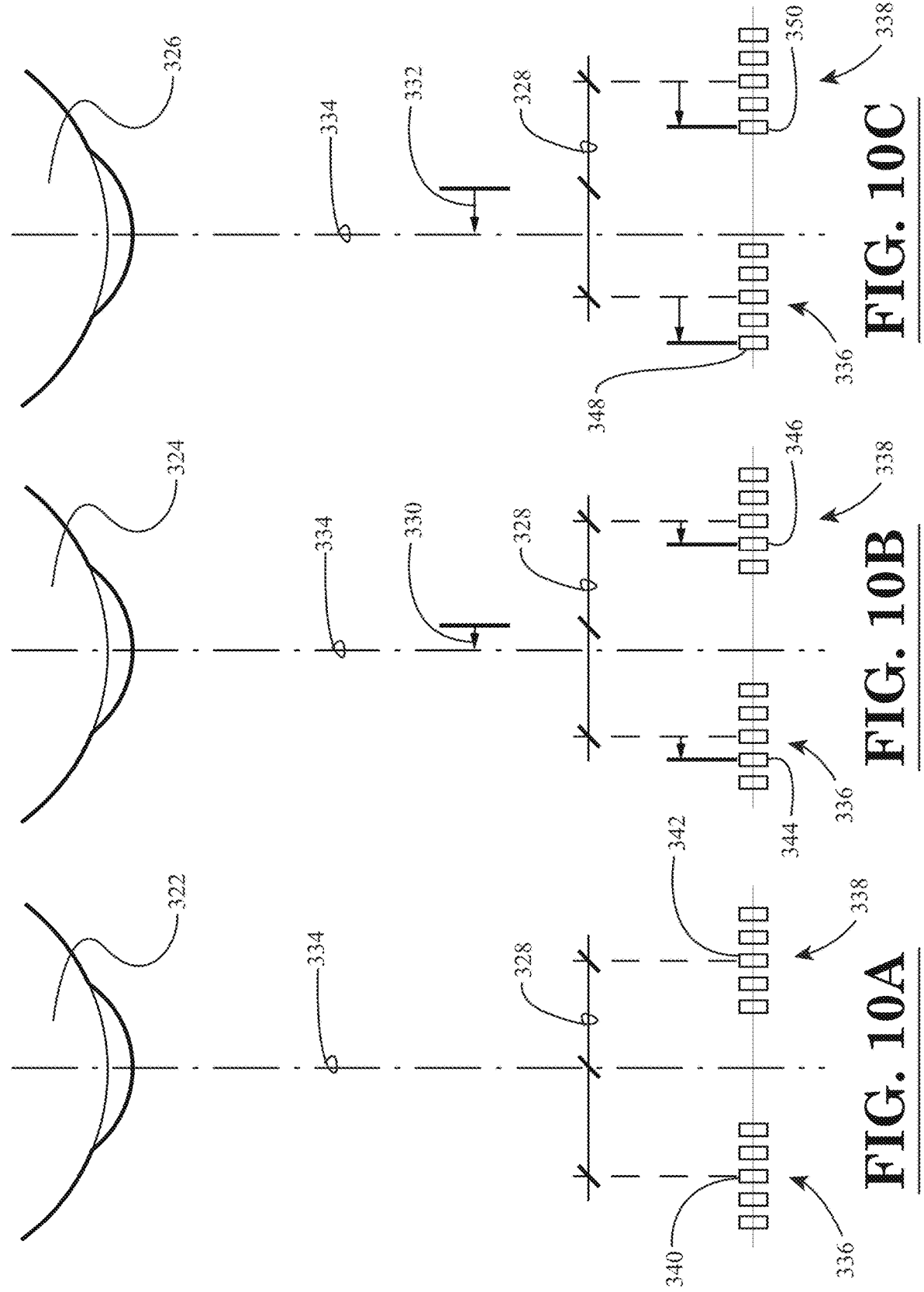

SYSTEM FOR TESTING AND/OR TRAINING THE VISION OF A USER

CROSS-REFERENCE TO RELATED APPLICATIONS

This is a continuation-in-part of U.S. Nonprovisional patent application Ser. No. 17/347,503 entitled "System For Testing And/Or Training The Vision Of A User", filed on Jun. 14, 2021; and U.S. application Ser. No. 17/347,503 is a continuation-in-part of U.S. Nonprovisional patent application Ser. No. 16/997,821 entitled "Neurocognitive Training System For Improving Visual Motor Responses", filed on Aug. 19, 2020; and U.S. application Ser. No. 16/997,821 is a continuation-in-part of U.S. Nonprovisional patent application Ser. No. 16/940,260 entitled "System And Method For Vision Testing And/Or Training", filed on Jul. 27, 2020; and U.S. application Ser. No. 16/940,260 is a continuation-in-part of U.S. Nonprovisional patent application Ser. No. 16/672,485 entitled "System And Method For Vision Testing And/Or Training", filed on Nov. 3, 2019, now U.S. Pat. No. 10,722,114; and U.S. application Ser. No. 16/672,485 is a continuation-in-part of U.S. Nonprovisional patent application Ser. No. 16/277,659 entitled "System And Method For Vision Testing", filed on Feb. 15, 2019, now U.S. Pat. No. 10,463,250; and U.S. application Ser. No. 16/277,659 is a continuation-in-part of U.S. Nonprovisional patent application Ser. No. 16/022,061 entitled "Eye Movement Measurement Device", filed on Jun. 28, 2018, now U.S. Pat. No. 10,264,964; and further claims the benefit of U.S. Provisional Patent Application No. 62/526,140, entitled "Eye Movement Measurement Device", filed on Jun. 28, 2017, the disclosure of each of which is hereby incorporated by reference as if set forth in their entirety herein.

U.S. Nonprovisional patent application Ser. No. 16/997,821 also is a continuation-in-part of U.S. Nonprovisional patent application Ser. No. 16/120,237 entitled "Neurocognitive Training System For Improving Visual Motor Responses", filed on Sep. 1, 2018, the disclosure of which is hereby incorporated by reference as if set forth in its entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a neurocognitive training system for improving visual motor responses. More particularly, the invention relates to a neurocognitive training system for improving visual motor responses of individuals having impairments and/or athletes seeking performance enhancement.

2. Background

The widely used conventional method for the measurement of eye movements is the scleral search coil (SSC) method. This method involves inserting contact lenses embedded with coils on the cornea and measuring the electromagnetic signals induced in the coils.

The SSC method provides very accurate measurements of both low-speed and high-speed eye movements in three dimensions. However, the method is not suitable for routine clinical testing because of its invasiveness and because of its relatively long preparation time.

Today for clinical testing, video recording and analysis of pupil movements is the method of choice. The method is non-invasive, but high-speed cameras are exponentially more expensive. Therefore, most cameras in the video-based clinical eye movement measurement systems are limited to 250 Hz.

An alternative method is using a non-video based infrared technology that can provide much higher speeds (approximately 2,000 Hz or more). However, these systems also have limitations. For example, there is electronic drift and measuring eye movements in complete darkness is difficult and not as accurate.

What is needed, therefore, is a non-invasive eye movement measurement device that is capable of accurately measuring of both low-speed and high-speed eye movements in a clinical setting. Moreover, an eye movement measurement device is needed that enables both low-speed and high-speed eye movements to be accurately measured without requiring a long preparation time. Furthermore, a need exists for an eye movement measurement device that utilizes hybrid technology so as to minimize the limitations associated with conventional devices relying upon a single type of measurement means.

The vestibulo-ocular reflex (VOR) involves the activation of the vestibular system of a person so as to cause eye movement. More particularly, the vestibulo-ocular reflex (VOR) operates so as to stabilize images on the retina during head movement. As a result of the vestibulo-ocular reflex (VOR), a head movement in one direction will produce eye movements in the opposite direction, thus preserving the images viewed by the person on the center of the visual field. Conventional tests are known for assessing the vestibulo-ocular reflex (VOR) of subjects, but these tests have numerous limitations and drawbacks, such as not being readily customizable for particular subjects, which can affect the accuracy and reliability of these tests.

What is needed, therefore, is a system for testing and/or training the vision of a subject that implements a customizable and accurate protocol for testing and/or training the vestibulo-ocular reflex (VOR) and/or visual motor performance of a subject. In addition, a method for testing the vision of a subject is needed that accurately tests the vestibulo-ocular reflex (VOR) and/or visual motor performance of a subject by utilizing a test that is customized for the particular subject being tested. Also, a system for testing and/or training the vision of a subject that enables subjects to be tested and trained more accurately in a shorter period of time is needed.

Further, many individuals experience concussions in the course of their lives. For example, athletes often sustain concussions while playing a particular sport, such as football or soccer. Frequently, one of the main consequences of a concussion is the impairment of vestibular function. Impairments in vestibular function are known to adversely affect dynamic visual acuity, and to cause blurred vision and poor visual focus when the concussed individual displaces his or her head. Visual motor exercises have been demonstrated to improve impairments in individuals with vestibular dysfunction, but to realize such an improvement, the concussed individual must perform the exercises in a regimented manner on a regular and frequent basis.

In addition, many athletes are seeking performance enhancement of their visual-motor system. Unlike concussed individuals, these individuals have full function of all motor control tasks and they are looking to improve their athletic performance by training their visual-motor system to perform faster and react more quickly during competition.

What is needed, therefore, is a neurocognitive training system for improving the visual motor performance of concussed individuals. Moreover, a neurocognitive training system is needed for enhancing the visual motor performance of athletes so that the athletes' visual motor system performs faster and reacts more quickly during athletic competition. Furthermore, a need exists for a neurocognitive training system as part of the rehabilitation regime for an orthopedic and/or neurological injury.

BRIEF SUMMARY OF EMBODIMENTS OF THE INVENTION

Accordingly, the present invention is directed to a system for testing and/or training the vision of a subject that substantially obviates one or more problems resulting from the limitations and deficiencies of the related art.

In accordance with one or more embodiments of the present invention, there is provided a system for testing and/or training the vision of a user. The system includes a system for testing and/or training the vision of a user. The system includes at least one camera, the at least one camera configured to capture a plurality of images of a head of a user during a vision test or vision training routine; a visual display device having an output screen, the visual display device configured to display one or more visual objects on the output screen so that the one or more visual objects are visible to the user; and a data processing device, the data processing device operatively coupled to the at least one camera and the visual display device. The data processing device is programmed to: (i) generate and display one or more configurations of a visual object on the output screen of the visual display device during the vision test or vision training routine; (ii) determine a head position, head velocity, and/or head speed of the user during the vision test or vision training routine from the plurality of images of the head of the user captured by the at least one camera; and (iii) determine whether or not the user correctly identifies the one or more configurations of the visual object displayed on the output screen of the visual display device.

In a further embodiment of the present invention, the data processing device is further programmed to determine the head position, the head velocity, and/or the head speed of the user from the plurality of images of the head of the user captured by the at least one camera by performing the following additional steps: (iv) extracting features from the plurality of images of the head of the user for providing inputs to a trained neural network; (v) determining one or more head poses and/or head movements of the user using the output of the trained neural network; and (vi) determining the head position, the head velocity, and/or the head speed of the user from the one or more head poses and/or head movements of the user.

In yet a further embodiment, the output of the trained neural network comprises a plurality of keypoints for facial features of the user; and the data processing device is further programmed to determine the one or more head poses and/or head movements of the user from the plurality of keypoints for the facial features of the user.

In still a further embodiment, the data processing device is further programmed to estimate a gaze direction of the user using at least some of the plurality of keypoints for the facial features of the user outputted by the trained neural network.

In yet a further embodiment, the system further comprises a user input device, the user input device configured to output an input signal in response to a manipulation of the user input device by a system user, the user input device being operatively coupled to the data processing device; and the determination of whether or not the user correctly identifies the one or more configurations of the visual object is based upon the input signal from the user input device.

In still a further embodiment, the user input device comprises at least one of: (i) a mouse, (ii) a keyboard, (iii) a clicking device, (iv) a selection device with a plurality of buttons corresponding to different configurations of the visual object, (v) a voice recognition device, and (vi) a joystick.

In yet a further embodiment, the user input device comprises a voice recognition device configured to capture verbal responses of the user regarding the one or more configurations of the visual object that are identified by the user so as to obviate a need for a clinician that records the verbal responses of the user.

In still a further embodiment, the visual object displayed on the output screen of the visual display device comprises an optotype, the optotype selected from the group consisting of: (i) a Tumbling E, (ii) a Landolt C, (iii) a house, (iv) a heart, (v) a circle, (vi) a square, (vii) a letter of a recognized alphabet, and (viii) any other identifiable symbol.

In accordance with one or more other embodiments of the present invention, there is provided a system for testing and/or training the vision of a user. The system includes a user input device, the user input device configured to output an input signal based upon an input response by the user; a visual display device having an output screen, the visual display device configured to display one or more screen images on the output screen so that the one or more screen images are visible to the user; and a data processing device, the data processing device operatively coupled to the user input device and the visual display device. The data processing device being programmed to: (i) generate and display at least one visual target and a screen background on the output screen of the visual display device, the at least one visual target being superimposed on the screen background; (ii) receive an input signal from the user input device based upon an input response by the user; and (iii) determine, based upon the input signal received from the user input device, a contrast display setting for the screen background relative to the at least one visual target, the contrast display setting enabling the user to gradually adapt to increasing levels of visual stimulation.

In a further embodiment of the present invention, the data processing device is further programmed to: (iv) generate a sliding scale and/or contrast value input box on the output screen of the visual display device for allowing the user to input a value for the contrast display setting for the screen background.

In yet a further embodiment, the data processing device is further programmed to: (iv) generate one or more input screen elements for allowing the user to upload a custom video background that is able to be used as the screen background displayed on the output screen of the visual display device; and (v) determine, based upon the input signal received from the user input device, the contrast display setting for the custom video background relative to the at least one visual target.

In still a further embodiment, the user is disposed on a measurement assembly, and the measurement assembly includes a top surface for receiving the body of the system user; and at least one measurement device, the at least one measurement device configured to sense one or more measured quantities and output one or more measurement signals that are generated based upon the user's contact with the top surface of the measurement assembly. In this further embodiment, the at least one visual target generated and displayed on the output screen by the data processing device comprises a first visual target and a second visual target, and the data processing device is further programmed to: (iv) receive the one or more measurement signals that are generated based upon the user's contact with the surface of the measurement assembly and to compute one or more numerical values using the one or more measurement signals; (v) control the movement of at least one manipulatable visual element by using the one or more computed numerical values; (vi) determine whether the user moves the at least one manipulatable visual element in a first target sensitivity area of the first visual target; (vii) when it is determined that the user has moved the at least one manipulatable visual element in the first target sensitivity area of the first visual target, initiate a countdown of a first time clock for performance of an additional action by the user; (viii) when the countdown of the first time clock has reached zero, generate a visual indicator on the second visual target for indicating that the user is to displace the at least one manipulatable visual element to the second visual target; (ix) when the visual indicator is generated on the second visual target, initiate a second time clock for recording an amount of time it takes for the user to displace the at least one manipulatable visual element to the second visual target; (x) determine when the user has displaced the at least one manipulatable visual element in a second target sensitivity area of the second visual target; and (xi) once it has been determined that the user has displaced the at least one manipulatable visual element in the second target sensitivity area of the second visual target, stop the second time clock and record the amount of time it took for the user to displace the at least one manipulatable visual element to the second target sensitivity area of the second visual target.

In yet a further embodiment, the visual indicator that is generated on the second visual target by the data processing device comprises a pulsating ring that moves radially outward from the center of the second visual target.

In still a further embodiment, the user is disposed on a measurement assembly, and the measurement assembly includes a top surface for receiving the body of the system user; and at least one measurement device, the at least one measurement device configured to sense one or more measured quantities and output one or more measurement signals that are generated based upon the user's contact with the top surface of the measurement assembly. In this further embodiment, the screen background generated and displayed on the output screen of the visual display device by the data processing device comprises a tunnel video background with a simulated tunnel where the user is made to feel as if the simulated tunnel is moving toward or away from him or her so as to immerse the user, and the data processing device is further programmed to: (iv) receive the one or more measurement signals that are generated based upon the user's contact with the surface of the measurement assembly and to compute center of pressure values for the user using the one or more measurement signals; (v) displace a center point of the simulated tunnel in the tunnel video background based upon the computed center of pressure values for the user; (vi) generate and display the at least one visual target on the tunnel video background; and (vii) determine, based upon the input signal received from the user input device, whether the user performed a correct action with respect to the at least one visual target by selecting the at least one visual target while the simulated tunnel is being displaced based upon the computed center of pressure values for the user.

In yet a further embodiment, the user input device comprises at least one of: (i) a touchscreen user interface, (ii) a voice recognition device, (iii) one or more buttons, (iv) a keyboard, (v) a clicking device, (vi) a joystick, and (vii) a pointing device.

In still a further embodiment, the visual display device is a touchscreen visual display device with a touchscreen user interface, and the user input device comprises the touchscreen user interface.

In yet a further embodiment, the visual display device is a head-mounted visual display device, and the user input device comprises at least one of a voice recognition device and a touchpad.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 3 is a front view of an eye movement measurement device, according to a second embodiment of the invention;

FIG. 4 is a right side view of the eye movement measurement device of FIG. 3;

FIG. 5 is a top view of the eye movement measurement device of FIG. 3;

FIG. 10A is a schematic diagram depicting an eye that is centered with respect to two sets of non-video-based sensors;

FIG. 10B is a schematic diagram depicting an eye that is displaced to the left by a first distance relative to two sets of non-video-based sensors;

FIG. 10C is a schematic diagram depicting an eye that is displaced to the left by a second distance relative to two sets of non-video-based sensors, wherein the second distance of FIG. 10C is greater than the first distance of FIG. 10B;

Throughout the figures, the same parts are always denoted using the same reference characters so that, as a general rule, they will only be described once.

DETAILED DESCRIPTION OF EMBODIMENTS OF THE INVENTION

Figure 1:
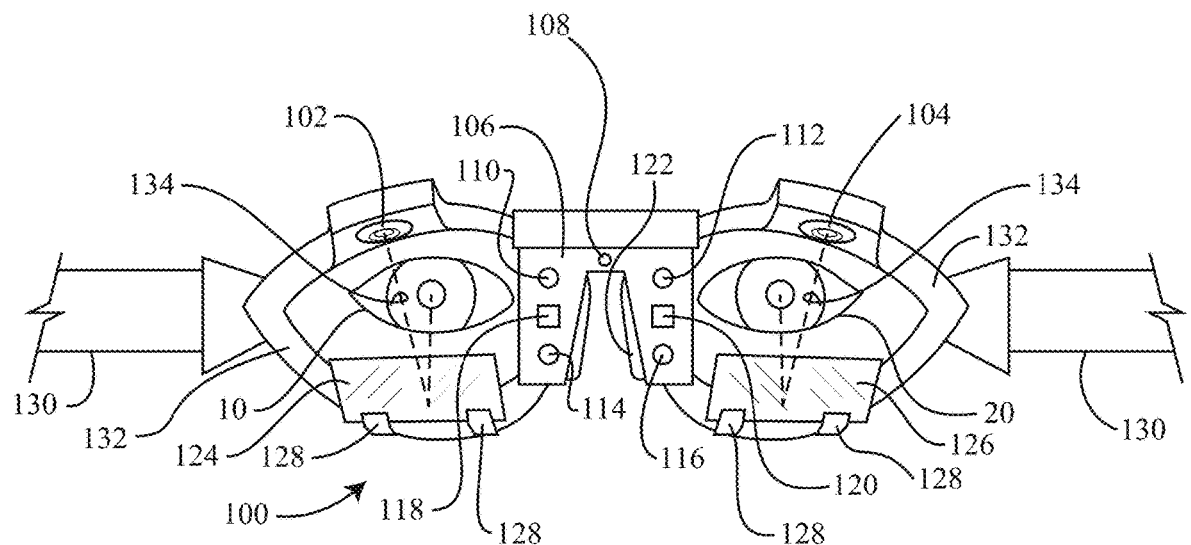
FIG. 1 is a front view of an eye movement measurement device, according to a first embodiment of the invention.
Figure 2:
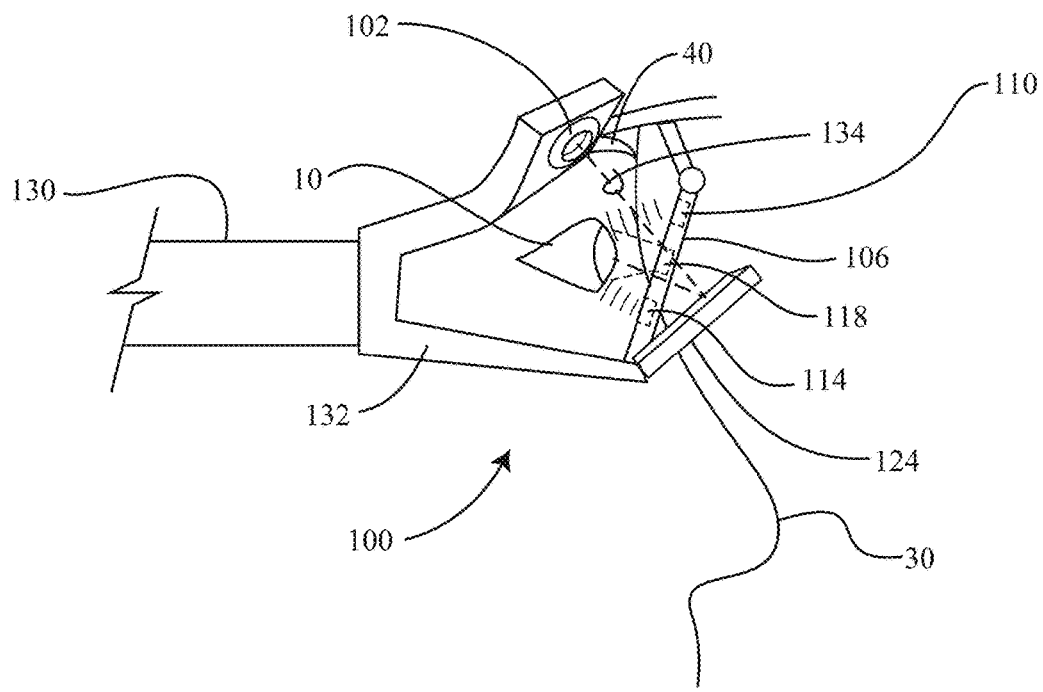
FIG. 2 is a right side view of the eye movement measurement device of FIG. 1.
Figure 7:
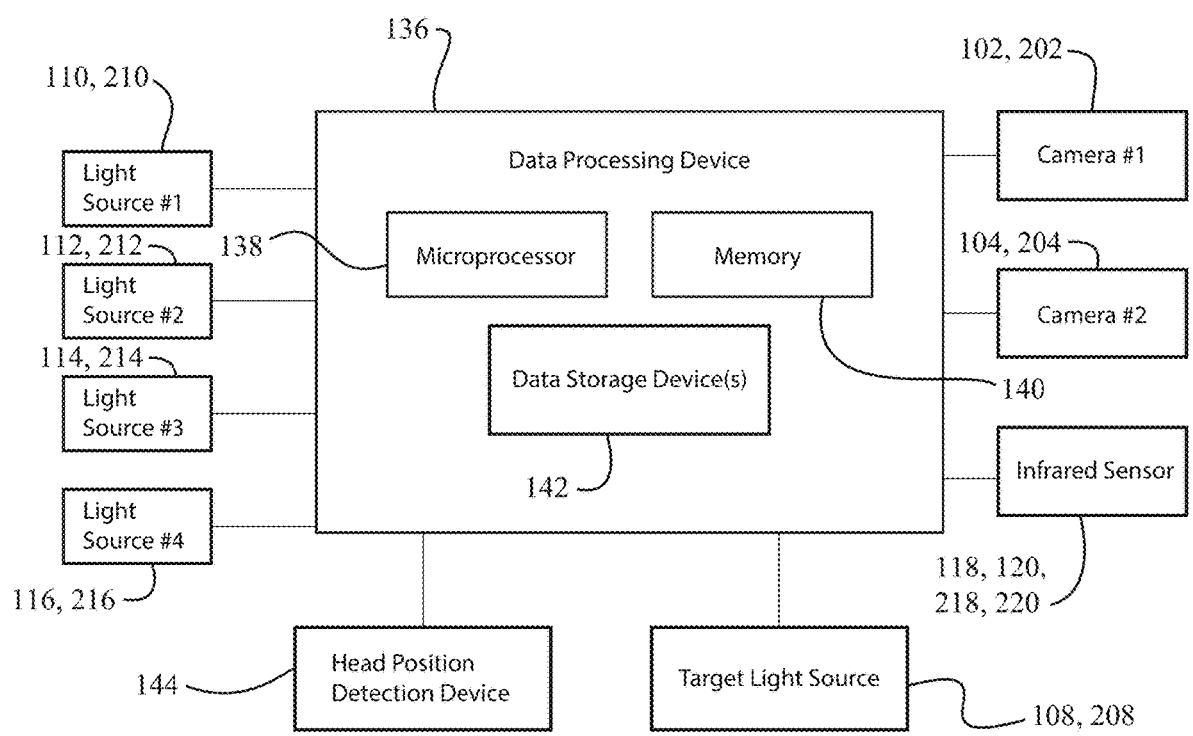
FIG. 7 is a block diagram of constituent components of the eye movement measurement devices of FIGS. 1 and 3.

A first illustrative embodiment of an eye movement measurement device is seen generally at 100 in FIGS. 1, 2, and 7. As shown in FIGS. 1, 2, and 7, the eye movement measurement device 100 of the first illustrative embodiment generally comprises a support frame 132 configured to be worn on the head of a user; a plurality of light sources 110, 112, 114, 116 mounted on the central support structure 106 of the support frame 132, the plurality of light sources 110, 112, 114, 116 configured to illuminate the eyes 10, 20 of the user; a pair of video-based sensors 102, 104 mounted on the support frame 132, the pair of video-based sensors 102, 104 configured to detect low speed eye movements of the eyes 10, 20 of the user and output a plurality of first signals based upon the detected low speed eye movements; a pair of non-video-based sensors 118, 120 mounted on the central support structure 106 of the support frame 132, the pair of non-video-based sensors 118, 120 configured to detect high speed eye movements of the one or more eyes of the user and output a plurality of second signals based upon the detected high speed eye movements; a head position detection device 144 (see FIG. 7), the head position detection device 144 configured to detect a position of the head of the user and output one or more third signals that are representative of the detected position of the head of the user; and a data processing device 136 (see FIG. 7) operatively coupled to the plurality of light sources 110, 112, 114, 116, the pair of video-based sensors 102, 104, the pair of non-video-based sensors 118, 120, and the head position detection device 144, the data processing device 136 configured to receive the plurality of first signals that are generated based upon the detected low speed eye movements, the plurality of second signals that are generated based upon the detected high speed eye movements, and the one or more third signals that are generated based upon the detected position of the head of the user, and the data processing device 136 configured to determine one or more gaze directions of the user from the plurality of first signals output by the pair of video-based sensors 102, 104, the plurality of second signals output by the pair of non-video-based sensors 118, 120, and the one or more third signals output by the head position detection device 144.

In the illustrative embodiment, the eye movement output values are given in terms of degrees of displacement. The center gaze is labeled as 0 degrees. Horizontal and vertical deviations of a line that projects out of the center of pupil from the center gaze, measured in degrees, represent the horizontal and vertical eye movements. Prior to data collection, a calibration is necessary to convert the measured parameters into actual eye movements.

In the illustrative embodiment, the calibration process involves asking the user to look back and forth among two or more pre-specified dots placed in front of the user that generate known eye angles. The values derived during the calibration process are then used to convert the measured parameters into eye movements.

Now, with reference again to FIGS. 1, 2, and 7, the plurality of light sources 110, 112, 114, 116 of the eye movement measurement device 100 will be described. As shown in the front and side views of FIGS. 1 and 2, in the illustrative embodiment, each of the plurality of light sources 110, 112, 114, 116 comprises one or more light emitting diodes (LEDs) configured to illuminate the one or more eyes of the user. The data processing device 136 is configured to activate the one or more light emitting diodes prior to detection of the low speed eye movements by the pair of video-based sensors 102, 104 and prior to detection of the high speed eye movements by the non-video-based sensors 118, 120. The light emitting diodes remain on during the entirety of the eye movement testing to illuminate the eyes of the user. In the illustrative embodiment, the plurality of light emitting diodes may be in form of infrared light emitting diodes.

Referring to FIGS. 1 and 2, the pair of video-based sensors 102, 104 of the eye movement measurement device 100 will be explained. In the illustrative embodiment, each of the pair of video-based sensors 102, 104 comprises a video camera mounted proximate to a respective eyebrow 40 of the user. In one exemplary embodiment, the pair of video cameras may comprise a pair of infrared cameras. Although, in an alternative embodiment, rather than being in the form of infrared cameras, the video cameras may be in the form of black-and-white cameras or color cameras. In the illustrative embodiment, each of the video cameras is in the form of a high-speed camera (e.g., a 250 Hz camera or other suitable high-speed camera). Also, in the illustrative embodiment, the video-based sensors 102, 104 measure low-speed eye movements, which are eye movements less than or equal to 100 degrees per second.

Next, the pair of non-video-based sensors 118, 120 will be described with reference to FIGS. 1 and 2. In the illustrative embodiment, the non-video-based sensors 118, 120 utilize direct infrared illumination and sensing means (see FIGS. 1 and 2). In the illustrative embodiment, the nasal portion of both eyes 10, 20 of the user is illuminated by infrared light and the infrared sensors 118, 120 are used to measure the amount of reflected infrared light (as shown in the diagrammatic view of FIG. 6). For example, as the corneal bulge (i.e., the protruding spherical cornea) of the eyes 10, 20 of the user moves away from the light sources 110, 112, 114, 116, less light is reflected to the infrared light detectors 118, 120, which may be in the form of photodiodes or other types of sensors for detecting infrared light. In the illustrative embodiment, the illuminators 110, 112, 114, 116 and sensors 118, 120 may be attached to the nose bridge component 122 of the head-mounted support frame 132 by means of the central support structure 106. The measurement principle of the illustrative non-video-based sensors 118, 120 is based on taking the differences between the averages of reflected light from the areas of the eyes 10, 20 near the nose 30 of the user. In the illustrative embodiment, the non-video-based sensors 118, 120 measure high-speed eye movements, which are eye movements greater than 100 degrees per second. In the illustrative embodiment, the sampling rate of the non-video-based sensors 118, 120 may be 1,000 Hz or more. In other embodiments, rather than using direct infrared illumination and sensing means for the non-video-based sensors 118, 120, the non-video-based sensors may be in the form of ultrasound sensors, electooculographic sensors, and combinations thereof.

In the illustrative embodiment, the data from the video-based sensors 102, 104 and the non-video-based sensors 118, 120 is collected in parallel. The video-based sensors 102, 104 track the centers of the pupils and convert them to eye movements. The non-video-based sensors 118, 120 track the curvature of the cornea and convert it to eye movements. Using the time stamps from both the video-based sensors 102, 104 and the non-video-based sensors 118, 120, the eye movement data from the sensors 102, 104, 118, 120 is synchronized. The measured values from the video sensors 102, 104 are used to correct for the drift of the non-video tracings. Conversely, the measured values from the non-video sensors 118, 120 are used to add samples to the tracings from the video sources. The combined tracings derived from this process can accurately represent both slow and fast eye movements.

As mentioned above, in the illustrative embodiment, the measurements from both the video-based and non-video-based sensors 102, 104, 118, 120 are eventually converted to represent eye movements in degrees. The time stamps from both sets of sensors 102, 104, 118, 120 are used to synchronize the recordings. The video-based sensors 102, 104 have a better low-frequency performance, which is used to correct for drift of the non-video-based sensors 118, 120. The non-video-based sensors 118, 120 have a better high-frequency performance, which is used to increase the number of sampling points during fast eye movements. In addition, after the data processing, eye velocities in degrees per second are eventually calculated. At the same time, the head velocities can be measured using a head position detection device 144, which may be in the form of an inertial measurement unit (IMU) embedded in the support frame 132 worn by the user. The performance of the vestibulo-ocular reflex (VOR) is quantified by comparing the head velocity versus the eye velocities. The ratio of slow eye velocities (VOR eye movements) to head velocities, as well as the number and velocity of fast eye movements (saccades) are used to quantify the subject/user performance.

Figure 6:
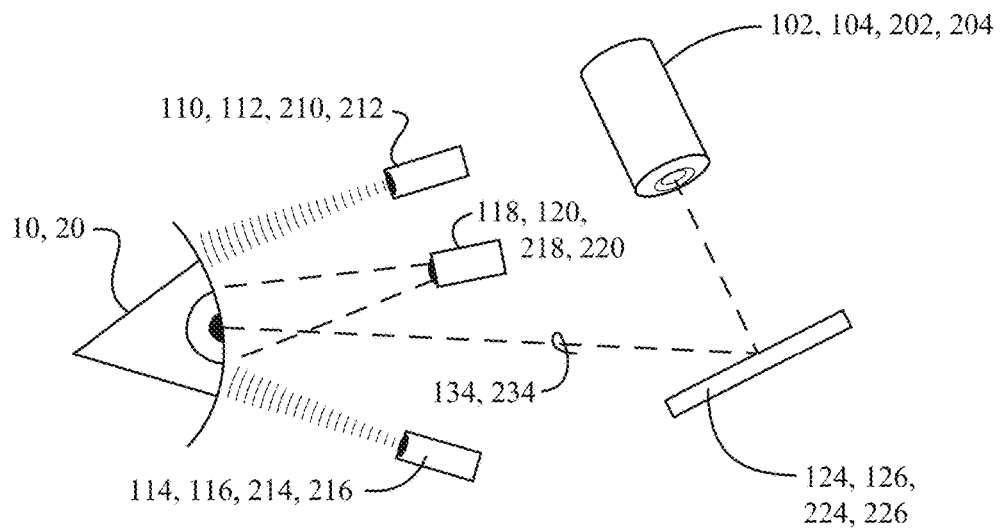
FIG. 6 is a schematic diagram illustrating the functionality of the video-based sensors and the non-video-based sensors of the eye movement measurement devices of FIGS. 1 and 3.

As shown in FIGS. 1 and 2, the eye movement measurement device 100 further includes a pair of dichroic mirrors 124, 126 mounted to the lower portion of the support frame 132. Each of the dichroic mirrors 124, 126 is secured to the lower portion of the support frame 132 by a respective pair of spaced-apart mounting brackets 128. In the first illustrative embodiment, it can be seen that the field of view of the user is substantially unobstructed by the dichroic mirrors 124, 126 because the mirrors 124, 126 are positioned below the eyes 10, 20 of the user. In the schematic diagram of FIG. 6, it can be seen each dichroic mirror 124, 126 is disposed in the path 134 of the reflected eye image between the eye 10, 20 and the respective camera 102, 104. As shown in FIG. 6, the image of the eye 10, 20 is reflected off the dichroic mirror 124, 126, and captured by the lens of the camera 102, 104.

Turning to FIG. 7, the head position detection device 144 of the eye movement measurement device 100 will be explained. In the illustrated embodiment, the head position detection device 144 is mounted on the support frame 132 that contains the pair of video-based sensors 102, 104 and the pair of non-video-based sensors 118, 120. The head position detection device 144 may be in the form of an inertial measurement unit (IMU) mounted on the support frame 132 worn by the user.

In the illustrative embodiment, it can be seen that the head-mounted support frame 132 of the eye movement measurement device 100 is in the form of an eyeglass frame worn by the user. In one or more other embodiments, the head-mounted support frame 132 may be in the form of a pair of goggles worn by the user. As shown in FIGS. 1 and 2, a head strap 130 is attached to the opposed sides of the support frame 132 for attaching the eye movement measurement device 100 to the head of the user. In the illustrative embodiment, the head strap 130 is resilient so that it is capable of being stretched to accommodate the head size of the user, and then, fitted in place on the head of the user. The head strap 130 can be formed from any suitable stretchable fabric, such as neoprene, spandex, and elastane. Alternatively, the head strap 130 could be formed from a generally non-stretchable fabric, and be provided with latching means or clasp means for allowing the head strap 130 to be split into two portions (e.g., the head strap 130 could be provided with a snap-type latching device).

In one or more further embodiments, eye movement measurement device 100 may additionally comprise a frame slippage detection device that is configured to detect a slippage of the support frame 132 relative to the head of the user. In the one or more further embodiments, the frame slippage detection device may be in the form of one or more externally disposed video cameras that are used to detect the slippage of the support frame 132. In the illustrative embodiment, the frame slippage detection device is in the form of a stationary camera disposed in front of the eye movement measurement device 100 for detecting the slippage of the support frame 132.

Also, in one or more further embodiments, the eye movement measurement device 100 may additionally comprise a light-proof cover mounted on the support frame 132. The light-proof cover is configured to at least partially surround a front of the support frame 132 so as to permit the eye movements of the user to be detected in darkness. As such, the light-proof cover enables the eye movements of the user to be recorded in complete darkness or nearly complete darkness. In one or more embodiments, the light-proof cover is in the form of a pull-down visor, such as that used on welding goggles. In one or more alternative embodiments, light-proof cover is in the form of a snap-on cover that snaps around the support frame 132, and in front of the dichroic mirrors 124, 126.

Referring again to FIG. 1, it can be seen that, in the illustrative embodiment, the eye movement measurement device 100 further comprises a target generation device (e.g., a target light source 108) mounted on the support frame 132. The target generation device 108 is configured to generate a target and project the target onto a surface (e.g., a wall surface) in front of the user such that the target is visible by the eyes 10, 20 of the user. The target generation device 108 may be in the form of a laser light source or a light emitting diode.

In addition, in one or more embodiments, the eye movement measurement device 100 further comprises a data storage device mounted on the support frame 132. The data storage device comprises non-volatile data storage means, and is configured to store eye movement data so as to enable the eye movement data to be subsequently downloaded to a remote computing device.

Now, turning to FIG. 7, it can be seen that the illustrated data acquisition/data processing device 136 (e.g., a computing device) of the eye movement measurement device 100 includes a microprocessor 138 for processing data, memory 140 (e.g., random access memory or RAM) for storing data during the processing thereof, and data storage device(s) 142, such as one or more hard drives, compact disk drives, floppy disk drives, flash drives, or any combination thereof. As shown in FIG. 7, the light sources 110, 112, 114, 116, the pair of video-based sensors 102, 104, and the pair of non-video-based sensors 118, 120 are operatively coupled to the data acquisition/data processing device 136. Also, as illustrated in FIG. 7, the target light source 108 and the head position detection device 144 are operatively coupled to the data acquisition/data processing device 136. In some embodiments, the data acquisition/data processing device 136 can be in the form of a desktop computer or laptop computer remotely located from the support frame 132 of the eye movement measurement device 100, while in other embodiments, the data acquisition/data processing device 136 can be embodied as a mini-computer mounted on the support frame 132.

In the illustrative embodiment, the data processing device 136 is operatively coupled to the light sources 110, 112, 114, 116, the pair of video-based sensors 102, 104, the pair of non-video-based sensors 118, 120, the target light source 108 and the head position detection device 144 by means of a wireless connection. In an alternative embodiment, the data processing device 136 may be operatively coupled to the light sources 110, 112, 114, 116, the pair of video-based sensors 102, 104, the pair of non-video-based sensors 118, 120, the target light source 108 and the head position detection device 144 by means of a hardwired connection.

FIGS. 3-5 illustrate an eye movement measurement device 200 according to a second illustrative embodiment of the present invention. With reference to these figures, it can be seen that, in many respects, the second illustrative embodiment is similar to that of the first embodiment. Moreover, some parts are common to both such embodiments. For the sake of brevity, the elements that the second embodiment of the eye movement measurement device has in common with the first embodiment will only be briefly mentioned, if at all, because these components have already been explained in detail above Initially, referring collectively to FIGS. 3-5 and 7, it can be seen that, like the first illustrative embodiment, the eye movement measurement device 200 of the second illustrative embodiment generally comprises a support frame 232 configured to be worn on the head of a user; a plurality of light sources 210, 212, 214, 216 mounted on the central support structure 206 of the support frame 232, the plurality of light sources 210, 212, 214, 216 configured to illuminate the eyes 10, 20 of the user; a pair of video-based sensors 202, 204 mounted on the support frame 232, the pair of video-based sensors 202, 204 configured to detect low speed eye movements of the eyes 10, 20 of the user and output a plurality of first signals based upon the detected low speed eye movements; a pair of non-video-based sensors 218, 220 mounted on the central support structure 206 of the support frame 232, the pair of non-video-based sensors 218, 220 configured to detect high speed eye movements of the one or more eyes of the user and output a plurality of second signals based upon the detected high speed eye movements; a head position detection device 144 (see FIG. 7), the head position detection device 144 configured to detect a position of the head of the user and output one or more third signals that are representative of the detected position of the head of the user; and a data processing device 136 (see FIG. 7) operatively coupled to the plurality of light sources 210, 212, 214, 216, the pair of video-based sensors 202, 204, the pair of non-video-based sensors 218, 220, and the head position detection device 144, the data processing device 136 configured to receive the plurality of first signals that are generated based upon the detected low speed eye movements, the plurality of second signals that are generated based upon the detected high speed eye movements, and the one or more third signals that are generated based upon the detected position of the head of the user, and the data processing device 136 configured to determine one or more gaze directions of the user from the plurality of first signals output by the pair of video-based sensors 202, 204, the plurality of second signals output by the pair of non-video-based sensors 218, 220, and the one or more third signals output by the head position detection device 144.

As explained above for the first illustrative embodiment, the eye movement output values are given in terms of degrees of displacement. The center gaze is labeled as 0 degrees. Horizontal and vertical deviations of a line that projects out of the center of pupil from the center gaze, measured in degrees, represent the horizontal and vertical eye movements.

Now, with reference again to FIGS. 3-5 and 7, the plurality of light sources 210, 212, 214, 216 of the eye movement measurement device 200 will be described. As shown in the front and side views of FIGS. 3 and 4, in the illustrative embodiment, each of the plurality of light sources 210, 212, 214, 216 comprises one or more light emitting diodes (LEDs) configured to illuminate the one or more eyes of the user. The data processing device 136 is configured to activate the one or more light emitting diodes prior to detection of the low speed eye movements by the pair of video-based sensors 202, 204 and prior to detection of the high speed eye movements by the non-video-based sensors 218, 220. The light emitting diodes remain on during the entirety of the eye movement testing to illuminate the eyes of the user. As described above for the first embodiment, in the illustrative embodiment, the plurality of light emitting diodes may be in form of infrared light emitting diodes.

Referring to FIGS. 3 and 4, the pair of video-based sensors 202, 204 of the eye movement measurement device 200 will be explained. In the illustrative embodiment, each of the pair of video-based sensors 202, 204 comprises a video camera mounted proximate to a respective temple of the user (i.e., each video camera 202, 204 is disposed outwardly from a respective eye of the user—see FIG. 3). In one exemplary embodiment, the pair of video cameras may comprise a pair of infrared cameras. Although, in an alternative embodiment, rather than being in the form of infrared cameras, the video cameras may be in the form of black-and-white cameras or color cameras. In the illustrative embodiment, each of the video cameras is in the form of a high-speed camera (e.g., a 250 Hz camera or other suitable high-speed camera). Also, in the illustrative embodiment, the video-based sensors 202, 204 measure low-speed eye movements, which are eye movements less than or equal to 100 degrees per second.

Next, the pair of non-video-based sensors 218, 220 will be described with reference to FIGS. 3 and 4. In the illustrative embodiment, the non-video-based sensors 218, 220 utilize direct infrared illumination and sensing means (see FIGS. 3 and 4). In the illustrative embodiment, the nasal portion of both eyes 10, 20 of the user is illuminated by infrared light and the infrared sensors 218, 220 are used to measure the amount of reflected infrared light (as shown in the diagrammatic view of FIG. 6). For example, as the corneal bulge (i.e., the protruding spherical cornea) of the eyes 10, 20 of the user moves away from the light sources 210, 212, 214, 216, less light is reflected to the infrared light detectors 218, 220, which may be in the form of photodiodes or other types of sensors for detecting infrared light. In the illustrative embodiment, the illuminators 210, 212, 214, 216 and sensors 218, 220 may be attached to the nose bridge component 222 of the head-mounted support frame 232 by means of the central support structure 206. The measurement principle of the illustrative non-video-based sensors 218, 220 is based on taking the differences between the averages of reflected light from the areas of the eyes 10, 20 near the nose 30 of the user. In the illustrative embodiment, the non-video-based sensors 218, 220 measure high-speed eye movements, which are eye movements greater than 100 degrees per second. In other embodiments, rather than using direct infrared illumination and sensing means for the non-video-based sensors 218, 220, the non-video-based sensors may be in the form of ultrasound sensors, electooculographic sensors, and combinations thereof.

As described above for the first illustrative embodiment, the data from the video-based sensors 202, 204 and the non-video-based sensors 218, 220 is collected in parallel. The video-based sensors 202, 204 track the centers of the pupils and convert them to eye movements. The non-video-based sensors 218, 220 track the curvature of the cornea and convert it to eye movements. Using the time stamps from both the video-based sensors 202, 204 and the non-video-based sensors 218, 220, the eye movement data from the sensors 202, 204, 218, 220 is synchronized. The measured values from the video sensors 202, 204 are used to correct for the drift of the non-video tracings. Conversely, the measured values from the non-video sensors 218, 220 are used to add samples to the tracings from the video sources. The combined tracings derived from this process can accurately represent both slow and fast eye movements.

As mentioned above, in the illustrative embodiment, the measurements from both the video-based and non-video-based sensors 202, 204, 218, 220 are eventually converted to represent eye movements in degrees. The time stamps from both sets of sensors 202, 204, 218, 220 are used to synchronize the recordings. The video-based sensors 202, 204 have a better low-frequency performance, which is used to correct for drift of the non-video-based sensors 218, 220. That is, the output data from the video-based sensors 202, 204 may be used to determine the amount by which the sampling curve produced by the non-video-based sensors 218, 220 is shifted or offset due to the effects of sensor drift. The non-video-based sensors 218, 220 have a better high-frequency performance, which is used to increase the number of sampling points during fast eye movements. That is, the additional sampling points generated by the non-video-based sensors 218, 220 may be used to fill-in sampling points between the sampling points generated using the video-based sensors 202, 204 by using an interpolation algorithm, etc. (e.g., a quadratic interpolation algorithm). For example, the equation provided below may be used to align the curves generated by the video-based sensors 202, 204 and the non-video-based sensors 218, 220 so that the drift and additional sampling point corrections may be applied:

$$\vec{N} = a \cdot I \cdot \vec{S} + b \qquad (1)$$

where:

$\vec{N}$: interpolated values for a series of time points obtained from the video-based sensor(s);

$I$: identity matrix; and $\vec{S}$: sensed values for the same time points obtained from the non-video-based sensors.

In addition to applying the drift and additional sampling point corrections, in the illustrative embodiment, a cross-correlation technique may also be applied so as to correct for an unknown time shift due to an unknown latency in the video output data generated by the video-based sensors 202, 204 (i.e., cameras). In addition, after the data processing, eye velocities in degrees per second are eventually calculated. At the same time, the head velocities can be measured using the head position detection device 144, which may be in the form of an inertial measurement unit (IMU) embedded in the support frame 232 worn by the user. The performance of the vestibulo-ocular reflex (VOR) is quantified by comparing the head velocity versus the eye velocities. The ratio of slow eye velocities (VOR eye movements) to head velocities, as well as the number and velocity of fast eye movements (saccades) are used to quantify the subject/user performance.

As shown in FIGS. 3-5, the eye movement measurement device 200 further includes a pair of dichroic mirrors 224, 226 mounted to the central support structure 206 of the support frame 232. In the second illustrative embodiment, it can be seen that the dichroic mirrors 224, 226 are disposed in front of the eyes 10, 20 of the user so as to generally cover the field of view of the user, rather than being positioned below the eyes 10, 20 of the user, as in the first illustrative embodiment. Each of the dichroic mirrors 224, 226 is configured so as to reflect the eye image back to the camera 202, 204, yet still allow the user to see through the mirror 224, 226 so that the surrounding environment is visible to him or her. Particularly, in the schematic diagram of FIG. 6, it can be seen each dichroic mirror 224, 226 is disposed in the path 234 of the reflected eye image between the eye 10, 20 and the respective camera 202, 204. As shown in FIG. 6, the image of the eye 10, 20 is reflected off the dichroic mirror 224, 226, and captured by the lens of the camera 202, 204.

Turning to FIG. 7, the head position detection device 144 of the eye movement measurement device 200 will be explained. Similar to that described above for the first illustrative embodiment, the head position detection device 144 is mounted on the support frame 232 that contains the pair of video-based sensors 202, 204 and the pair of non-video-based sensors 218, 220. The head position detection device 144 may be in the form of an inertial measurement unit (IMU) mounted on the support frame 232 worn by the user.

In the illustrative embodiment, it can be seen that the head-mounted support frame 232 of the eye movement measurement device 200 is in the form of an eyeglass frame worn by the user. In one or more other embodiments, the head-mounted support frame 232 may be in the form of a pair of goggles worn by the user. As shown in FIGS. 3 and 4, a head strap 230 is attached to the opposed sides of the support frame 232 for attaching the eye movement measurement device 200 to the head of the user. In the illustrative embodiment, the head strap 230 is resilient so that it is capable of being stretched to accommodate the head size of the user, and then, fitted in place on the head of the user. The head strap 230 can be formed from any suitable stretchable fabric, such as neoprene, spandex, and elastane. Alternatively, the head strap 230 could be formed from a generally non-stretchable fabric, and be provided with latching means or clasp means for allowing the head strap 230 to be split into two portions (e.g., the head strap 230 could be provided with a snap-type latching device).

In one or more further embodiments, eye movement measurement device 200 may additionally comprise a frame slippage detection device that is configured to detect a slippage of the support frame 232 relative to the head of the user. In the one or more further embodiments, the frame slippage detection device may be in the form of one or more externally disposed video cameras that are used to detect the slippage of the support frame 232. In the illustrative embodiment, the frame slippage detection device is in the form of a stationary camera disposed in front of the eye movement measurement device 200 for detecting the slippage of the support frame 232.

Also, in one or more further embodiments, the eye movement measurement device 200 may additionally comprise a light-proof cover mounted on the support frame 232. The light-proof cover is configured to at least partially surround a front of the support frame 232 so as to permit the eye movements of the user to be detected in darkness. As such, the light-proof cover enables the eye movements of the user to be recorded in complete darkness or nearly complete darkness. In one or more embodiments, the light-proof cover is in the form of a pull-down visor, such as that used on welding goggles. In one or more alternative embodiments, light-proof cover is in the form of a snap-on cover that snaps around the support frame 232, and in front of the dichroic mirrors 224, 226.

Figure 8:
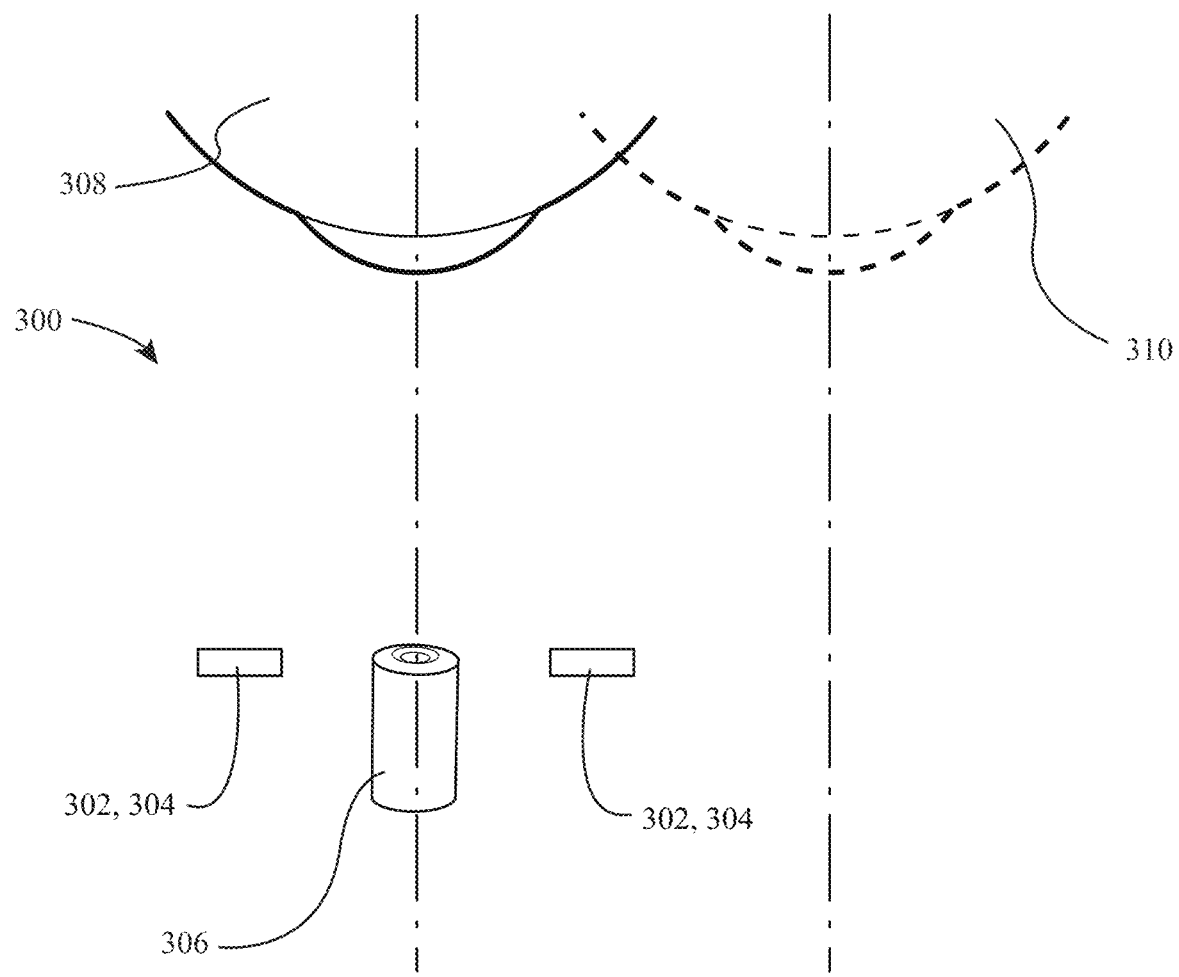
FIG. 8 is a schematic diagram illustrating the manner in which a video-based sensor is capable of being used for the alignment of non-video-based sensors.
Figure 9:
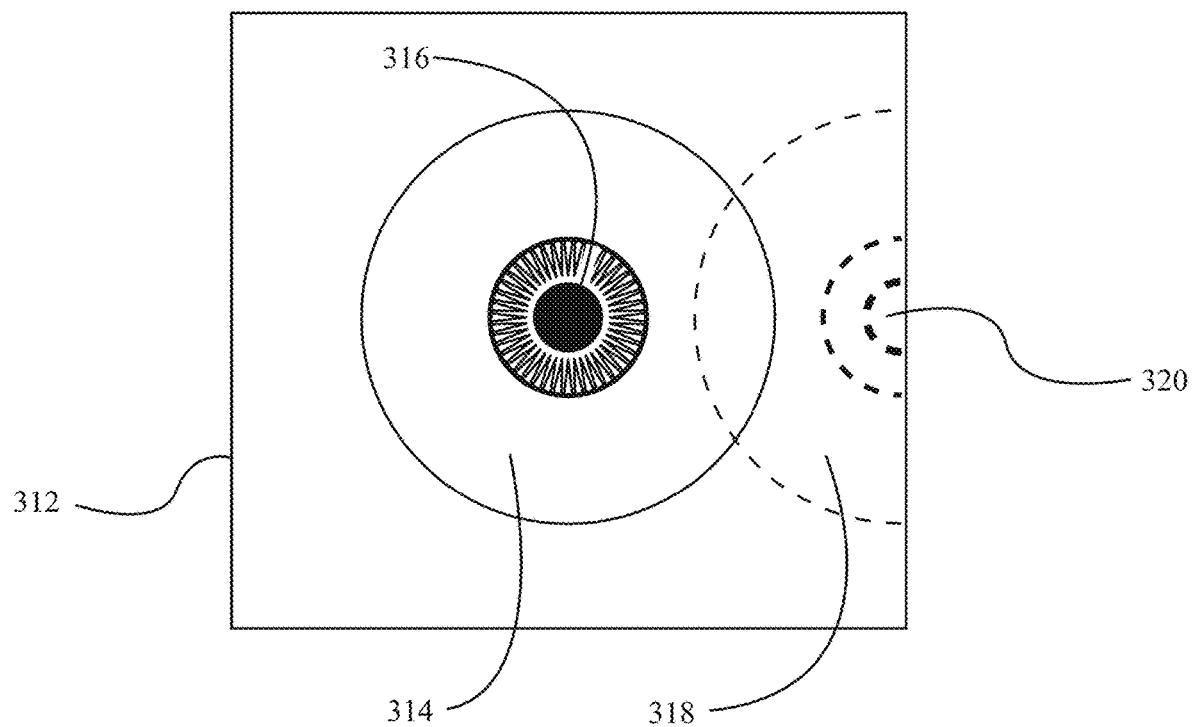
FIG. 9 depicts an example alignment of an eye using an image captured by the video-based sensor of FIG. 8.

In addition, in one or more further embodiments, the non-video-based sensors (e.g., infrared sensors) may be located relative to the optical of axis of the video-based sensor(s) (e.g., a camera) according to a known relationship (e.g., a predetermined distance or distances between the sensors, etc.) so as to enable the video-based sensor(s) to be used for the alignment of the non-video-based sensors. For example, as shown in the schematic diagram 300 of FIG. 8, non-video-based sensors 302, 304 are arranged on opposite sides of the video-based sensor 306, which may be in the form of a camera 306. More specifically, the non-video-based sensors 302, 304 are spaced apart from the camera optical axis (as indicated by the centerline in FIG. 8) by known horizontal distances. In FIG. 8, the actual position of the eye 310 is shown offset to the right of the optical axis of the camera 306. As shown in FIG. 8, the desired position of the eye 308 is centered on the camera optical axis. Because a known fixed relationship exists between the location of the camera 306 and the non-video-based sensors 302, 304 in FIG. 8, the non-video-based sensors 302, 304 may be aligned in accordance with the actual position of the eye 310 by using the image information obtained from the camera 306. For example, FIG. 9 depicts an example alignment of an eye using an image 312 captured by the camera 306 in FIG. 8. In FIG. 9, the eye 318 with pupil 320 depicts the actual location of the eye as captured by the camera 306, while the centered eye 314 with pupil 316 depicts the desired position of the eye in the image. The offset distance between the eye 318 and the eye 314 in FIG. 9 may be used to adjust the non-video-based sensors 302, 304 of FIG. 8 to account for the non-centered position of the eye 318.

Figure 11A:
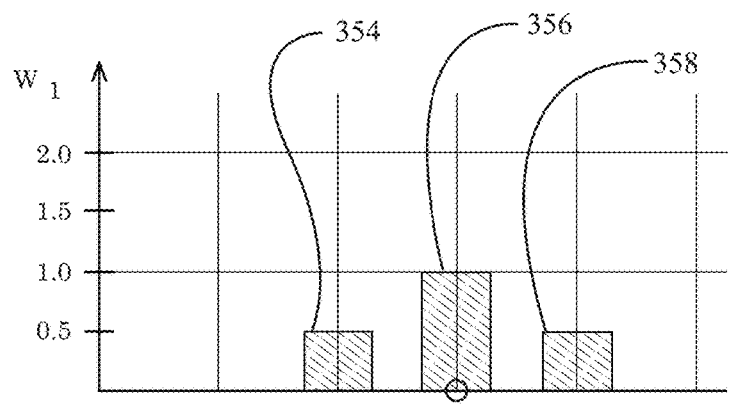
FIG. 11A is a first bar graph illustrating numerical weights applied to the sensor output values of the non-video-based sensors in FIG. 10A.

Next, referring to FIGS. 10A-10C and 11A-11C, an exemplary manner in which the non-video-based sensors may be calibrated so as to compensate for the misalignment of an eye relative to the non-video-based sensors will be described. Initially, as shown in FIG. 10A, the central axis 334 of the eye 322 is shown centered on, and bisecting the dimensional line 328 extending from the center location of the first set of non-video-based sensors 336 to the center location of the second set of non-video-based sensors 338. Because the eye 322 is centered relative to both sets of non-video-based sensors 336, 338 in FIG. 10A, a weight of 1.0 is applied to the centermost sensors 340, 342 of each non-video-based sensor set 336, 338, while a weight of 0.5 is applied to the two sensors disposed on opposite sides of the centermost sensors 340, 342. The weighting of the non-video-based sensors 336, 338 is graphically illustrated in the bar graph 352 of FIG. 11A. As shown in FIG. 11A, the weights of 1.0 that are applied to the centermost sensors 340, 342 are represented by the center bar 356, while the weights of 0.5 that are applied to the two sensors disposed on opposite sides of the centermost sensors 340, 342 are represented by the bars 354, 358.

Figure 11B:
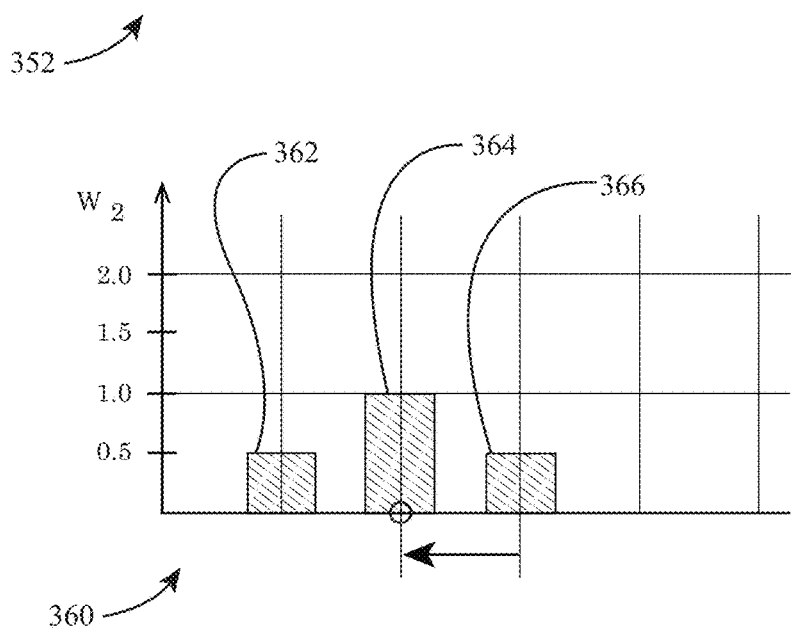
FIG. 11B is a second bar graph illustrating numerical weights applied to the sensor output values of the non-video-based sensors in FIG. 10B.

Turning FIG. 10B, the central axis 334 of the eye 324 is shown offset to the left of the midpoint of the dimensional line 328 by a first distance 330. Because the eye 324 is misaligned to the left relative to both sets of non-video-based sensors 336, 338 in FIG. 10B, a weight of 1.0 is applied to the sensors 344, 346 of each non-video-based sensor set 336, 338, while a weight of 0.5 is applied to the two sensors disposed on opposite sides of the sensors 344, 346. The weighting of the non-video-based sensors 336, 338 is graphically illustrated in the bar graph 360 of FIG. 11B. As shown in FIG. 11B, the weights of 1.0 that are applied to the sensors 344, 346 are represented by the bar 364, while the weights of 0.5 that are applied to the two sensors disposed on opposite sides of the sensors 344, 346 are represented by the bars 362, 366.

Figure 11C:
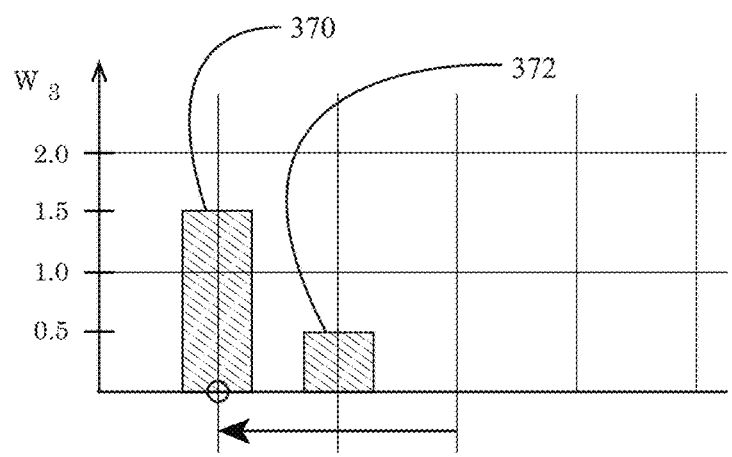
FIG. 11C is a third bar graph illustrating numerical weights applied to the sensor output values of the non-video-based sensors in FIG. 10C.

Next, as shown in FIG. 10C, the central axis 334 of the eye 326 is shown offset to the left of the midpoint of the dimensional line 328 by a second distance 332, which is greater than the offset distance 330 of FIG. 10B. Because the eye 326 is misaligned to the left relative to both sets of non-video-based sensors 336, 338 in FIG. 10C by a greater distance than that of FIG. 10B, a weight of 1.5 is applied to the leftmost sensors 348, 350 of each non-video-based sensor set 336, 338, while a weight of 0.5 is applied to the sensors disposed on right sides of the sensors 348, 350. The weighting of the non-video-based sensors 336, 338 is graphically illustrated in the bar graph 368 of FIG. 11C. As shown in FIG. 11C, the weights of 1.5 that are applied to the sensors 348, 350 are represented by the bar 370, while the weights of 0.5 that are applied to the sensors disposed on right sides of the sensors 348, 350 are represented by the bar 372.

In the embodiment of FIGS. 10A-10C and 11A-11C, the misalignment of the eye relative to the non-video-based sensors is compensated for by selectively applying weights to particular sensors in sensor sets. Although, in other embodiments, the misalignment of the eye relative to the non-video-based sensors may be compensated for by translating and/or rotating the non-video-based sensors using actuators based upon the information obtained from the video-based sensor(s).

Referring again to FIG. 3, it can be seen that, in the illustrative embodiment, the eye movement measurement device 200 further comprises a target generation device (e.g., a target light source 208) mounted on the support frame 232. The target generation device 208 is configured to generate a target and project the target onto a surface (e.g., a wall surface) in front of the user such that the target is visible by the eyes 10, 20 of the user. The target generation device 208 may be in the form of a laser light source or a light emitting diode.

In addition, in one or more embodiments, the eye movement measurement device 200 further comprises a data storage device mounted on the support frame 232. The data storage device comprises non-volatile data storage means, and is configured to store eye movement data so as to enable the eye movement data to be subsequently downloaded to a remote computing device.

The data processing device 136 of the eye movement measurement device 200 is the same as that described above for the first embodiment. In the illustrative embodiment, the data processing device 136 is operatively coupled to the light sources 210, 212, 214, 216, the pair of video-based sensors 202, 204, the pair of non-video-based sensors 218, 220, the target light source 208 and the head position detection device 244 by means of a wireless connection. In an alternative embodiment, the data processing device 136 may be operatively coupled to the light sources 210, 212, 214, 216, the pair of video-based sensors 202, 204, the pair of non-video-based sensors 218, 220, the target light source 208 and the head position detection device 144 by means of a hardwired connection.

In the illustrative embodiment, the eye movement measurement devices 100, 200 are configured to determine the gaze direction of a subject. Once the subject has been outfitted with the eye movement measurement device 100, 200, the eye movement of the subject is determined based upon the output data from the video-based sensors 102, 104, 202, 204 and the non-video-based sensors 118, 120, 218, 220 of the eye movement tracking device 100, 200, while the head position of the subject is determined based upon the output data from the head position detection device 144. The gaze direction of the subject is generally equal to the sum of the head movement and the eye movement, and is given in degrees per second.

The eye movement measurement devices 100, 200 described above may be used for a variety of different eye tests. For example, the eye movement measurement devices 100, 200 may be used in head impulse testing in which the subject's head is moved rapidly either in the horizontal or vertical planes. The examining clinician or physician stands behind the subject while holding the head. The subject is instructed to stare at a stationary dot placed about one meter straight ahead. During several rapid head movements either horizontally (right-left) or vertically (up-down), the eye and head velocities will be determined by the device and used to quantify the performance of the semicircular canals within the vestibular system.

Figure 12:
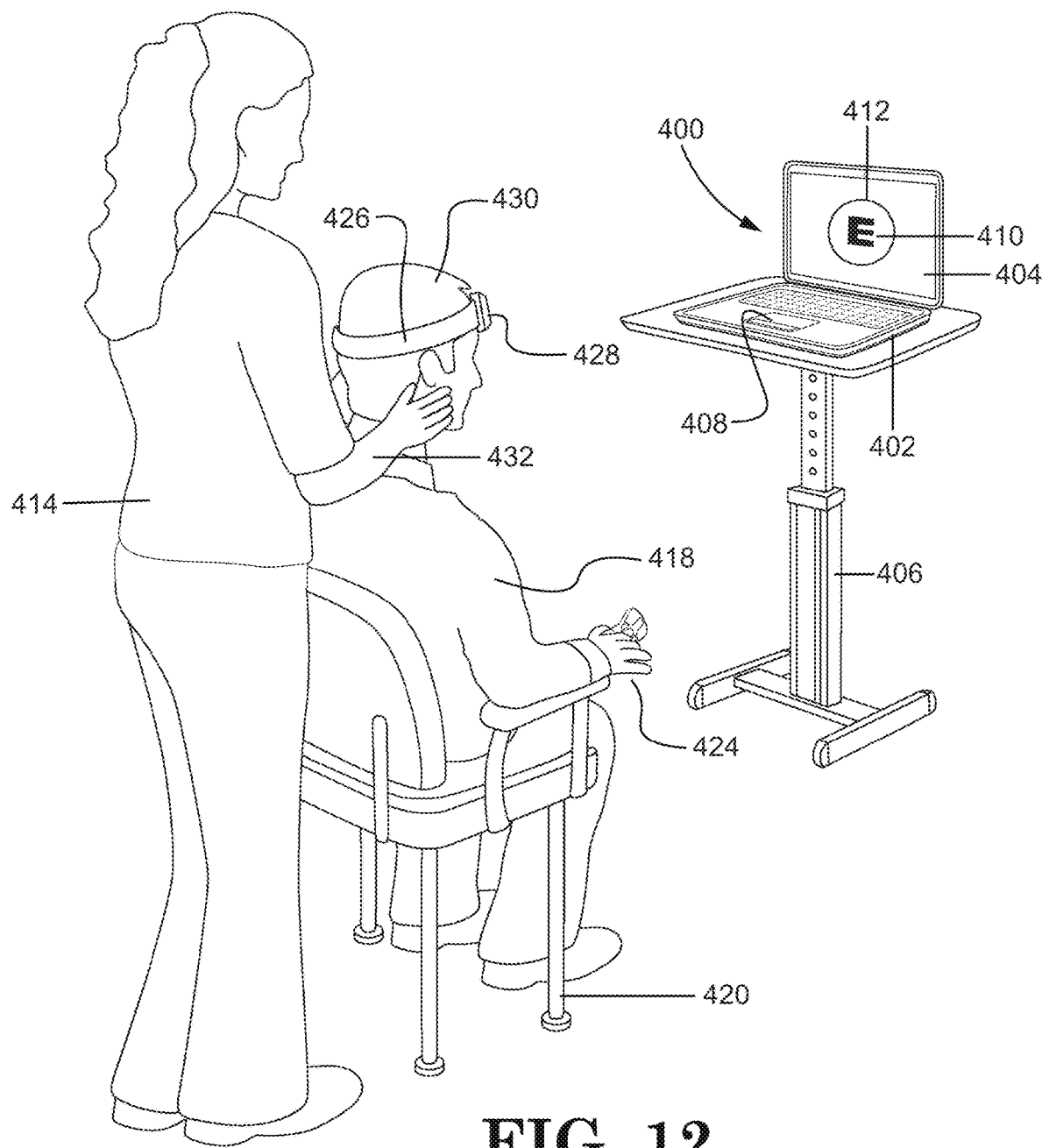
FIG. 12 is a diagrammatic perspective view of a first exemplary vision testing system that utilizes a laptop computing device, according to a further embodiment of the invention.

In one or more further embodiments, a vision testing system is disclosed that is particularly configured for head impulse testing on a subject. An illustrative embodiment of a vision testing system for head impulse testing is seen generally at 400 in FIG. 12. In the illustrative embodiment, the vision testing system 400 generally comprises a laptop computing device 402 with a visual display device 404. The laptop computing device 402 is one exemplary form of a data processing device and/or data processing and data acquisition device. In FIG. 12, the laptop computing device 402 is disposed on an adjustable height table 406 so that the height of the laptop computing device 402 is selectively adjustable by a user. In one or more embodiments, the height of the table 406 is adjusted prior to each test session such that the center of the visual display device 404 of the laptop computing device 402, which contains the one or more visual objects 410, is generally horizontally aligned with the eyes of the subject 418 (i.e., so the subject 418 is looking straight at the visual object 410 on the visual display device 404 during the testing).

The one or more visual objects 410 (e.g., optotypes), which the subject identifies during each vision test described herein, are displayed on the visual display device 404 of the laptop computing device 402 in the illustrative embodiment. Specifically, as shown in FIG. 12, the visual object 410 is displayed on the output screen of the laptop visual display device 404 within a circle 412. The circle 412 circumscribes the visual object 410 and focuses the attention of the subject 418 on the central region of the output screen containing the visual object 410.

While a circle 412 is used to circumscribe the visual object 410 in the illustrative embodiment of FIG. 12, it is to be understood that other suitable shapes could be used to circumscribe the visual object 410 as well. For example, the visual object 410 may be alternatively circumscribed by a square or rectangle, as these shapes are also capable of effectively focusing the subject's attention on the central region of the output screen of the visual display device 404 containing the visual object 410.

In addition, while the visual object 410 in FIG. 12 is in the form of a Tumbling E optotype, it is to be understood that other suitable visual objects 410 may be used in place of the Tumbling E. For example, the visual object 410 alternatively may comprise a Landolt C optotype or an optotype comprising different letters of a recognized alphabet (e.g., different letters of the English alphabet). That is, in some embodiments, the subject 418 may identify different letters of a recognized alphabet, rather than different orientations of the same letter or optotype. Also, in other embodiments, the visual object 410 alternatively may comprise any other identifiable symbol (e.g., a crescent, a star, etc.). Further, in other embodiments, for younger subjects, the visual object 410 or optotype alternatively may comprise (i) a house, (ii) a heart, (iii) a circle, and/or (iv) a square (e.g., Lea symbols may be used for the optotype).

In one or more embodiments, different letters or objects may be displayed in succession during a particular test (e.g., during the head impulse test described hereinafter). For example, during a particular test, a Tumbling E optotype may be displayed first, then followed by the letter "K", a crescent symbol, a star symbol, etc. In this exemplary fashion, the letters that are displayed to the subject 418 can be consistently varied during the performance of the testing.

Referring again to FIG. 12, it can be seen that the head 430 of the subject 418 is fitted with a motion sensing device 428 disposed thereon. In particular, in the illustrative embodiment, the motion sensing device 428 is removably coupled to the head of the subject 418 using a stretchable, elastic headband 426 (i.e., a resilient band 426). The motion sensing device 428 is configured to measure a velocity or speed of the head 430 of the subject 418 when the head 430 of the subject 418 is displaced by the clinician 414 during the head impulse test described herein. That is, the motion sensing device 428 determines the velocity of the subject's head 430 during head impulse test (e.g., the angular velocity of the subject's head 430 in degrees per second).

In the illustrative embodiment, the motion sensing device 428 may comprise a three-dimensional motion sensing device (i.e., an inertial measurement unit (IMU)) having a 3-axis accelerometer, a 3-axis rate gyroscope, and a 3-axis compass (i.e., a 3-axis magnetometer). Also, the illustrative motion sensing device 428 may comprise a wireless data connection to the laptop computing device 402. In particular, the laptop computing device 402 may comprise a data transmission interface unit that is operatively connected to one of the output ports of the laptop computing device 402, such as the universal serial bus (USB) port of the laptop computing device 402. As such, the laptop computing device 402 provided with the data transmission interface unit wirelessly communicates with the motion sensing device 428 using a local wireless network. In addition, the exemplary motion sensing device 428 is both lightweight (e.g., less than 30 grams) and compact in size (e.g., less than 40 mm by 70 mm by 20 mm) so that it is generally comfortable for the subject 418 to wear on his or her head 430.

Next, referring to FIG. 15, an explanation of the three (3) directions of head rotation that the motion sensing device 428 is capable of detecting will be described. First, the motion sensing device 428 is configured to detect the rotation of the head 430 of the subject 418 about the yaw axis 466 of rotation as indicated by the curved arrow 472 in FIG. 15. The curved arrow 472 about the yaw axis 466 indicates the common side-to-side movement of the subject's head 430 during the vision testing. Secondly, the motion sensing device 428 is configured to detect the rotation of the head 430 of the subject 418 about the pitch axis 462 of rotation as indicated by the curved arrow 468 in FIG. 15. The curved arrow 468 about the pitch axis 462 indicates the up-and-down movement of the subject's head 430 during the vision testing. Thirdly, the motion sensing device 428 is configured to detect the rotation of the head 430 of the subject 418 about the roll axis 464 of rotation as indicated by the curved arrow 470 in FIG. 15. The curved arrow 470 about the roll axis 464 indicates the tilt-right and tilt-left movement of the subject's head 430 during the vision testing. In addition to the ability to determine head rotation about all three (3) axes of rotation, the use of a three-dimensional motion sensing device 428 advantageously permits the determination of whether the subject 418 is rotating his or her head 430 purely about the desired axis of rotation (e.g., the yaw axis) or whether there is also off-axis rotation of the subject's head 430 during the prescribed rotation (e.g., the subject is rotating his or head 430 about a combination of the yaw axis and the roll axis, or about a combination of the yaw axis and the pitch axis). Because off-axis rotation may adversely affect the accuracy of the vision testing results, it is important to determine if off-axis rotation is present during the vision testing of the subject 418. The utilization of a three-dimensional motion sensing device 428 enables the determination of this off-axis rotation.

Now, an illustrative manner in which the computing device 402 of the vision testing system 400 performs the head rotation calculations from the output of the motion sensing device 428 will be explained in detail. In particular, this calculation procedure will describe the manner in which the angular position and the angular velocity of the head of the subject 418 may be determined using the signals from the motion sensing device 428 (i.e., the head-mounted IMU) of the vision testing system 400. As explained above, in one or more embodiments, the motion sensing device 428 may be in the form of an IMU, which includes the following three triaxial sensor devices: (i) a three-axis accelerometer sensing linear acceleration $\vec{a}'$, (ii) a three-axis rate gyroscope sensing angular velocity $\vec{\omega}'$, and (iii) a three-axis magnetometer sensing the magnetic north vector The motion sensing device 428 (i.e., the IMU) senses in the local (primed) frame of reference attached to the IMU itself. Because each of the sensor devices in the IMU is triaxial, the vectors $\vec{a}'$, $\vec{\omega}'$, $\vec{n}'$ are each 3-component vectors. A prime symbol is used in conjunction with each of these vectors to symbolize that the measurements are taken in accordance with the local reference frame. The unprimed vectors that will be described hereinafter are in the global reference frame.

The objective of these calculations is to find the angular position or orientation $\vec{\theta}(t)$ and the angular velocity $\vec{\omega}(t)$ of the head of the subject 418 in the global, unprimed, inertial frame of reference. The initial orientation in the global frame of reference may be either known in advance or derived from $\vec{\theta}_0$, as will be explained below with regard to the rotation transformation matrix.

For the purposes of the calculation procedure, a right-handed coordinate system is assumed for both global and local frames of reference. The global frame of reference is attached to the Earth. The acceleration due to gravity is assumed to be a constant vector g. Also, for the purposes of the calculations presented herein, it is presumed the sensor devices of the inertial measurement unit (IMU) provide calibrated data. In addition, all of the one or more output signals from the IMU are treated as continuous functions of time. Although, it is to be understood the general form of the equations described herein may be readily discretized to account for IMU sensor devices that take discrete time samples from a bandwidth-limited continuous signal.

The angular velocity $\vec{\omega}(t)$ of the subject's head rotation is obtained by coordinate transformation using the IMU output signal(s) as follows:

$$\vec{\omega}(t)=\vec{\theta}(t)\vec{\omega}'(t) \quad (2)$$

where $\vec{\theta}(t)$ is the matrix of the rotation transformation that rotates the instantaneous local frame of reference into the global frame of reference.

The orientation $\vec{\theta}(t)$ of the subject's head rotation is obtained by single integration of the angular velocity using the IMU output signal(s) as follows:

$$\vec{\theta}(t) = \vec{\theta}_0 + \int_0^t \vec{\omega}(t)dt \quad (3)$$

$$\vec{\theta}(t) = \vec{\theta}_0 + \int_0^t \Theta(t)\vec{\omega}'(t)dt \quad (4)$$

There are two aspects to the coordinate transformation matrix $\vec{\theta}(t)$ calculation: (i) the initial value $\vec{\theta}_0 \equiv \vec{\theta}(0)$ at t=0 and (ii) subsequent updates to this value. The updates may be integrated from the angular velocity, i.e., the time derivative $\dot{\theta}$ of the rotation transformation matrix may be set as a function of the angular velocity, and then the coordinate transformation matrix becomes:

$$\vec{\Theta}(t) = \int_0^t \Theta(\tau, \vec{\omega}'(\tau))d\tau \quad (5)$$

The value at any point in time may be derived from known local and global values of both the magnetic north vector and the acceleration of gravity. Those two vectors are usually non-parallel. This is the requirement for the $\vec{\theta}(\vec{g}', \vec{n}', \vec{g}, \vec{n})$ to be unique. The knowledge of either of those vectors in isolation gives a family of non-unique solutions $\vec{\theta}(\vec{g}', \vec{g})$ or $\vec{\theta}(\vec{n}', \vec{n})$. Both are unconstrained in one component of rotation. The $\vec{\theta}(\vec{g}', \vec{n}', \vec{g}, \vec{n})$ has many known implementations, with the common one being the Kabsch algorithm.

In one or more embodiments, if a known starting global orientation is assumed, and the time-derivative of the rotation transformation matrix as a function of the angular velocity in the local frame is used, it is possible to obtain the matrix without the need for the accelerometer and magnetometer in the IMU.

Advantageously, in one or more embodiments, the motion sensing device 428 described above requires no manual calibration step or setup time, other than putting the device 428 on the head 430 of the subject 418. That is, there is no required manual calibration and/or tare step (e.g., to calibrate the accelerometer with respect to gravity and/or to zero the gyroscope) that must be performed prior to the execution of a particular test (i.e., the head impulse test). Obviating the need for manual calibration and/or a manual tare step advantageously saves valuable time during the execution of a particular test series. In order to avoid these laborious and tedious manual steps, at the beginning of every head impulse test trial, the motion sensing device 428 (i.e., inertial measurement unit 428) is automatically re-tared (or re-zeroed) to the subject's head position at that time by the computing device 402. With each of these zeroing events, the computing device 402 also checks the orientation of the motion sensing device 428 in order to make sure that it is on the subject's head 430 correctly and/or to make sure the subject 418 is still and has his or her head held in the correct orientation. The computing device 402 checks the orientation of the motion sensing device 428 by using the data from the linear accelerometer, and by determining which axis the gravity vector lies in. If the computing device 402 detects no issues with the orientation of the motion sensing device 428, nothing happens on the screen (i.e., no message is displayed in order to save time). Conversely, if the computing device 402 determines that there is a problem with the orientation of the motion sensing device 428, a flag pops up on the screen and the test will not begin (i.e., the head impulse test will not begin). In order to begin the test, the clinician must adjust the motion sensing device 428 or the subject's head 430 to the correct position and press "okay" on the keyboard of the computing device 402 to dismiss the flag. Upon the "okay" input, the motion sensing device 428 will tare to its position at that time and the test will begin. In these one or more embodiments, the flag only pops up once per trial.

Also, advantageously, in these one or more embodiments, the motion sensing device 428 does not require a flat and/or still surface for using the motion sensing device 428 (i.e., the inertial measurement unit). In addition, in these one or more embodiments, the motion sensing device 428 does not comprise an electrical cord that operatively connects it to the computing device 402. That is, the motion sensing device 428 is wirelessly coupled to the computing device 402 without the use of any electrical wires. Because the motion sensing device 428 is not tethered (i.e., it contains no electrical cord), it can advantageously accommodate various configurations and distances from the computing device 402. In other words, the configuration of the vision testing system 400 in a room is not limited by the physical limitations imposed upon the system 400 by the fixed length of an electrical cord connecting the motion sensing device 428 to the computing device 402 (e.g., the electrical cord of a tethered motion sensing device 428 may be too short to accommodate a desired testing configuration).

Referring again to FIG. 12, it can be seen that a clinician 414 is standing behind a subject 418 seated on a chair 420. During the head impulse test described herein, wherein the subject's head 430 is to be displaced back-and-forth, the clinician 414 may move the subject's head 430 using her arms 432 so that the velocity and range of motion of the subject's head 430 is capable of being more accurately controlled.

As shown in the illustrative embodiment of FIG. 12, it can also be seen that the subject 418 is holding a user input device 424 in his right hand. The user input device 424 is configured to output an input signal in response to a manipulation of the user input device by a system user (i.e., the subject 418). In the illustrative embodiment, the user input device 424 is operatively coupled to the laptop computing device 402 by wireless data transmission means. For example, the user input device 424 may comprise a wireless mouse that wirelessly communicates with the laptop computing device 402. In other embodiments, the user input device may alternatively comprise (i) a keyboard (e.g., the keyboard of the laptop computing device 402 in FIG. 12), (ii) a wireless clicking device, or (iii) a voice recognition device that allows the subject 418 to verbally input the subject's response (e.g., to record the subject's perceived orientation of the optotype).

In the illustrative embodiment, when the user input device comprises a voice recognition device, the voice recognition device is configured to capture verbal responses of the user regarding the one or more configurations of the visual object that are identified by the user so as to obviate a need for a clinician that records the verbal responses of the user.

Figure 14:
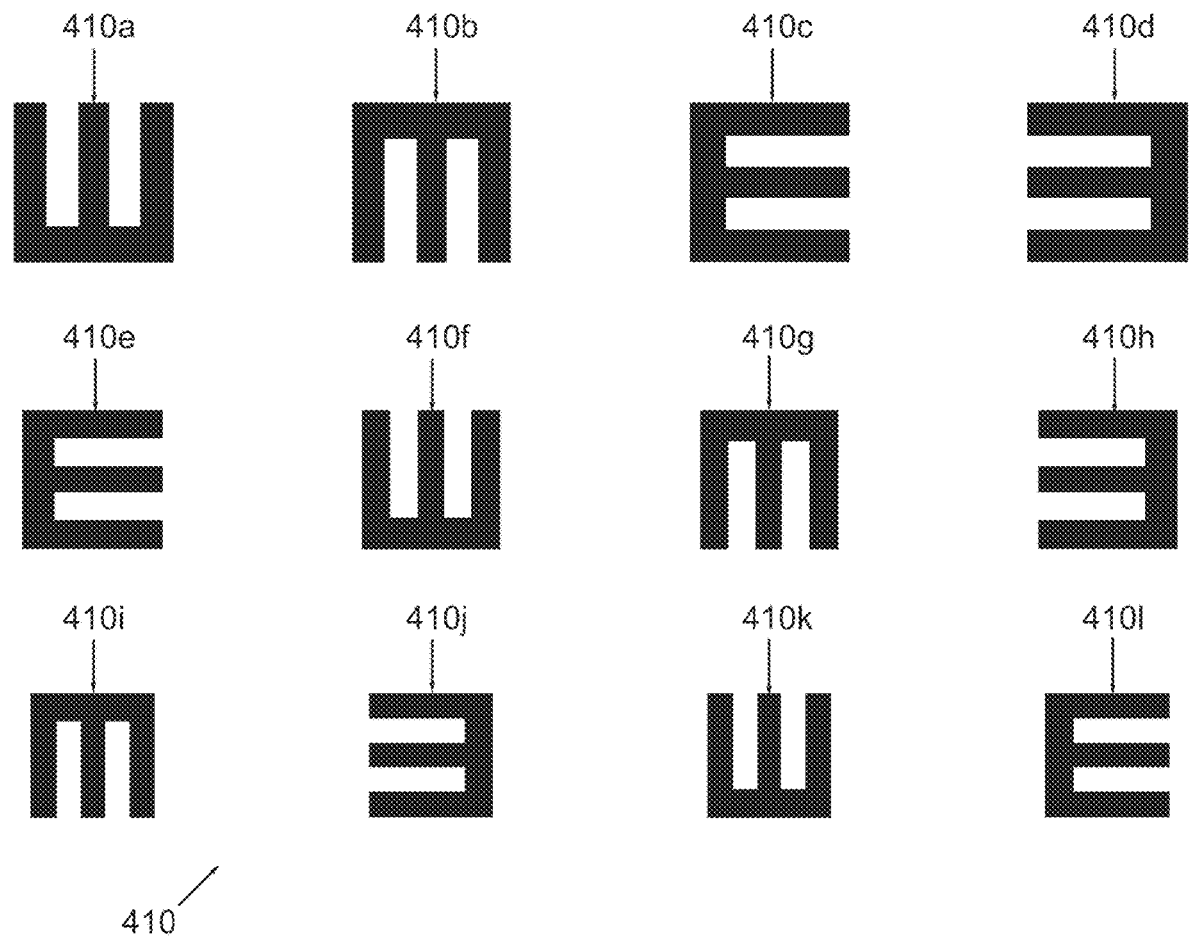
FIG. 14 is an illustration of an exemplary type of optotype that may be utilized in the embodiments of the vision testing systems described herein.

During the vision testing of the subject 418, after the subject 418 identifies the perceived configuration of the visual object 410 that is displayed on the visual display device 404, the subject 418 may use the user input device 424 in order to enter and transmit his or her response (i.e., the perceived configuration of the visual object 410) to the laptop computing device 402. In one or more embodiments, the user input device 424 is configured to accept at least four different responses of the subject 418, wherein each of the at least four different responses of the subject 418 correspond to different configurations of the visual object 410. For example, turning to FIG. 14, it can be seen that, if the visual object 410 is in the form of a Tumbling E optotype, a first configuration of the visual object 410a is one in which the Tumbling E is pointing up (see the top row of FIG. 14), a second configuration of the visual object 410b is one in which the Tumbling E is pointing down, a third configuration of the visual object 410c is one in which the Tumbling E is pointing to the right, and a fourth configuration of the visual object 410d is one in which the Tumbling E is pointing to the left. Next, referring to the middle row of FIG. 14, it can be seen that these same four configurations of the Tumbling E can be displayed on the visual display device 404 in a smaller overall size (e.g., Tumbling E optotypes 410e, 410f, 410g, 410h). Finally, with reference to bottom row of FIG. 14, it can be seen that these same four configurations of the Tumbling E can be displayed on the visual display device 404 in an even smaller overall size (e.g., Tumbling E optotypes 410i, 410j, 410k, 410l).

Figure 13:
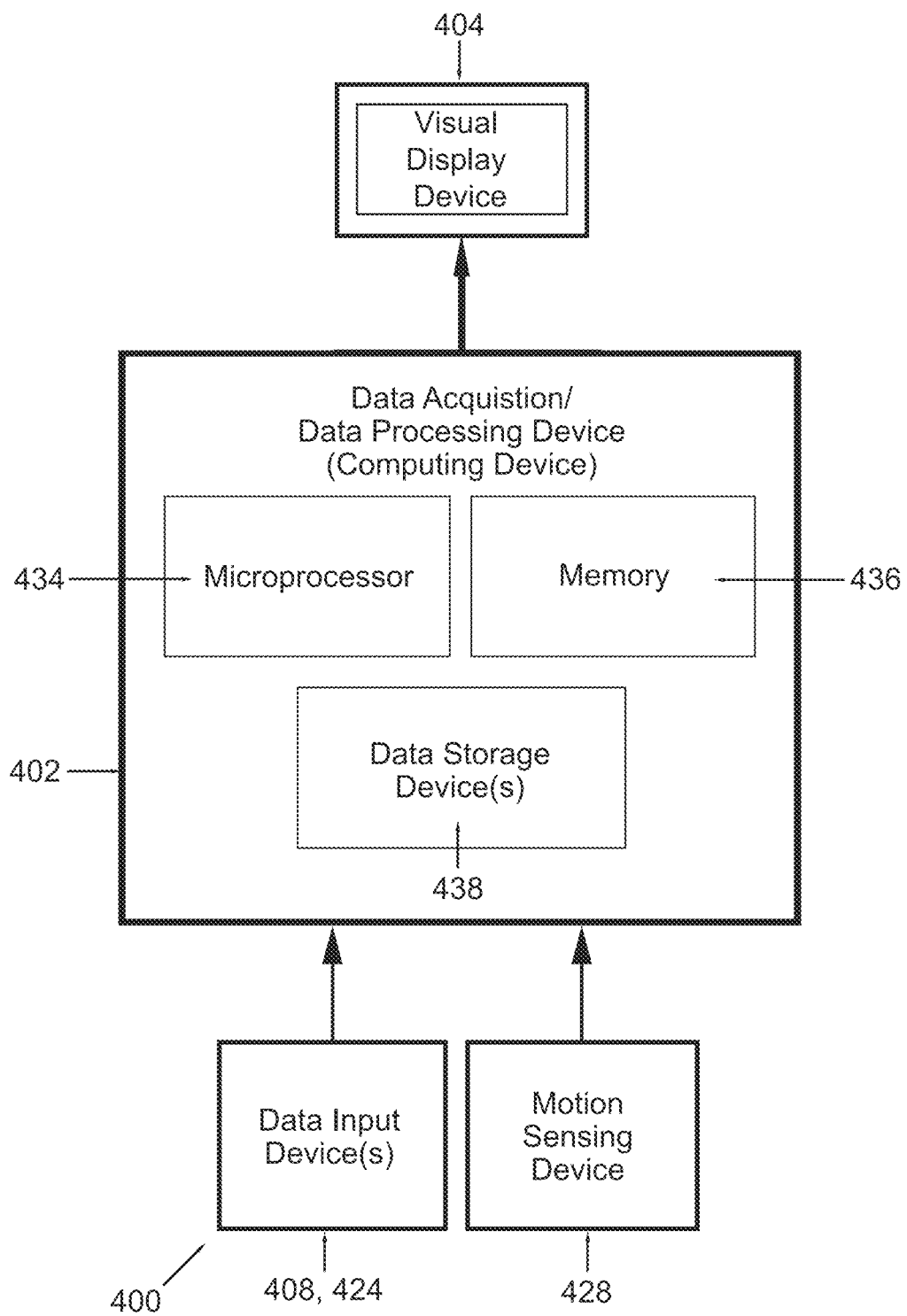
FIG. 13 is a block diagram of constituent components that may be utilized in the embodiment of the vision testing system of FIG. 12.

Now, turning to FIG. 13, it can be seen that the data acquisition/data processing device (i.e., the computing device 402) of the illustrative vision testing system 400 comprises a microprocessor 434 for processing data, memory 436 (e.g., random access memory or RAM) for storing data during the processing thereof, and data storage device(s) 438, such as one or more hard drives, compact disk drives, floppy disk drives, flash drives, or any combination thereof. As shown in FIG. 13, the motion sensing device 428 and the visual display device 404 are operatively coupled to the computing device 402 such that data is capable of being transferred between these devices. Also, as illustrated in FIG. 13, a plurality of data input devices 408, 424, such as the wireless mouse 424, keyboard, and touchpad 408, are operatively coupled to the computing device 402 so that a user is able to enter data into the computing device 402. In some embodiments, the computing device may be in the form of a laptop computer (as shown in FIG. 12), while in other embodiments, the computing device may be embodied as a desktop computer.

Figure 16:
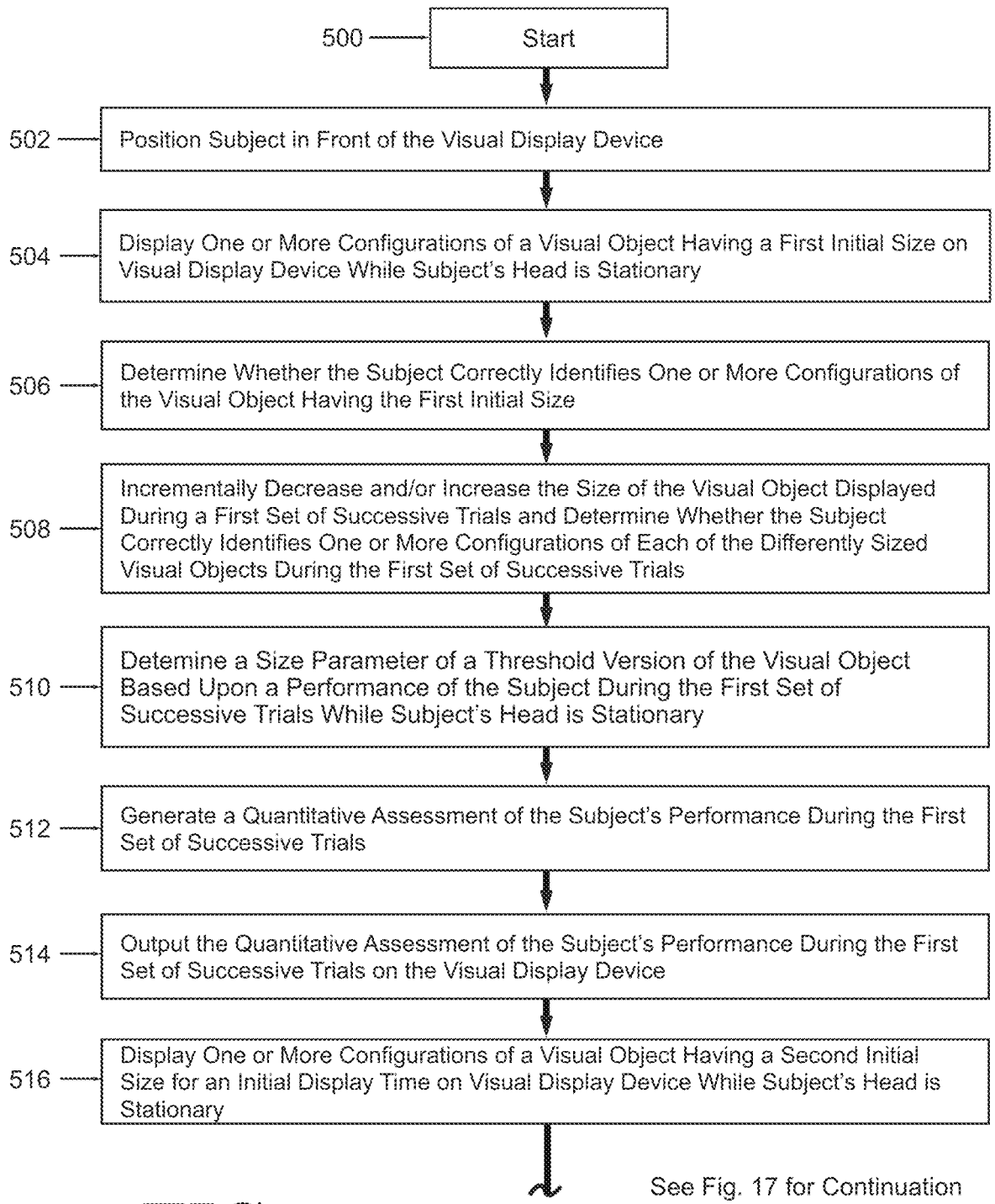
FIG. 16 is a partial flowchart illustrating a procedure for vision testing of a subject carried out by the system illustrated in FIG. 12, according to an embodiment of the invention.
Figure 17:
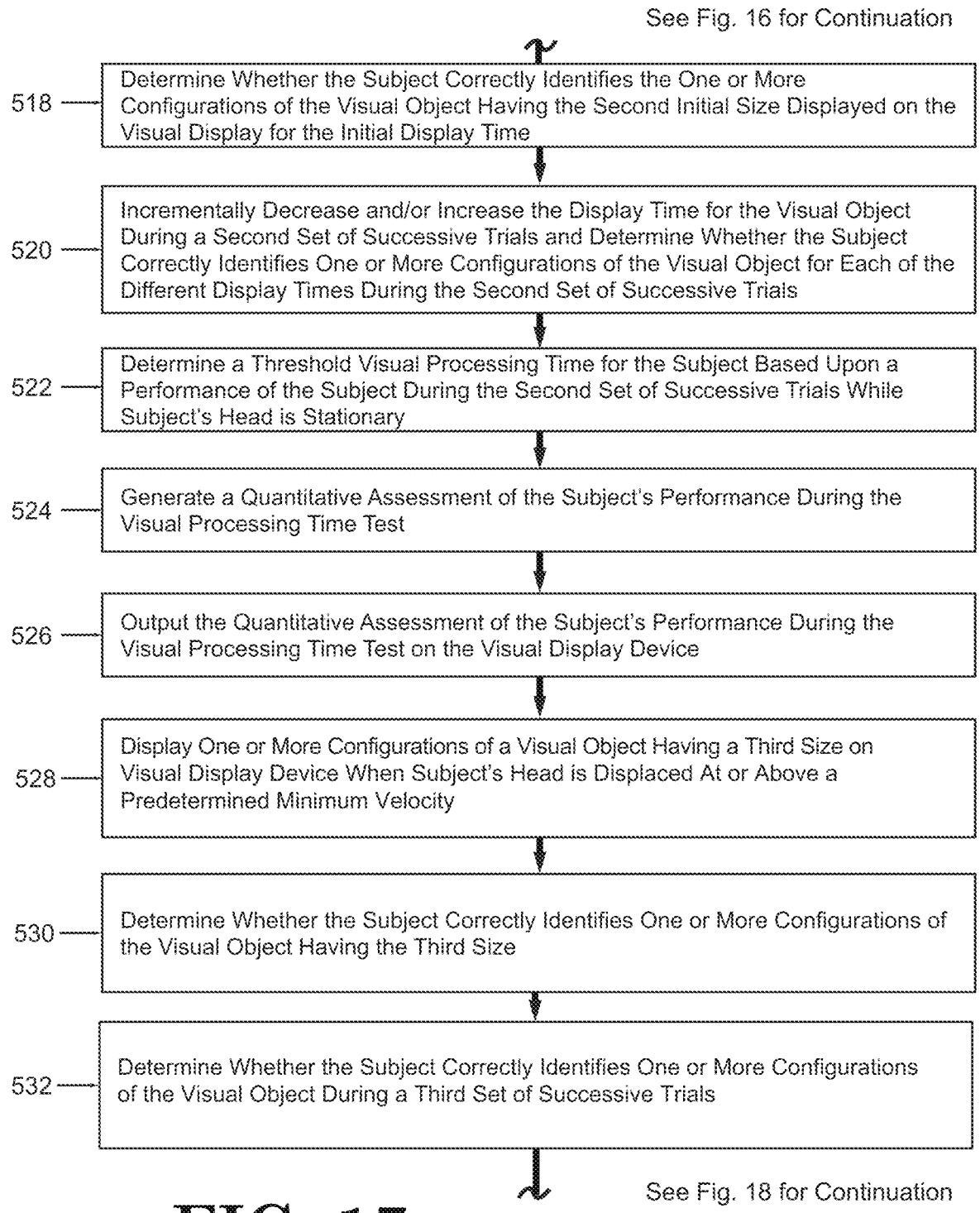
FIG. 17 is a continuation of the flowchart of FIG. 16, which illustrates additional steps of the procedure for vision testing of a subject, according to an embodiment of the invention.
Figure 18:
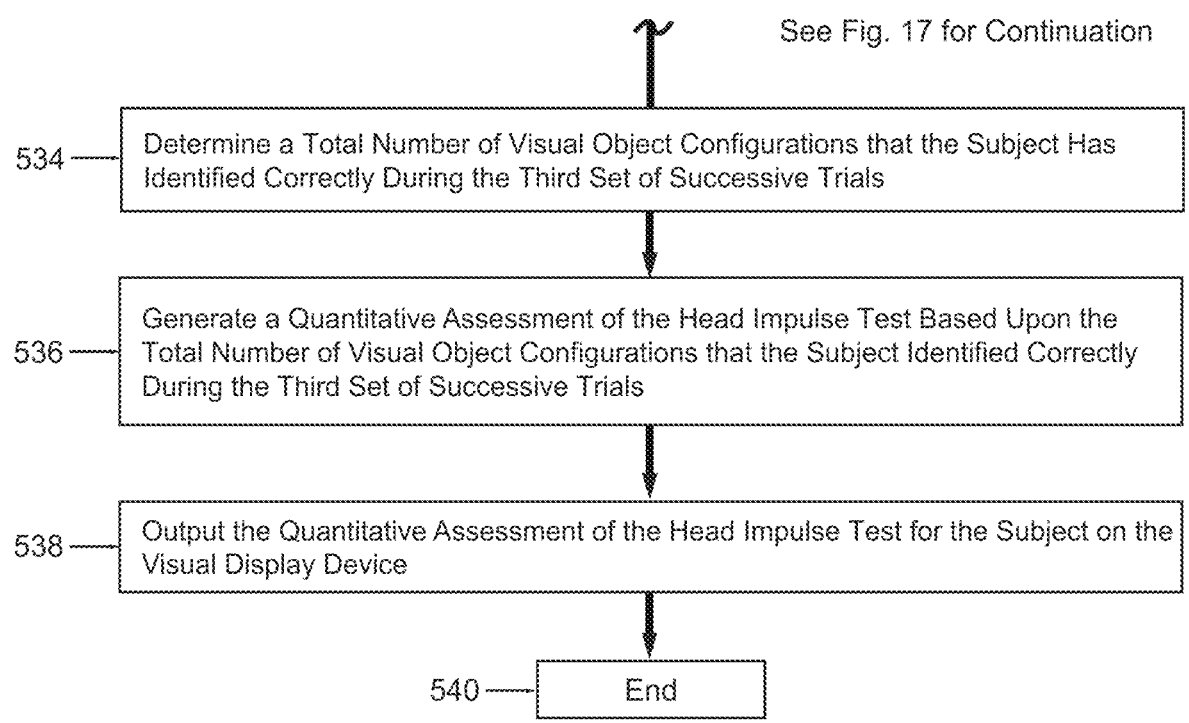
FIG. 18 is a continuation of the flowchart of FIG. 17, which illustrates yet additional steps of the procedure for vision testing of a subject, according to an embodiment of the invention.

In accordance with the illustrative embodiment of the invention, a flowchart illustrating a procedure for head impulse testing of a subject carried out by the system 400 is set forth in FIGS. 16-18. Referring initially to FIG. 16, the procedure commences at 500 (e.g., after the operator or clinician enters a start command to the computing device 402 by depressing a particular key on the keyboard), and in step 502, the subject is positioned in front of the output screen of the visual display device 404 such that a visual object 410 (e.g., an optotype) is visible to the subject 418. Then, while the subject 418 maintains a generally fixed position of his or her head 430 (i.e., keeping his or her head 430 as still as possible), one or more configurations of the visual object 410 having a first initial size are displayed on the output screen of the visual display device 404 in step 504. For example, referring to FIG. 14, one or more configurations 410*e*, 410*f*, 410*g*, 410*h* of the Tumbling E optotype may be displayed one-at-time on the output screen of the visual display device 404. In other exemplary embodiments, other suitable optotypes may be used in place of the Tumbling E, such as a Landolt C or letters of a recognized alphabet (e.g., the English alphabet). In one or more embodiments, the visual object (i.e., optotype) having the first initial size is displayed within approximately 500 milliseconds after the operator or clinician enters the start command to the computing device 402. The visual object (i.e., optotype) having the first initial size may be sufficiently large so that nearly all of the subjects tested will correctly identify the configuration of the first optotype that is displayed on the screen, and may be displayed for a time duration of approximately 500 milliseconds on the screen. After the visual object (i.e., optotype) disappears from the output screen of the visual display device 404, the computing device 402 may be specially programmed to implement a wait state, wherein the computing device 402 waits to record the subject's response.

Figure 19:
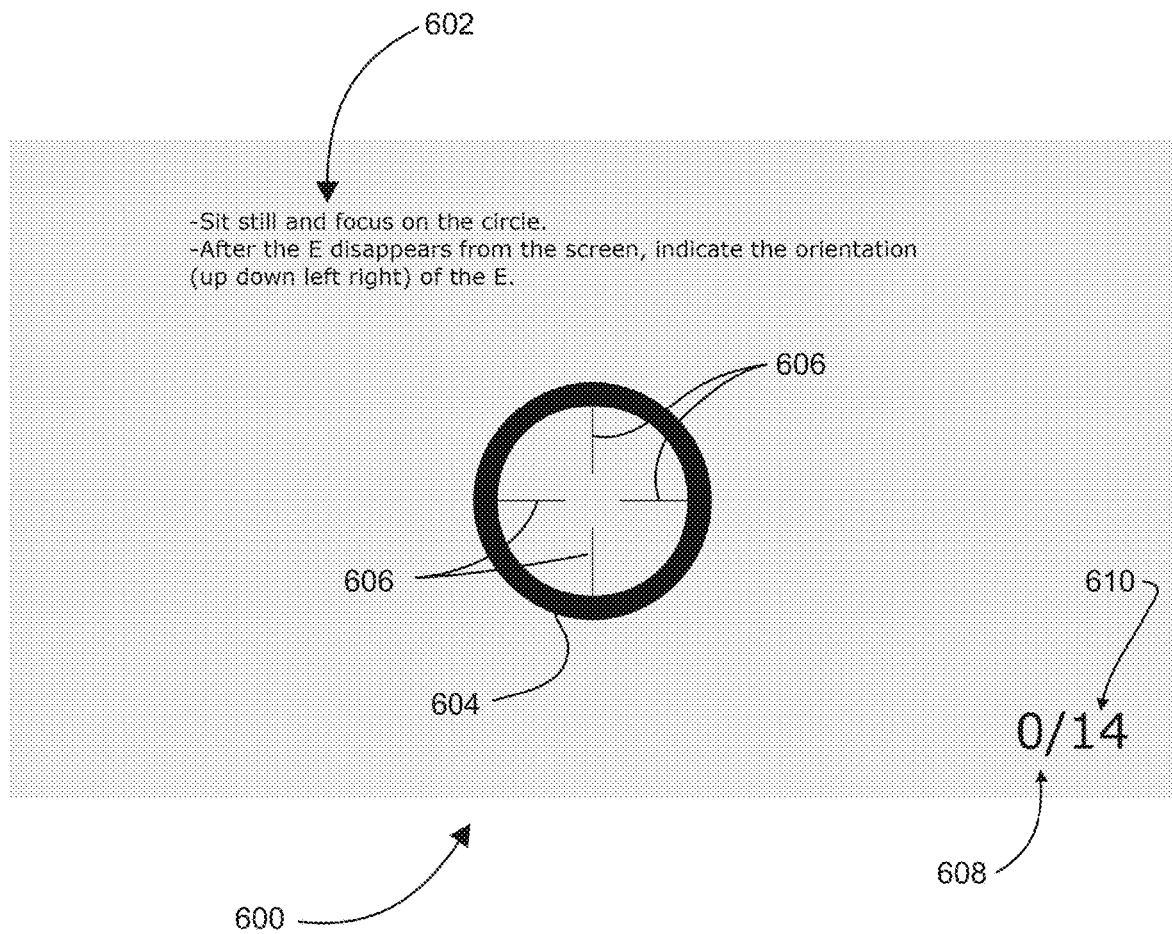
FIG. 19 is a subject screen image of the visual display device with an exemplary visual indicator that may be utilized during the performance of the vision test, according to an embodiment of the invention.
Figure 20:
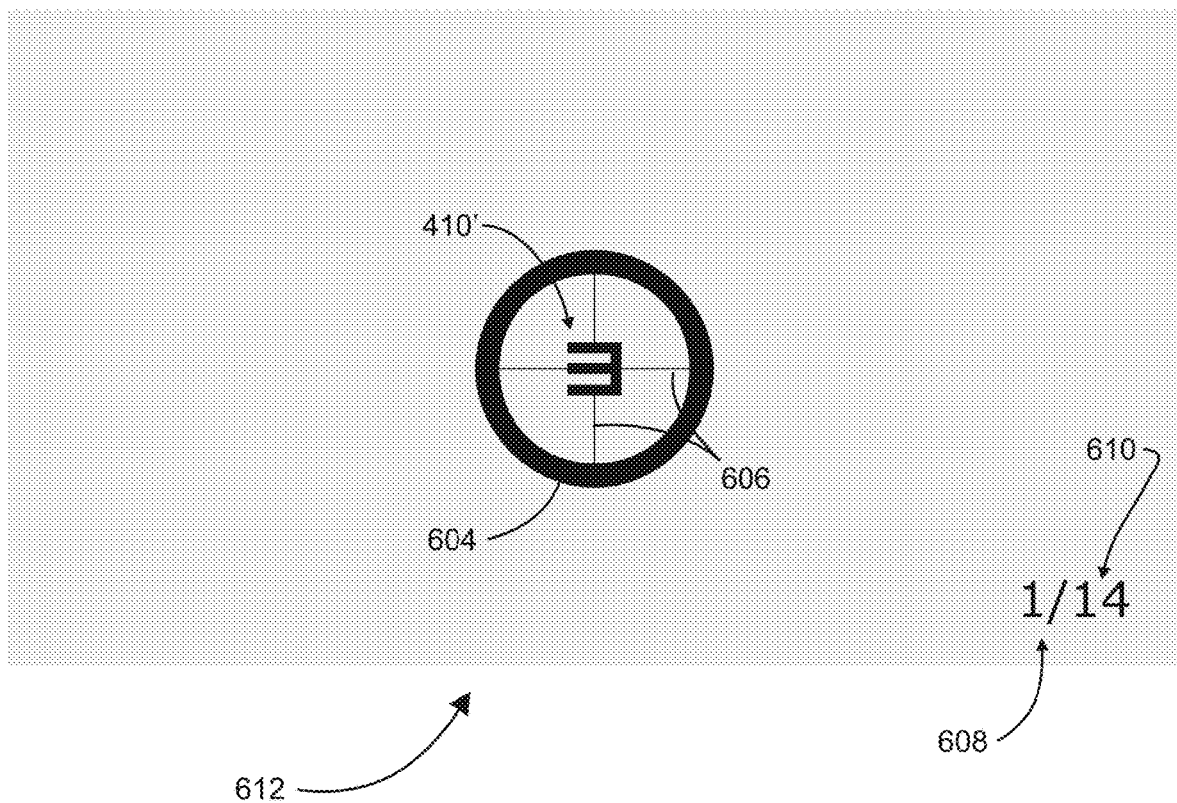
FIG. 20 is a subject test screen image of the visual display device prior to the performance a static visual acuity test or a visual processing time test, wherein the exemplary visual indicator is displayed together with the exemplary optotype, according to an embodiment of the invention.

With reference to FIGS. 19 and 20, exemplary subject screen images 600, 612, which may be displayed on the visual display device 404 during the first set of successive trials when the subject 418 maintains the generally fixed position of his or her head 430, will now be explained. Initially, referring to FIG. 19, it can be seen that a set of instructions 602 for the subject or patient may be displayed at the top of the screen image 600. The subject or patient instructions may specify that the manner in which the subject or patient is supposed to carry out the test (e.g., by instructing the patient to sit still and focus on the circle 604, and by instructing the patient to indicate the orientation of the optotype after it disappears from the screen). The set of instructions 602 may be initially displayed on the output screen by the computing device 402, and then subsequently hid from view (i.e., suppressed thereafter) so as not to unnecessarily distract the subject 418 during the testing. As additionally shown in FIG. 19, a solid black circle 604 is displayed in the approximate center of the screen. The solid black circle 604 comprises a plurality of crosshairs 606 disposed therein (e.g., spaced 90 degrees apart from one another, and disposed at 0 degrees, 90 degrees, 180 degrees, and 360 degrees), and extending inwardly towards the center of the circle 604. Referring again to FIG. 19, it can be seen that, in the bottom right-hand corner of the screen, the number of trials 608 completed thus far, together with the maximum number of trials 610 that may be completed during the first set of successive trials is displayed. Because FIG. 19 depicts the starting screen image 600 for the first set of successive trials (i.e., when the subject's head is stationary), the number 608 is zero (0) in FIG. 19. In this illustrative embodiment, the maximum number of trials 610 performed in conjunction with the first set of successive trials is fourteen (14). However, it is to be understood that, in other embodiments of the invention, the maximum number of trials 610 performed in conjunction with the first set of successive trials may be higher or lower than fourteen (14). Also, in an alternative embodiment, a small box with the optotype size and a small box with the optotype display time may be placed in the bottom right-hand corner of the screen 600, rather than the number of trials 608 completed thus far, and the maximum number of trials 610. In this alternative embodiment, the number of trials 608 completed thus far, and the maximum number of trials 610 may be placed in test summary data on the operator or clinician screen. Turning to FIG. 20, it can be seen that the screen image 612 is generally the same as the screen image 600 of FIG. 19, except that an optotype 410' is displayed in the center of the circle 604. While a Tumbling E optotype is utilized in the illustrative embodiment of FIG. 20, it is to be understood that, in an alternative embodiment, a Landolt C optotype or another type of optotype may be used in place of the Tumbling E optotype. In the exemplary screen image 612 of FIG. 20, it can be seen that the optotype is pointing to the left, so a correct identification of the optotype by the subject or patient would require that he or she indicates that the optotype is pointing to the left. In addition, as depicted in FIG. 20, the number of trials 608 is equal to one (1) in order to indicate that the subject or patient has completed one trial of the first set of successive trials (i.e., when the subject's head is stationary).

The circle 604 depicted in FIGS. 19 and 20, which is generated by the computing device 402, is large enough to fit the largest size optotype that will be displayed to the subject or patient during the static testing. The crosshairs 606 extend inward in order to prevent the circle 604 from needing to change size. Advantageously, in order to avoid becoming a distraction to the subject during the testing, the size of the circle 604 remains constant (i.e., it is static). Because the size of the circle 604 is constant during the testing, it must be large enough to accommodate the largest optotype that will be displayed to the subject during the testing. Consequently, this results in a circle 604 that is significantly larger than the smallest sized optotypes displayed during the testing, which in turn, makes it difficult for the subject to tell where the small sized optotypes will appear on the screen. The subject's ability to find the optotype on the screen is not something that it is desired to be factored into the testing. Thus, the crosshairs 606 are provided within the circle 604 in order to help direct the gaze of the subject or patient during the display of the optotype, especially that of a small optotype. Like the circle 604, the crosshairs 606 are static during the testing (i.e., they do not undergo changes in size or shape) so as not to distract the subject during the testing. Also, as best shown in FIG. 19, the crosshairs 606 do not extend all the way to the center of the circle 604 so as to prevent them from interfering with the display of the small optotypes. In addition, both the circle 604 and the crosshairs 606 remain on the output screen of the visual display device throughout the duration of the testing.

Now, turning again to FIG. 16, in step 506, the computing device or data processing device 402 determines whether or not the subject 418 correctly identifies one or more configurations (e.g., 410*e*, 410*f*, 410*g*, 410*h*) of the visual object 410 having the first initial size. For example, the subject 418 may be presented with one or more optotypes having the first initial size (e.g. a single optotype 410*g* pointing down). This optotype 410*g* is of the first initial size, which may be a size scale factor of 0.75. After the optotype is displayed to the subject 418, the subject 418 may utilize a user input device 424 (e.g., a wireless mouse) in order to transmit the response of the subject 418 to the computing device 402 (e.g., the wireless mouse may have four buttons, each of which corresponds to one of the four configurations of the optotype). Alternatively, the response of the subject 418 may be entered using the keyboard of the computing device 402 by using the directional arrows and space bar on the keyboard. For example, the "up" arrow key on the keyboard is used to record an optotype pointing up, the "down" arrow key on the keyboard is used to record an optotype pointing down, the "left" arrow key on the keyboard is used to record an optotype pointing to the left, the "right" arrow key on the keyboard is used to record an optotype pointing to the right, and the spacebar is used to record an unknown orientation of the optotype. If the spacebar is depressed on the keyboard, the computing device 402 randomly chooses the response of the subject 418. After receiving the subject's response, the computing device 402 is specially programmed to determine if the subject correctly determined the configuration of the optotype that was displayed on the output screen of the visual display device 404. For example, if the optotype 410*g* of FIG. 14 was displayed on the screen, the subject 418 must indicate that optotype is pointing down to get the identification correct. Any other answer would be incorrect for this configuration of the optotype. Once the subject's answer or response is evaluated as to its correctness, the computing device 402 is specially programmed to record whether or not the subject 418 identified the optotype correctly. In one exemplary embodiment, if the subject 418 identifies the configuration of the optotype 410*g* correctly, the computing device 402 is specially programmed to display one or more optotypes having a physical size that is smaller than the first optotype (e.g., the second trial may comprise one or more optotypes that have a size scale factor of 0.6875). For example, the second optotype may comprise the optotype 410*j* in FIG. 14, which has a smaller size than the optotype 410*g* in the middle row of FIG. 14. Conversely, if the subject 418 identifies the configuration of the first optotype 410*g* incorrectly, the computing device 402 is specially programmed to display one or more optotypes having a physical size that is larger than the first optotype (e.g., the second optotype may have a size scale factor of 1.0). For example, in this case, the second optotype may comprise the optotype 410*c* in the top row of FIG. 14, which has a larger size than the optotype 410*g* in the middle row of FIG. 14. In one or more embodiments, as described hereinafter, the computing device 402 is specially programed to execute a parameter estimation algorithm in order to determine the physical size of the successive optotype that is displayed on the output screen of the visual display device 404. Also, in one or more embodiments, the computing device 402 is specially programmed to display the successive optotype on the screen approximately five-hundred (500) seconds after it receives the subject's response regarding the preceding optotype.

In this manner, as specified in step 508 of FIG. 16, the computing device 402 is specially programmed to incrementally decrease or increase the size of the visual object on the output screen of the visual display device 404 during a first set of successive trials (e.g., during a maximum number 610 of fourteen (14) trials as indicated in FIGS. 19 and 20). For example, if the subject identifies the configuration of a particular-sized optotype correctly, the optotype size of the next optotype displayed on the screen is generally decreased, while the optotype size of the next optotype displayed on the screen is generally increased if the subject fails to identify the configuration of the optotype correctly. In the exemplary embodiment, after each optotype is displayed on the output screen of the visual display device 404, the computing device 402 is specifically programmed to determine whether or not the subject 418 correctly identified the configuration of the optotype.

In one or more embodiments, the size of the visual object presented to the subject 418 during the first set of successive trials generally changes with each successive trial (e.g., the subject 418 does not receive five (5) optotypes of the same size in consecutive order during the testing). In contrast to the static visual acuity testing, the size of the visual object presented to the subject 418 during the head impulse test trials, as described hereinafter, remains constant during each successive trial (e.g., the subject 418 receives optotypes of the same size during the head impulse testing).

In step 510 of FIG. 16, after the subject 418 has completed a predetermined number of trials of optotype identification, the computing device 402 is specifically programmed to determine a size parameter (e.g., a size scale factor) of a first threshold version of the optotype based upon the performance of the subject 418 during the first set of successive trials during which the subject 418 maintained the generally fixed position of his or her head 430. For example, after a particular end condition is reached, the computing device 402 determines that the first threshold version of the optotype has a size scale factor of 0.40. In one embodiment, the size scale factor of the first threshold version of the optotype is a calculated value that is determined using one or more statistical equations or formulas (e.g., using a parameter estimation algorithm as described hereinafter).

The computing device 402 may be specifically programmed with multiple end conditions for determining when to end the first set of successive trials. For example, the computing device 402 may automatically stop the first set of successive trials as soon as any one or combination of the following conditions occur: (i) the subject has completed a total of fourteen (14) trials of optotype identification (i.e., a maximum allowable number of trials is reached), (ii) a predetermined number of reversals has occurred, or (iii) the user has stopped the first set of successive trials (e.g., the operator or clinician initiates the cessation of the successive trials by depressing a particular key on the keyboard).

In one or more embodiments, the computing device 402 may be specially programmed to automatically stop the first set of successive trials when both the computed number of reversals for the test series has exceeded the predetermined number of reversals and the computed number of trials for the test series has exceeded the predetermined number of trials. Initially, the manner in which the total number of reversals is calculated by the computing device 402 will be explained. During the vision testing, a reversal is determined in accordance with the following equation:

$$\text{diff} = [y(i-1) - y(i)] * [y(i) - y(i+1)] \tag{6}$$

where:
diff: product of the slope before and after a stimulus point;
y(i): stimulus value at trial number i;
y(i−1): stimulus value for the trial preceding trial number i;
y(i+1): stimulus value for the trial following trial number i;
i: trial number for which the reversal is being determined.
After computing the difference value determined using equation (6) for a given trial number, if it is determined by the computing device 402 that the difference value is less than or equal to zero, then the reversal counter is incremented using the following equation:

$$\text{rev} = \text{rev} + 1 \tag{7}$$

That is, the reversal number counter is incremented by one. Conversely, if it is determined by the computing device 402 that the difference value is greater than zero, then the reversal counter is not incremented and the number of reversals stays the same. Also, if the computed difference value is less than or equal to zero, and thus the reversal counter is incremented, the computing device 402 may be specially programmed to next determine if the total computed number of reversals is greater than or equal to the predetermined number of reversals that has been set (e.g., a total number of eight (8) reversals). After which, the computing device 402 may be specially programmed to further determine if the total number of trials that have been completed (value of i) is greater than or equal to a predetermined number of trials (e.g., fourteen (14) trials of optotype identification). When both the total computed number of reversals is greater than or equal to the predetermined number of reversals (e.g., eight (8) reversals), and the total number of trials that have been completed is greater than or equal to the predetermined number of trials (e.g., fourteen (14) trials), then the computing device 402 may be specially programmed to automatically stop the first set of successive trials of the vision testing. It is to be understood that the abovedescribed procedure may be used to determine the stopping point of the visual processing time, and head impulse test series of successive trials as well.

Then, in step 512 of FIG. 16, the computing device 402 is specifically programmed to generate a quantitative assessment of the subject's performance during the first set of successive trials, and finally, in step 514 of FIG. 16, to output the quantitative assessment of the subject's performance during the first set of successive trials on the output screen of the visual display device 404. For example, in an exemplary embodiment, the computing device 402 may generate a report in order to display the test results from the first set of successive trials.

After determining the size parameter of the first threshold version of the optotype in step 510 above, and generating and displaying the quantitative results in steps 512 and 514, the visual processing time of the subject 418 may be determined by the computing device 402 in steps 516-522 of FIGS. 16 and 17. The purpose of this test is to determine how long the optotype needs to be displayed on the screen of the visual display device 404 in order for the subject 418 to comprehend the displayed orientation of the optotype Like the first set of successive trials described above, the visual processing time test is a static-type test, so there are no head movements made by the subject or patient during the performance of the visual processing time test. The size scale factor of the first threshold version of the optotype (e.g., in units of logMAR or relative logMAR) that was determined in conjunction with the first set of successive trials described above is used by the visual processing time test. In particular, the optotype size during the performance of the visual processing time test is determined by increasing the optotype size determined in conjunction with the first set of successive trials by two sizes (e.g., by 0.2 logMAR). This optotype size remains constant for all trials of the visual processing time test. The variable in the visual processing time test is the time duration during which the optotype is displayed on the screen. The stimulus level (i.e., selected display time of the optotype on the screen) may be determined by the computing device 402 using the same parameter estimation algorithm that selects the optotype size in the first set of successive trials described above.

In one or more exemplary embodiments, during the visual processing time test, the shortest amount of time that the optotype is displayed on the screen of the visual display device 404 is twenty (20) milliseconds (i.e., because of the monitor refresh rate), while the maximum amount of time that the optotype is displayed on the screen of the visual display device 404 is seventy (70) milliseconds. The upper limit of seventy (70) milliseconds was selected because, if the subject or patient has a visual processing time greater than 70 milliseconds he or she will be unable to complete the dynamic trials of the head impulse test. An individual with a visual processing time greater than 70 milliseconds would be unable to complete these dynamic trials because the optotype must be displayed on the visual display device 404 while the head of the subject or patient is being displaced. If the display time of the optotype needed to be much longer than 70 milliseconds, it would not be possible to display the optotype only during the subject's head movement, and conversely, to not display it when the subject's head is at maximum amplitude and head velocity is zero (0).

In one or more embodiments, the computing device 402 may be specially programmed to prompt the operator or clinician to input the step change (i.e., resolution) in the visual processing time between trials. The default test setting for the resolution may be ten (10) milliseconds, while the computing device 402 may be specially programmed to accept a resolution range between ten (10) milliseconds and fifty (50) milliseconds, inclusive.

After the operator or clinician enters a start command to the computing device 402 by depressing a particular key on the keyboard, the visual processing time test begins. Turning again to the flowchart of FIG. 16, it can be seen in step 516 that, while the subject 418 maintains a generally fixed position of his or her head 430 (i.e., keeping his or her head 430 as still as possible), one or more configurations of the visual object 410 are displayed on the output screen of the visual display device 404 for an initial display time (e.g., the optotype is displayed for ninety (90) milliseconds on the screen). For example, referring to FIG. 14, one or more configurations 410a, 410b, 410c, 410d of the Tumbling E optotype may be displayed one-at-time on the output screen of the visual display device 404 for an initial display time. In an alternative exemplary embodiment, one or more configurations of a Landolt C optotype may be displayed one-at-time on the output screen of the visual display device 404 for an initial display time. In other exemplary embodiments, other suitable optotypes may be used in place of the Tumbling E or Landolt C, such as letters of a recognized alphabet (e.g., the English alphabet). In one or more embodiments, the visual object 410 (i.e., optotype) is displayed in approximately 500 milliseconds after the operator or clinician enters the start command to the computing device 402. After the visual object (i.e., optotype) disappears from the output screen of the visual display device 404, the computing device 402 may be specially programmed to implement a wait state, wherein the computing device 402 waits for the subject or clinician to record the subject's response.

During the visual processing time test, the same solid black circle 604 and crosshairs 606, which was described above in conjunction with FIGS. 19 and 20, is used to present the optotype to the subject 418. That is, the patient screen during the visual processing time test is generally the same as the screen images 600, 612 in FIGS. 19 and 20.

Now, with reference to FIG. 17, in step 518, the computing device or data processing device 402 determines whether or not the subject 418 correctly identifies the one or more configurations (e.g., 410a, 410b, 410c, 410d) of the visual object 410 that is displayed on the visual display device 404 for the initial display time. For example, the subject 418 may be presented with a single optotype 410b pointing down (see FIG. 14). After the optotype is displayed to the subject 418, the subject 418 or the clinician 414 may utilize a user input device 424 (e.g., a wireless mouse) in order to transmit the response of the subject 418 to the computing device 402 (e.g., the wireless mouse may have four buttons, each of which corresponds to one of the four configurations of the optotype). Alternatively, the response of the subject 418 may be entered using the keyboard of the computing device 402 by using the directional arrows and space bar on the keyboard. For example, the "up" arrow key on the keyboard is used to record an optotype pointing up, the "down" arrow key on the keyboard is used to record an optotype pointing down, the "left" arrow key on the keyboard is used to record an optotype pointing to the left, the "right" arrow key on the keyboard is used to record an optotype pointing to the right, and the spacebar is used to record an unknown orientation of the optotype. If the space bar is depressed on the keyboard, the computing device 402 randomly chooses the response of the subject 418. After receiving the subject's response, the computing device 402 is specially programmed to determine if the subject correctly determined the configuration of the optotype that was displayed on the output screen of the visual display device 404. For example, if the optotype 410*b* of FIG. 14 was displayed on the screen, the subject 418 must indicate that optotype is pointing down to get the identification correct. Any other answer would be incorrect for this configuration of the optotype. Once the subject's answer or response is evaluated as to its correctness, the computing device 402 is specially programmed to record whether or not the subject 418 identified the optotype correctly. In one exemplary embodiment, if the subject 418 identifies the configuration of the optotype 410*b* correctly, the computing device 402 is specially programmed to display one or more subsequent optotypes for a display time that is shorter than the initial display time (e.g., the second trial may display the subsequent optotype on the screen for a display time of only 50 milliseconds, rather than the 60 milliseconds that was used during the initial trial). Conversely, if the subject 418 identifies the configuration of the first optotype 410*b* incorrectly, the computing device 402 is specially programmed to display one or more subsequent optotypes for a display time that is longer than the initial display time (e.g., the second trial may display the subsequent optotype on the screen for a display time of 70 milliseconds, rather than the 60 milliseconds that was used during the initial trial). Also, in one or more embodiments, the computing device 402 is specially programmed to display the successive optotype on the screen approximately five-hundred (500) milliseconds after it receives the subject's response regarding the preceding optotype.

In this manner, as specified in step 520 of FIG. 17, the computing device 402 is specially programmed to incrementally decrease or increase the display time for the visual object on the output screen of the visual display device 404 during a set of successive trials (e.g., during a maximum number 610 of fourteen (14) trials as indicated in FIGS. 19 and 20). During the set of successive trials, various configurations of the same-sized visual object may be displayed on the output screen of the visual display device 404 for identification by the subject. For example, if the subject identifies a configuration of the same-sized optotype correctly, the screen display time for next-displayed optotype is generally decreased, while the screen display time for next-displayed optotype is generally increased if the subject fails to correctly identify the configuration of the optotype correctly. In the exemplary embodiment, after each optotype is displayed on the output screen of the visual display device 404 for a particular display time, the computing device 402 is specifically programmed to determine whether or not the subject 418 correctly identified the configuration of the optotype. In step 522 of FIG. 17, after the subject 418 has completed a predetermined number of trials of optotype identification, the computing device 402 is specifically programmed to determine a threshold visual processing time for the subject 418 based upon the performance of the subject 418 during the set of successive trials during which the subject 418 maintained the generally fixed position of his or her head 430. For example, after a particular end condition is reached, the computing device 402 determines that the visual processing time for the subject 418 is fifty-five (55) milliseconds. In one embodiment, the visual processing time for the subject 418 is a calculated value that is determined using one or more statistical equations or formulas (e.g., using a parameter estimation algorithm as described hereinafter).

As described above for the first set of successive trials, the computing device 402 may be specifically programmed with multiple end conditions for determining when to end the second set of successive trials. For example, the computing device 402 may automatically stop the second set of successive trials as soon as any one or combination of the following conditions occur: (i) the subject has completed a total of fourteen (14) trials of optotype identification (i.e., a maximum allowable number of trials is reached), (ii) a predetermined number of reversals has occurred (refer to explanation above), or (iii) the user has stopped the first set of successive trials (e.g., the operator or clinician initiates the cessation of the successive trials by depressing a particular key on the keyboard).

Then, in step 524 of FIG. 17, the computing device 402 is specifically programmed to generate a quantitative assessment of the subject's performance during the visual processing time test, and finally, in step 526 of FIG. 17, to output the quantitative assessment of the subject's performance during the visual processing time test on the output screen of the visual display device 404. For example, in an exemplary embodiment, the computing device 402 may generate a report in order to display the test results from the visual processing time test.

Figure 21:
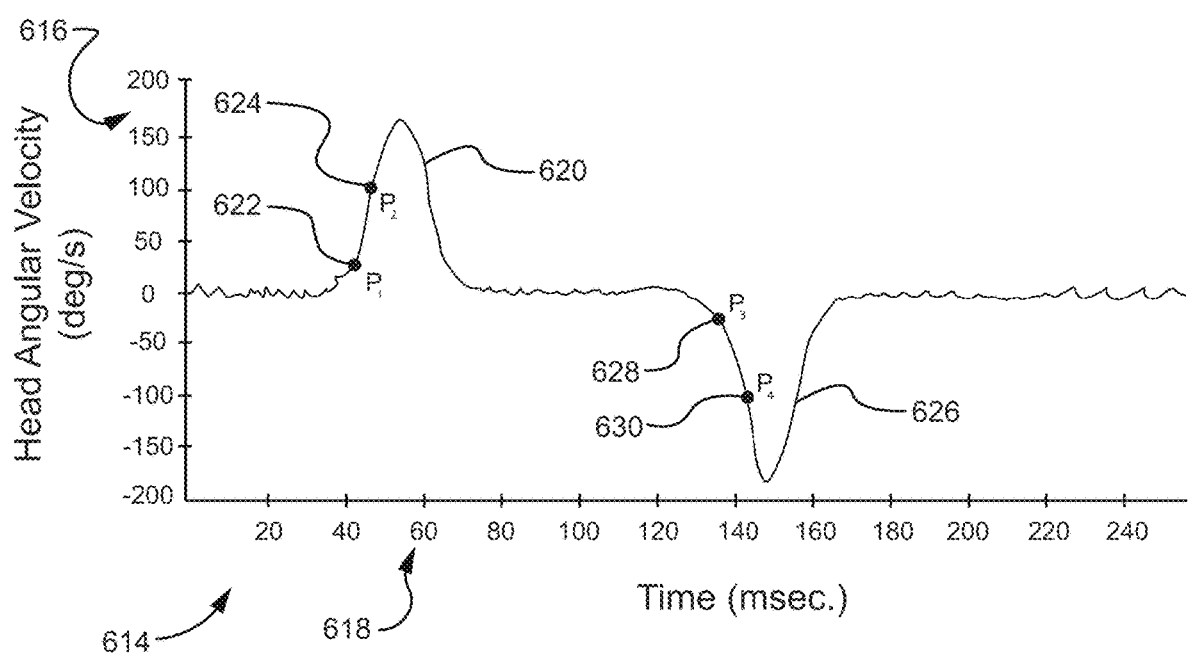
FIG. 21 is a graph illustrating a head angular velocity curve generated during the performance of a head impulse test, according to an embodiment of the invention.

Referring again to FIG. 17, the dynamic portion of the head impulse test will be explained in detail. Initially, in step 528 of FIG. 17, when the subject's head 430 is displaced at or above a predetermined minimum velocity or speed (e.g., at or above 100 degrees per second) as measured by the motion sensing device 428, one or more configurations of the optotype 410 having a third size are displayed in succession on the output screen of the visual display device 404. In one or more embodiments, the optotype of step 528 has a third size that is greater than the size of the threshold version of the optotype determined in step 510. In these embodiments, the size of the threshold version of the optotype determined in step 510 may be multiplied by a scale factor (e.g., 1.5 or 1.75) to arrive at the third size (i.e., the increased size) of the optotype to be used in step 528. For example, in one or more embodiments, an optotype size that is two lines above the optotype size determined in step 510 on a Tumbling E eye chart may be used for the head impulse test. In other words, in one or more embodiments, the optotype size during the performance of the dynamic portion of the head impulse test is determined by increasing the optotype size determined in conjunction with the first set of successive trials by two sizes (e.g., by adding 0.2 logMAR to the static visual acuity determined during the first set of successive trials). During step 528, different configurations of the tumbling E optotype having the third size may be displayed one-at-time on the output screen of the visual display device 404. In the illustrative embodiment, the subject's head 430 may be displaced by the clinician 414 abruptly rotating the subject's to the right, or to the left, about the yaw axis 466 of FIG. 15 (i.e., approximately in a horizontal plane). For example, during one trial, the clinician 414 may rotate the subject's head 430 to the right about the yaw axis 466 between −20 degrees and 20 degrees (i.e., between 20 degrees to the left and 20 degrees to the right). Then, in the next trial, the clinician 414 may rotate the subject's head 430 to the left about the yaw axis 466 between 20 degrees and −20 degrees (i.e., between 20 degrees to the right and 20 degrees to the left). However, during the trials of the head impulse test, it is to be understood that the clinician 414 may randomly vary the rotation of the subject's head 430 between right and left rotations (i.e., the clinician 414 does not always alternate between right and left rotation, but rather may successively rotate in the same direction during consecutive trials). In the illustrative embodiment, the optotype 410 is displayed on the output screen of the visual display device 404 when the angular velocity of the head 430 of the subject 418 meets or exceeds a predetermined minimum angular velocity. For example, an exemplary head angular velocity curve 620, 626 generated during the performance of a head impulse test is illustrated in the graph 614 of FIG. 21. As shown in this figure, the y-axis 616 of the graph 614 is the head angular velocity in degrees per second, while the x-axis 618 of the graph 614 is the time in milliseconds (msec). In the graph 614 of FIG. 21, it can be seen that the head angular velocity curve 620, 626 has a first portion 620 where the head of the subject 418 is being rotated in a first direction (e.g., to the right) and a second portion 626 where the head of the subject 418 is being rotated in a second direction (e.g., to the left). In the first portion 620 of the head angular velocity curve 620, 626 for head rotation to the right, the computing device 402 initially determines when the head angular velocity reaches a first value 622. Once the computing device 402 has determined that the head angular velocity has reached the first value 622, the computing device 402 concludes that head 430 of the subject 418 is undergoing a head impulse displacement. The initial determination that the first threshold value 622 has been reached enables the computing device 402 to differentiate between mere noise in the head angular velocity signal measured the inertial measurement unit 428, and the actual occurrence of a head impulse displacement. Upon determining that the first threshold value 622 has been reached, the computing device 402 next determines when the head angular velocity reaches a second value 624 in the first portion 620 of the head angular velocity curve 620, 626 (i.e., the second value 624 is the minimum angular velocity for optotype display). Once the computing device 402 has determined that the head angular velocity has reached the second value 624, the computing device 402 displays the optotype 410 on the output screen of the visual display device 404. Referring again to FIG. 21, it can be seen that these same two threshold values 628, 630 are determined by the computing device 402 for the left head rotation in the second portion 626 of the head angular velocity curve 620, 626.

Also, during the dynamic portion of the head impulse test, the computing device 402 may be specially programmed to randomly choose the orientation of the optotype that is displayed on the screen. After the optotype disappears during the dynamic portion of the head impulse test, the subject 418 enters an optotype orientation response (i.e., the perceived configuration of the visual object 410) into the user input device 424, which transmits the response to the laptop computing device 402.

Figure 15:
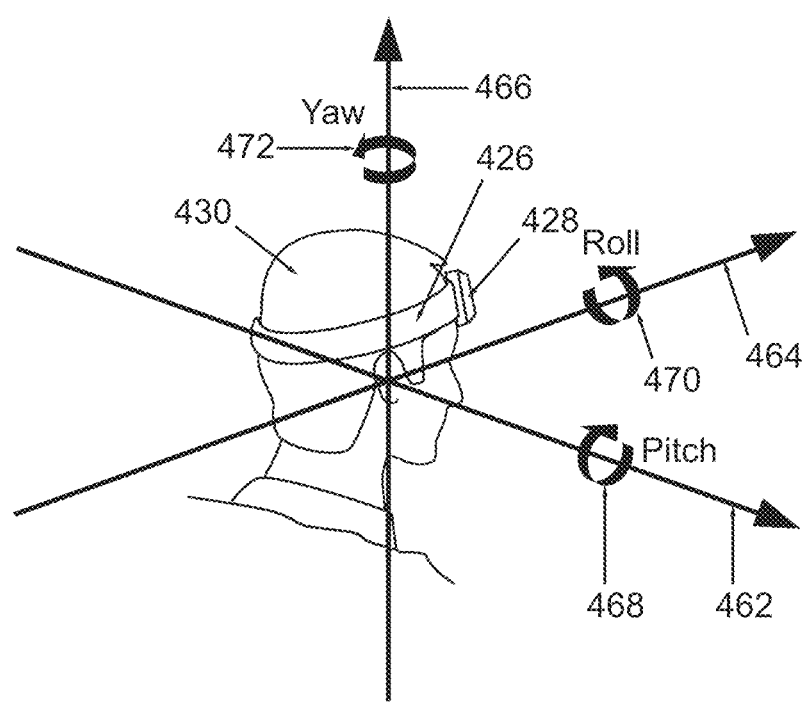
FIG. 15 is a diagrammatic view of the directions of subject head rotation that are capable of being measured with the motion sensing device of the vision testing systems described herein.

In alternative exemplary embodiments, rather than rotating the head 430 of the subject 418 about the yaw axis 466 in FIG. 15, the clinician 414 may alternatively rotate the head 430 of the subject 418 about the pitch axis 462 (i.e., approximately in a vertical plane) or about the roll axis 464 (i.e., in a roll plane). The computing device 402 is specially programmed to allow the clinician 414 to selectively choose any one of these rotational directions when performing the dynamic portion of the head impulse test.

Referring again to the flowchart of FIG. 17, the computing device or data processing device 402 determines whether or not the subject 418 correctly identifies one or more configurations (e.g., 410*a*, 410*b*, 410*c*, 410*d*) of the visual object 410 having the third size in step 530. For example, the subject 418 may be presented with one or more optotypes having the third size (e.g., a single optotype 410*a* pointing up). In the illustrative embodiment, during the dynamic set of trials performed during the head impulse test, each of the optotypes has the same physical size (i.e., each optotype has the same increased third size that is determined based upon the threshold size computed for the first series of trials carried out in steps 500-510 above). After each optotype in the trial is displayed to the subject 418, the subject 418 may utilize the user input device 424 (e.g., a wireless mouse) in order to transmit his or her response to the computing device 402 (e.g., the wireless mouse may have four buttons, each of which corresponds to one of the four configurations of the optotype). After receiving each of the subject's responses, the computing device 402 is specially programmed to determine if the subject 418 correctly determined the configuration of the optotype that was displayed on the output screen of the visual display device 404. For example, if the optotype 410*a* of FIG. 14 was displayed on the screen, the subject 418 must indicate that the optotype is pointing up to get the identification correct. Any other answer would be incorrect for this configuration of the optotype. Once the subject's answer or response is evaluated as to its correctness, the computing device 402 is specially programmed to record whether or not the subject 418 identified the optotype correctly.

In this manner, as set forth in step 532 of FIG. 17, the computing device 402 is specially programmed to determine whether or not the subject 418 correctly identified the configuration of the optotype 410 during a third set of successive trials (i.e., during the dynamic set of trials of the head impulse test). During the third set of successive trials, the angular velocity or speed of the head 430 of the subject 418 is measured by the motion sensing device 428 as the clinician 414 abruptly rotates the subject's to the right, or to the left, about the yaw axis 466 of FIG. 15 during a predetermined maximum number of trials (e.g., during fourteen (14) trials).

In step 534 of FIG. 18, after the subject 418 has completed a predetermined number of trials of optotype identification (e.g., fourteen (14) total trials), the computing device 402 is specifically programmed to determine the total number of visual object configurations (e.g., optotype configurations) that the subject 418 has identified correctly during the dynamic portion of the head impulse test (i.e., during the third set of successive trials). As an example, after the subject 418 completes one such series of trials of optotype identification, the computing device 402 may determine that the subject correctly identified nine (9) out of fourteen (14) optotype configurations correctly.

Next, in step 536 of FIG. 18, the computing device 402 is specifically programmed to generate a quantitative assessment of the head impulse test based upon the total number of visual object configurations (e.g., optotype configurations) that the subject 418 identified correctly during the dynamic portion of the head impulse test (i.e., during the third set of successive trials). Then, in step 538 of FIG. 18, the computing device 402 is specifically programmed to output the quantitative assessment of the head impulse test for the subject 418 on the output screen of the visual display device 404. The head impulse testing procedure concludes at step 540 in FIG. 18.

In one or more embodiments, the head impulse test may comprise a plurality of different sets of successive trials performed at different head velocities. For example, the first set of successive trials may be performed using a predetermined minimum velocity or speed of approximately 100 degrees per second (or 100 degrees per second), the second set of successive trials may be performed using a predetermined minimum velocity or speed of approximately 150 degrees per second (or 150 degrees per second), and the third set of successive trials may be performed using a predetermined minimum velocity or speed of approximately 200 degrees per second (or 200 degrees per second). In these one or more embodiments, different sets of successive trials may be performed at incrementally higher velocities or speeds over the course of the head impulse test.

In one or more embodiments, a baseline visual processing time and static visual acuity value must have been previously stored in the computing device 402 in order to permit the subject 418 to perform the dynamic portion of the head impulse test. For example, if no baseline visual processing time and static visual acuity was previously determined on the day of the head impulse test, the subject 418 must first complete the static visual acuity testing and the visual processing time testing prior to performing the dynamic portion of the head impulse test.

As briefly mentioned above, the stimulus levels and threshold determinations during the first and second sets of successive trials of the vision testing may be determined by the computing device 402 by means of executing a parameter estimation algorithm. In particular, during the first static set of successive trials during the head impulse test, the optotype size selected for each trial, and the threshold optotype size computed in step 510, may be computed using the parameter estimation algorithm. Similarly, during the visual processing time test performed in conjunction with the head impulse test, the optotype display time selected for each trial, and the threshold visual processing time computed in step 522, may be computed using the parameter estimation algorithm. As such, the parameter estimation computations performed by the computing device 402 will be explained in detail hereinafter.

Initially, the parameter estimation computational procedure during the first static set of successive trials during the head impulse test will be explained. In an exemplary embodiment, the optotype range for the set of static successive trials (i.e., static visual acuity (SVA) range) may be −0.3 logMAR to 1.0 logMAR, and it may be divided into steps of 0.05 logMAR, thereby resulting in a total of twenty-seven (27) steps overall. The initial optotype size that is presented to the subject by the computing device 402 is 0.4 logMAR. The initial optotype size of 0.4 logMAR is presumed to be easy for most subjects to recognize so that the configuration thereof will be properly identified. If the subject incorrectly identifies the configuration of the initial optotype, the computing device 402 increases the optotype size by four (4) steps so that the next optotype size presented to the subject is 0.6 logMAR. After every incorrect answer, the computing device 402 increases the optotype size by four (4) steps until the upper range limit of 1.0 logMAR is reached. The subject may be given one or more chances to answer correctly at the upper range limit of 1.0 logMAR. If the subject fails to correctly identify the configuration of the optotype with a size of 1.0 logMAR after having been given one or more chances, the computing device 402 will end the static portion of the test.

Conversely, if the subject correctly identifies the configuration of the initial optotype, the computing device 402 decreases the optotype size by three (3) steps so that the next optotype size presented to the subject is 0.25 logMAR. After every correct answer, the computing device 402 decreases the optotype size by three (3) steps until the subject identifies the optotype configuration incorrectly. At this point, the computing device 402 presumes that the subject's threshold must lie somewhere between the optotype sizes identified correctly and incorrectly. The process is continued, and the computing device 402 increases the optotype size by two (2) steps (0.1 logMAR) for every incorrect answer, and decreases the optotype size by one (1) step (0.05 logMAR) for every correct answer. Each time the subject correctly identifies the optotype configuration, the computing device 402 checks the number of correct answers and the number of incorrect answers for that particular threshold. When the computing device 402 determines that the percent ratio of correct answers to the total number of answers (correct/(correct+incorrect)*100) is between 50% and 75%, then the computing device 402 determines that the present optotype size is the subject's threshold. The computing device 402 further compares the number of correct and incorrect answers between the current optotype size and the next smaller optotype size. If the computing device 402 determines that the ratio of correct answers to the total number of answers is between 50% and 66%, then the static series of trials is ended, and the mean of the two (2) adjacent points (i.e., optotype sizes) is taken as the threshold. The static series of trials is continued by the computing device 402 until one of the two (2) conditions described above is fulfilled. For example, the total number of static trials conducted by the computing device 402 may be thirty (30) overall trials.

Now, the manner in which the computing device 402 carries out the parameter estimation computational procedure for the threshold visual processing time determination will be explained. The computational procedure for threshold visual processing time of the subject uses a visual processing time range of 35 milliseconds to 70 milliseconds, and it is divided into steps of 5.0 milliseconds, thereby resulting in a total of eight (8) steps overall. For the threshold visual processing time of the subject, the computing device 402 does not begin with a large initial step size. Rather, if the subject identifies the configuration of the optotype incorrectly, the computing device 402 increases the visual processing time by two (2) steps (10.0 milliseconds), while if the subject identifies the configuration of the optotype correctly, the computing device 402 decreases the visual processing time by one (1) step (5.0 milliseconds). During the visual processing time computational procedure, the computing device 402 performs the same two conditional comparisons described above for the static trials (i.e., determining whether between 50% and 75%, and whether between 50% and 66%).

In accordance with a further illustrative embodiment of the invention, in order to enhance the accuracy and reduce the overall time duration of a vision test or vision training routine, the computing device 402 of the vision testing system 400 may be programmed to continually monitor the head velocity of the user during the vision test or vision training routine. This performance enhancement feature of the vision testing system 400 may be used in conjunction with any vision test or training routine that is able to benefit from such a feature, such as the gaze stabilization test (GST) and the dynamic visual acuity (DVA) test described in U.S. Pat. Nos. 9,066,667, 9,277,857, and 9,517,008, the entire disclosures of each of which are hereby incorporated herein by reference in their entireties.

In this further illustrative embodiment, the computing device 402 of the vision testing system 400, which is operatively coupled to the head motion sensing device 428 and the visual display device 404, is programmed to: (i) establish a prescribed threshold percentage of a target velocity or speed (e.g., 85% of the target velocity) for the head 430 of the user (e.g., subject 418) during a vision test or training routine; (ii) determine whether an actual head velocity or speed for the head 430 of the user 418 measured by the head motion sensing device 428 reaches or exceeds the prescribed threshold percentage of the target velocity or speed (e.g., exceeds 85% of the target velocity); (iii) when the actual head velocity or speed for the head 430 of the user 418 reaches or exceeds the prescribed threshold percentage of the target velocity or speed (e.g., exceeds 85% of the target velocity), generate and display a configuration of a visual object 410 (e.g., an optotype) on the output screen of the visual display device 404 during the same cycle of rotational head displacement during which the prescribed threshold percentage of the target velocity or speed was reached or exceeded; and (iv) determine whether or not the user correctly identifies the configuration of the visual object 410 displayed on the output screen of the visual display device 404 (e.g., in the manner described above for the head impulse test, and/or in the manner described for the gaze stabilization test (GST) and the dynamic visual acuity (DVA) test in U.S. Pat. Nos. 9,066,667, 9,277,857, and 9,517,008).

Figure 40:
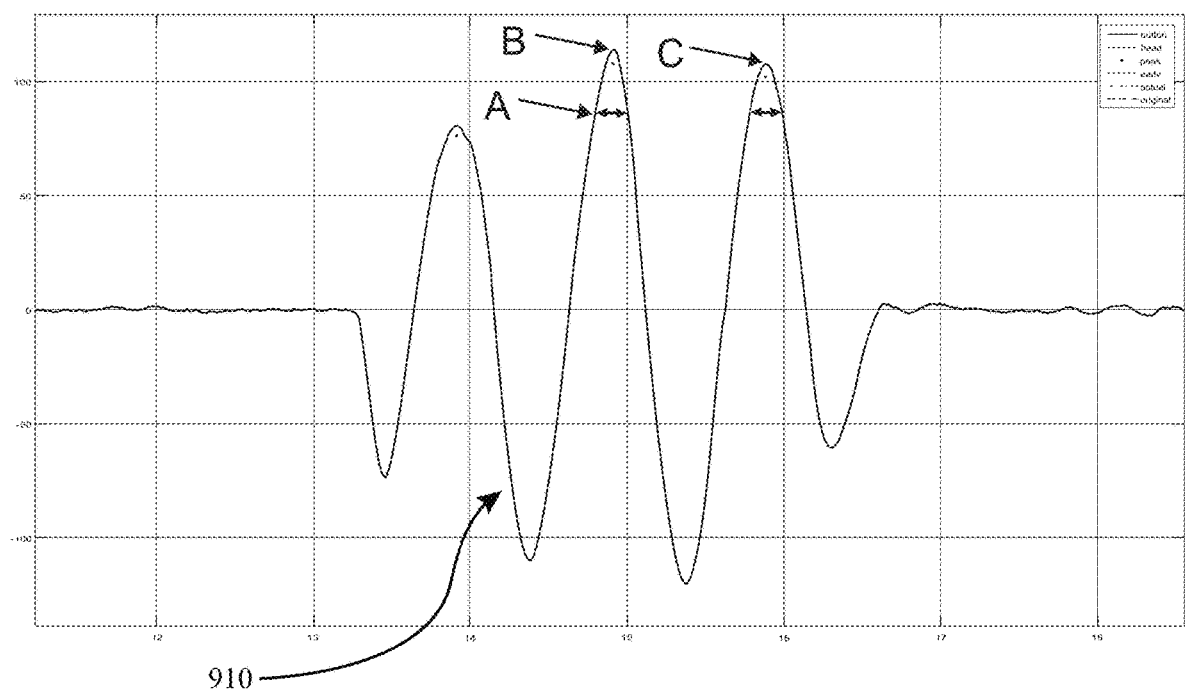
FIG. 40 illustrates a graph of a head angular velocity curve generated during the performance of a vision test, according to one embodiment of the invention.

Now, with reference to FIG. 40, this performance enhancement feature of the vision testing system 400 will be explained in more detail. In FIG. 40, a graph of a head angular velocity curve 910 generated during the performance of a vision test is illustrated. The graph in FIG. 40 shows the head velocity (in degrees per second) during one trial of a vision test (e.g., a dynamic visual acuity (DVA) test) where the target head velocity is 100 degrees per second. As shown in FIG. 40, when the head velocity reaches 85% of the target velocity (A), the optotype 410 is displayed within the same cycle for a predetermined visual display time (as indicated by the line with the arrows at each end in FIG. 40). That is, the computing device 402 is programmed to display the configuration of the visual object 410 on the output screen of the visual display device 404 for a predetermined visual display time (VDT) after the actual head velocity or speed for the head of the user reaches or exceeds the prescribed threshold percentage of the target velocity or speed (at point "A" in FIG. 40). Then, the computing device 402 measures the peak (B), and if the peak is not within +15% of the target head velocity, the computing device 402 warns the user 418 and forces a retest. That is, in this further embodiment, the computing device 402 is programmed to determine, after the cycle of rotational head displacement has concluded, whether a peak value (B) of the actual head velocity or speed for the head 430 of the user 418 measured by the head motion sensing device 428 was within a prescribed percentage range of the target velocity or speed (e.g., within +15% of the target head velocity) for a trial of the vision test or training routine. When the peak value of the actual head velocity or speed for the head 430 of the user 418 was within the prescribed percentage range of the target velocity or speed (e.g., within +15% of the target head velocity), the identification of the configuration (e.g., pointing direction) of the visual object 410 by the user 418 is taken into account when assessing results of the vision test or training routine. Conversely, when the peak value of the actual head velocity or speed for the head 430 of the user 418 was not within the prescribed percentage range of the target velocity or speed (e.g., not within +15% of the target head velocity), the identification of the configuration of the visual object 410 by the user 418 is not taken into account when assessing results of the vision test or training routine, and the user 418 is instructed to repeat the trial of the vision test or training routine.

In this further embodiment, with reference again to FIG. 40, the computing device 402 does not first detect the peak (B) when it is within the range, and then wait to display the optotype in the next cycle (C) of sinusoidal head movements. After all, when the optotype is not displayed until the next cycle (C), there is no guarantee that the user's head velocity at (C) will be within the tolerance level for the target velocity. Also, the vision test takes longer to complete. In the implementation of the present further embodiment, the last cycle never happens, and the vision test advantageously ends faster.

In this further embodiment, the predetermined visual display time (VDT) for displaying the configuration (e.g., particular pointing direction) of the visual object 410 is equal to a visual processing time (VPT) computed for the user added to a predetermined time value (e.g., 35 milliseconds). The visual processing time (VPT) is an amount of time that the visual object 410 needs to be displayed on the output screen of the visual display device 404 in order for the user 418 to comprehend the displayed configuration (e.g., pointing direction) of the visual object 410.

In this further embodiment, if the actual head velocity or speed for the head 430 of the user 418 measured by the head motion sensing device 428 does not reach or exceed the prescribed threshold percentage of the target velocity or speed (e.g., does not reach or exceed 85% of the target velocity), the optotype 410 is not displayed and the vision test will continue. In this further embodiment, the user 418 has to be within ±15% of the target velocity or speed for the optotype 410 to be displayed.

During this further embodiment, the head velocity or speed of the user 418 is continually monitored (i.e., there is real-time detection of head velocity). For example, depending on the sampling frequency of the motion sensing device 428 (e.g., the sampling frequency of the inertial measurement unit 428), the head velocity or speed of the user 418 may be continually monitored every 2 milliseconds or more frequent (i.e., if the sampling frequency of the inertial measurement unit 428 is 500 Hertz or more).

In accordance with a yet further illustrative embodiment of the invention, in order to enhance the accuracy of a vision test or vision training routine and to allow for high performance testing and training, the computing device 402 of the vision testing system 400 may be programmed to increase the required amplitude of the user in response to increased head velocity. This performance enhancement feature of the vision testing system 400 may be used in conjunction with any vision test or training routine that is able to benefit from such a feature, such as the gaze stabilization test (GST) and the dynamic visual acuity (DVA) test described in U.S. Pat. Nos. 9,066,667, 9,277,857, and 9,517,008, the entire disclosures of each of which are hereby incorporated herein by reference in their entireties.

In this further illustrative embodiment, the computing device 402 of the vision testing system 400, which is operatively coupled to the head motion sensing device 428 and the visual display device 404, is programmed to: (i) establish a prescribed amplitude or period for rotational displacement of the head 430 of the user (e.g., subject 418) during a vision test or training routine; (ii) determine a peak head velocity or speed for the head 430 of the user 418 based upon output data from the head motion sensing device 428 while the head 430 of the user 418 undergoes rotational displacement; (iii) generate and display a configuration of a visual object 410 (e.g., an optotype) on the output screen of the visual display device 404 when the head 430 of the user 418 undergoes rotational displacement equal to or above the prescribed amplitude, or where a cycle of the rotational displacement of the head 430 of the user 418 has a time duration equal to or above the prescribed period; (iv) increase a value of the prescribed amplitude or period for the rotational displacement of the head 430 of the user 418 for a successive trial of the test or training routine when the peak head velocity or speed is determined to have increased; and (v) determine whether or not the user 418 correctly identifies the configuration of the visual object 410 displayed on the output screen of the visual display device 404 (e.g., in the manner described above for the head impulse test, and/or in the manner described for the gaze stabilization test (GST) and the dynamic visual acuity (DVA) test in U.S. Pat. Nos. 9,066,667, 9,277,857, and 9,517,008).

Figure 41:
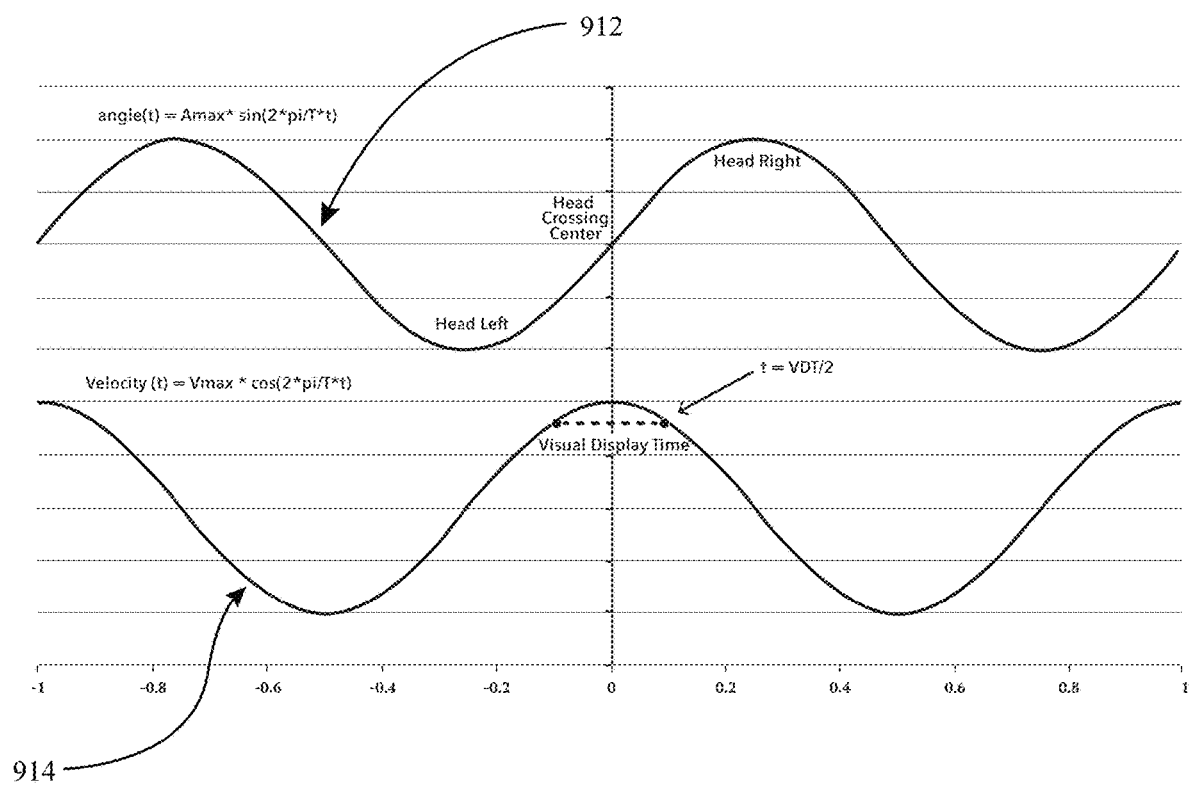
FIG. 41 illustrates a first graph of an approximated head angular displacement curve for a user during the performance of a vision test and a second graph of an approximated head angular velocity curve for the user during the performance of the vision test, according to another embodiment of the invention.

Now, with reference to FIG. 41, this performance enhancement feature of the vision testing system 400 will be explained in more detail. In FIG. 41, a first graph of an approximated head angular displacement curve 912 and a second graph 914 of an approximated head angular velocity curve during the performance of a vision test is illustrated. In FIG. 41, it is assumed that the head 430 of the user 418 is moving sinusoidally with the peak angle of Amax and period of T in accordance with the following equation:

$$\text{head angle}(t) = A\max * \sin(2 * pi/T * t) \quad (8)$$

The angle at the center is zero and at the extreme right and left positions are +Amax and −Amax, respectively. In FIG. 41, it is assumed that the head velocity of the head 430 of the user 418 is moving sinusoidally in accordance with the following equation:

$$\text{head velocity}(t) = V\max * \cos(2 * pi/T * t) \quad (9)$$

As shown in FIG. 41, the head velocity is equal to zero at the extreme right and left positions, +Vmax at the center when moving left to right, and −Vmax at the center when moving right to left.

In this further embodiment, during the GST and DVA, the optotype 410 is displayed for the duration of the visual display time (VDT). The optotype is turned on at −VDT/2 seconds before the peak velocity, and is turned off after +VDT/2 seconds after the peak (see FIG. 41). Ideally, the change in the head velocity should be minimal during the display of the optotype 410. This requires the period of the sine wave to be sufficiently large. The head velocity at the −VDT/2 is as follows:

$$Vvdt2 = V\max * \cos(2*pi/T*(VDT/2)) = V\max * \cos(pi*VDT/T) \quad (10)$$

Table 1 below shows the relationship between the VDT and T for different ratios of Vvdt2/Vmax:

TABLE 1

Relationship between VDT and T for Different Ratios of Vvdt2/Vmax

| Vvdt2/Vmax | T/VDT |
|---|---|
| 90% | 6.97 |
| 85% | 5.66 |
| 80% | 4.88 |

In this further embodiment, the ratio of 85% is deemed to be the most appropriate value, which means the period should be at least 5.66 times VDT:

$$T > 5.66 * VDT \quad (11)$$

The relationship between the peak head velocity and head angle is:

$$V\max = 2*pi/T*A\max \quad (12)$$

In this further embodiment, Vmax is set depending on the requirements of the GST and DVA as follows: (i) target head velocity for DVA=100 deg./sec. (acceptable range 85-120 deg/sec); (ii) target head velocities for standard GST=30-150 deg./sec. (acceptable range −15% to +20% of target); and (iii) target head velocities for high-performance GST=150-300+deg./sec. (acceptable range −15% to +20% of target). As a result, either the period (T) or the peak angle (Amax) can be set, and the other parameter will be determined from above equation (12). In addition, if the limit on T is imposed from equation (11) above.

$$T = 2*pi*A\max/V\max > 5.66*VDT \rightarrow A\max/V\max > 0.9*VDT \quad (13)$$

In this further embodiment, the predetermined visual display time (VDT) for displaying the configuration (e.g., particular pointing direction) of the visual object 410 is equal to a visual processing time (VPT) computed for the user added to a predetermined time value (e.g., 35 milliseconds). The visual processing time (VPT) is an amount of time that the visual object 410 needs to be displayed on the output screen of the visual display device 404 in order for the user 418 to comprehend the displayed configuration (e.g., pointing direction) of the visual object 410.

In this further embodiment, the computing device 402 of the vision testing system 400 may be further programmed to establish the prescribed amplitude (Amax) for the rotational displacement of the head 430 of the user 418 during the vision test or training routine; and determine the prescribed amplitude (Amax) for the rotational displacement of the head 430 of the user 418 as a function of the peak head velocity or speed for the head 430 of the user 418 and a predetermined visual display time (VDT) for displaying the configuration (e.g., pointing direction) of the visual object 410. More specifically, as shown in equations (12) and (13) above, there is a relationship between the peak velocity and the peak amplitude. This relationship states that for the test conditions of this embodiment (Amax/Vmax)>0.9*VDT, where Amax is the head amplitude, Vmax is the head velocity (measured by the head motion sensing device 428), and VDT is the Visual Processing Time (VPT, which is measured as a part of the BVA test protocol)+35 milliseconds. For example, let's assume that the target velocity is 200 deg./sec. and the subject's VPT was measured as 65 milliseconds (VDT=0.1 sec). From equation (13) above, the head amplitude should be Amax=200*0.9*0.1=18 degrees. If the subject's head amplitude is much less than 18 degrees, there is no way that he or she can reach the required target velocity. Thus, the software on the computing device 402 will prohibit the optotype 410 from being displayed. The therapist 414 can see this from the displayed results and should encourage the subject 418 to increase his or her head amplitude. For example, in this embodiment, an "up" arrow is displayed on the output screen of the visual display device 404 in order to indicate the amplitude of the subject's head displacement needs to be increased. Now, if in the next trial, the target velocity increases to 250 deg./sec., the required amplitude will increase too and the subject 418 must move his head 430 with a larger amplitude.

In this further embodiment, the computing device 402 of the vision testing system 400 may be further programmed to establish the prescribed period (T) for the rotational displacement of the head 430 of the user 418 during the vision test or training routine; determine the prescribed period (T) for the rotational displacement of the head 430 of the user 418 as a function of a constant value (e.g., 5.66) and a predetermined visual display time (VDT) for the user 418; measure a time duration between two consecutive peaks on a head velocity curve generated using the output data from the head motion sensing device 428 (e.g., two consecutive peaks on the head angular velocity curve 914 in FIG. 41) to determine the actual time period; and then determine if the actual time period is greater than the prescribed period (T). That is, if the actual time period for the user 418 is greater than 5.66 times the visual display time for the user 418 (refer to equation (11) above), then period is adequate, and the visual object 410 will be displayed. Conversely, if the actual time period for the user 418 is less than 5.66 times the visual display time for the user 418, then period is inadequate, and the "up" arrow is displayed on the output screen of the visual display device 404 in order to indicate the amplitude of the subject's head displacement needs to be increased.

Also, in this further embodiment, if the time for two consecutive velocity peaks is determined for the user 418, the actual maximum head amplitude of the user 418 can be approximated without actually measuring the head amplitude. The approximated head amplitude does not have to be exact (e.g., the tolerance may be +15%). Then, the approximated head amplitude determined for the user 418 can be compared to the computed Amax (Amax=Vmax*0.9*VDT) to determine if the amplitude of the user 418 is sufficient.

Advantageously, increasing the required amplitude of the user 418 in response to increased head velocity allows vision tests (e.g., the gaze stabilization test) and vision training to be performed using higher head velocities (e.g., up to 300 degrees per second or more) because the head velocity is still able to be relatively constant during the display of the optotype 410 if the amplitude and period of the velocity curve is sufficiently large. For example, a reasonable limit is for the velocity to stay within 15% of the target velocity during the display of the optotype. As such, using the progressive mode described above where the required head amplitude is increased gradually as the peak head velocity is increased, allows the maximum allowable velocity to still reach 300 deg./sec. even for a visual processing time (VPT) of 60 milliseconds. In the embodiment described above, the computing device 402 is programmed to continually check throughout the vision test to make sure that the user 418 is complying with head amplitude requirement. The head amplitude is not set at a constant value during the test.

Figure 22:
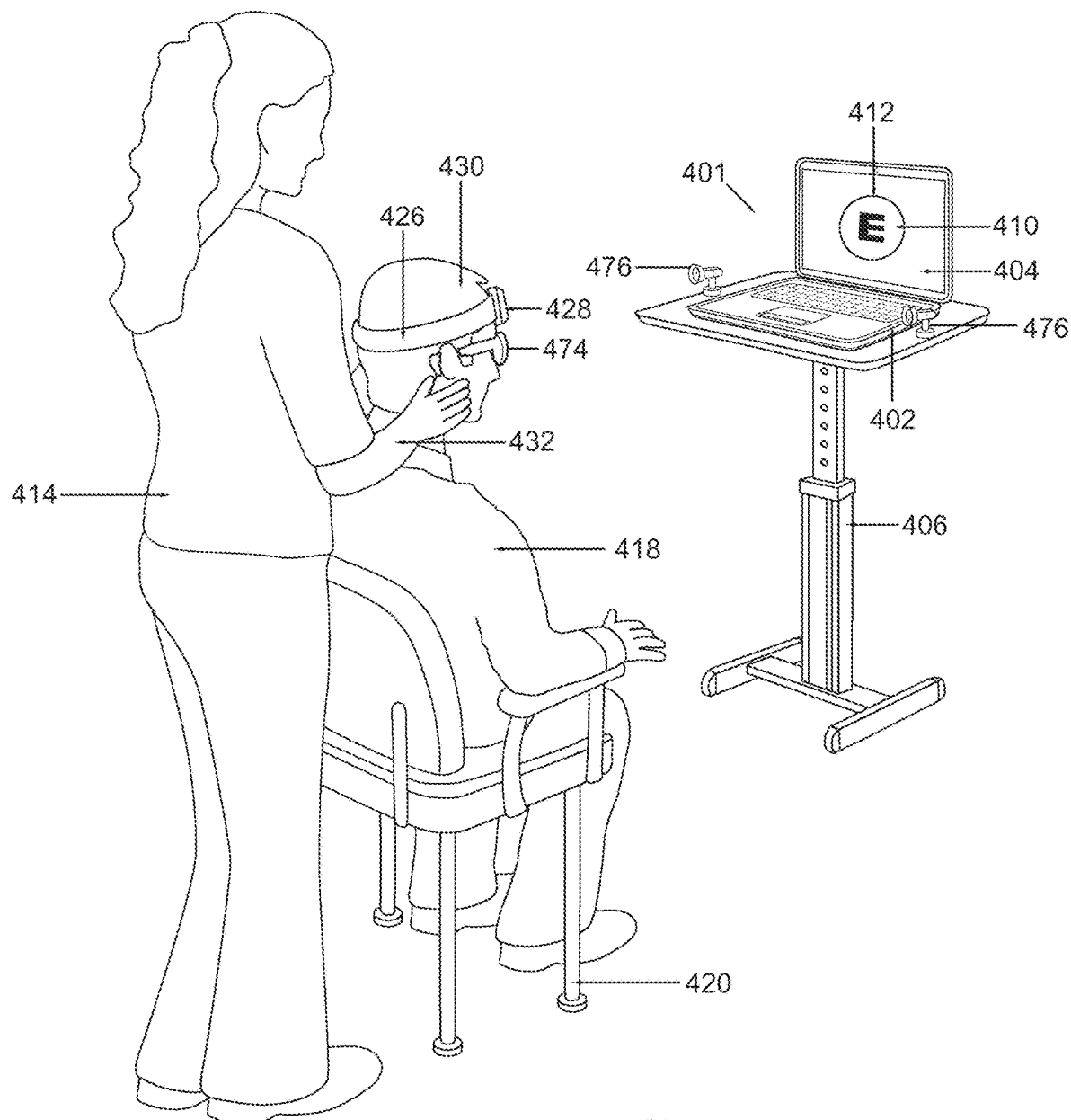
FIG. 22 is a diagrammatic perspective view of a second exemplary vision testing system with eye movement tracking, according to yet a further embodiment of the invention.

In accordance with a still further illustrative embodiment of the invention, the subject may be outfitted with an eye movement tracking device 474 during the head impulse testing procedure so that the eye movement of the subject 418 may be tracked during the head impulse test (e.g., refer to FIG. 22). In particular, while the steps 528-532 in FIG. 17 are performed, the eye movement of the subject 418 may be continually tracked, and the eye position of the subject 418 may be correlated with subject's identification of the optotype to determine if there is a specific relationship between the position of the subject's eyes and whether or not the subject 418 correctly identifies the optotype.

In a further embodiment, angular velocities of the eye(s) and head of the subject 418 obtained from an eye movement tracking device and a head position measurement device may be used to determine a peripheral vision score using central displacement from the optotype.

Referring to FIG. 22, an exemplary embodiment of a system for testing the vision of a subject with eye movement tracking is seen generally at 401 in FIG. 22. The system 401 illustrated in FIG. 22 may be used for the head impulse testing procedure described above to determine if there a specific relationship between the position of the subject's eyes and whether or not the subject 418 correctly identifies the optotype. As shown in FIG. 22, the system 401 generally comprises a laptop computing device 402 (i.e., a computing device that is capable of collecting, storing, and processing data), which in turn, is operatively coupled to a head motion sensing device 428 and an eye movement tracking device 474. In FIG. 22, it can be seen that the eye movement tracking device 474 may be in the form of goggles or glasses worn on the head of the subject 418. The goggles or glasses worn on the head of the subject 418 may be in the form of one of the eye movement measurement devices 100, 200, which incorporate both video-based and infrared sensing means. In the illustrative embodiment, the eye movement measurement devices 100, 200 may be operatively connected to the laptop computing device 402 by means of either a wired connection or a wireless connection. In addition, the head motion sensing device 428 is removably coupled to the head 430 of the subject 418 using a stretchable, elastic headband 426 (i.e., a resilient band 426). In one or more alternative embodiments, the head motion sensing device may integrated into the goggles containing the eye movement tracking device 474 (e.g., the head motion sensing device 474 may be in the form of an inertial measurement unit (IMU) integrated in the goggles worn by the subject 418).

In one or more embodiments, the stretchable, elastic headband 426 that attaches the head motion sensing device 428 to the head 430 of the subject 418 may include a strap and a compressible piece of material disposed on an interior surface of the strap. When the head motion sensing device 428 is attached to the head 430 of the subject 418 by the headband 426, the compressible piece of material is configured to be disposed between a portion of the strap and the head 430 of the subject 418 so as to provide a cushion effect for the subject 418 (i.e., to improve the comfort of the subject 418 while wearing the device 428). In an exemplary embodiment, the compressible piece of material disposed on the interior surface of the strap may comprise a piece of foam, a polymeric material, such as silicone, or a composite material comprising a gel.

Figure 23:
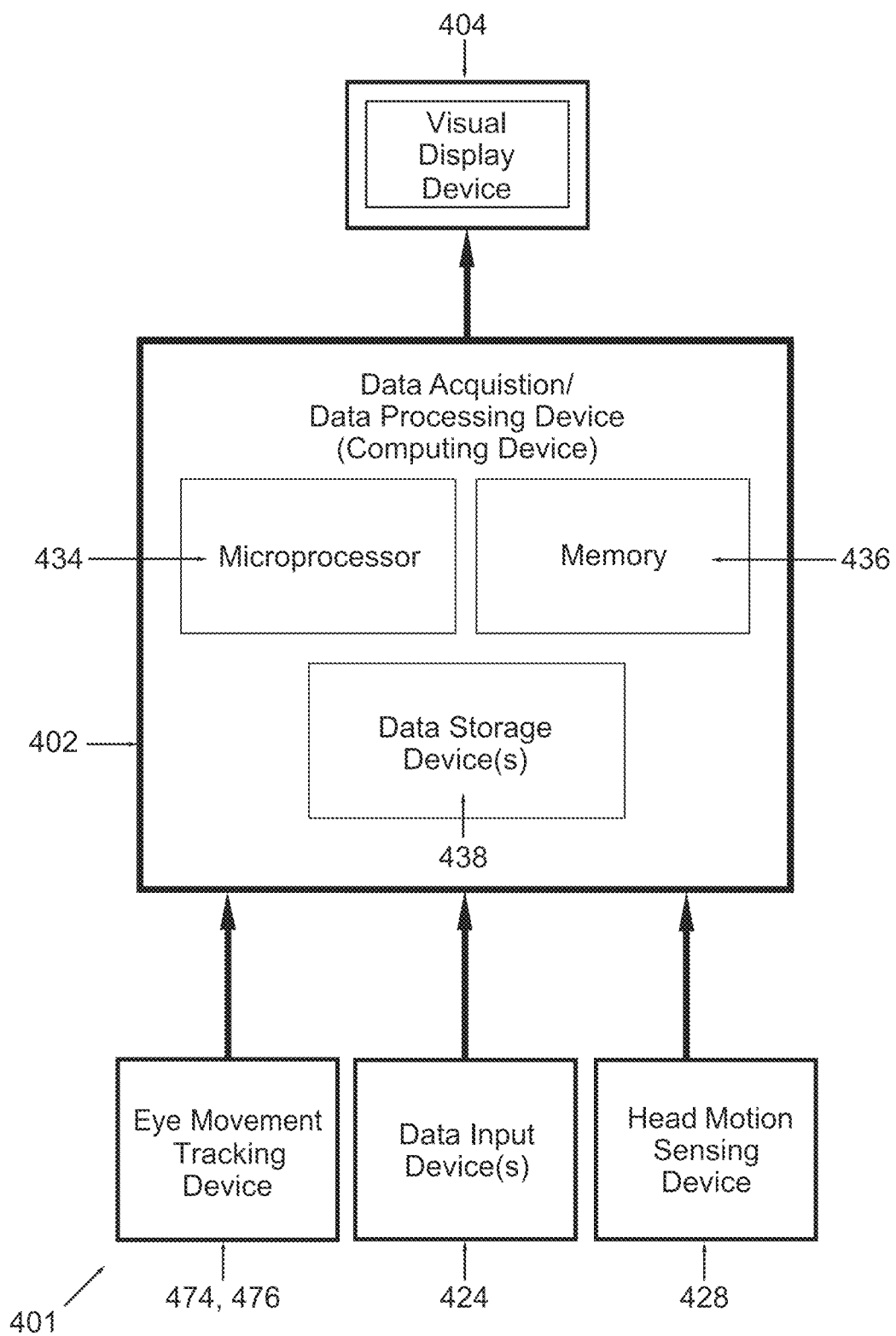
FIG. 23 is a block diagram of constituent components that may be utilized in the vision testing system with eye movement tracking of FIG. 22.

Now, turning to FIG. 23, it can be seen that the computing device 402 of the vision testing system with eye movement tracking 401 may comprise a microprocessor 434 for processing data, memory 436 (e.g., random access memory or RAM) for storing data during the processing thereof, and data storage device(s) 438, such as one or more hard drives, compact disk drives, floppy disk drives, flash drives, or any combination thereof. As shown in FIG. 23, the head motion sensing device 428, the eye movement tracking devices 474, 476, and the visual display device 404 are operatively coupled to the computing device 402 such that data is capable of being transferred between these devices. Also, as illustrated in FIG. 23, one or more data input devices, such as the wireless mouse 424, a keyboard, and a touchpad, are operatively coupled to the computing device 402 so that a user is able to enter data into the computing device 402. In some embodiments, the computing device 402 may be in the form of a laptop computer (as shown in FIG. 22), while in other embodiments, the computing device 402 may be embodied as a desktop computer.

In an alternative embodiment, rather than the eye movement tracking device 474 being integrated into goggles or glasses worn on the head of the subject 418, the eye movement tracking device may be in the form of one or more remote eye movement tracking devices 476 (e.g., in the form of eye movement tracking devices 476 disposed on the top surface of table 406). In this alternative embodiment, the eye movement tracking devices 476 (e.g., video-based and infrared sensing means) may capture the movement and/or position of the subject's eyes while he or she performs the head impulse testing procedure described above. As shown in FIG. 22, the eye movement tracking devices 476 may be in the form of video-based and infrared sensing means placed in front of the subject or patient 418. In the illustrative embodiment of FIG. 22, each of the eye movement tracking devices 476 may be configured to track one of the eyes of the subject 418 (i.e., the left eye movement tracking device 476 tracks the center of the pupil for left eye of the subject 418, while the right eye movement tracking device 476 tracks the center of the pupil for right eye of the subject 418). In the illustrative embodiment, the eye movement tracking devices 476 may be operatively connected to the laptop computing device 402 by means of either a wired connection or a wireless connection. Also, if markers are placed on the head 430 of the subject 418 (e.g., on the forehead of the subject 418), the movement of the head 430 of the subject 418 may also be determined using the devices 476, in addition to the eye movement of the subject 418. In addition, as described hereinafter, the devices 476 may comprise camera devices used for the markerless determination of the head position and velocity. In one or more further embodiments, the eye movement tracking device 474 described above, which is disposed in the goggles or glasses worn by the subject 418, may be used in conjunction with the eye movement tracking devices 476 so as to form a hybrid system for tracking the eye movement of the subject 418.

Because the eye position of the subject 418 measured by the eye movement tracking devices 474, 476 is indicative of whether or not the subject 418 is able to see the visual object (i.e., the optotype) or not, in some further embodiments, the determination of the eye position for the subject 418 enables the head impulse testing procedure to be performed without requiring the subject 418 to identify the optotype (i.e., upon the determination by the computing device 402 that there is a specific relationship between the position of the subject's eyes and whether or not the subject 418 correctly identifies the optotype). For example, if the gaze direction of the subject's eyes, as determined using the eye movement tracking devices 474, 476, is not in the direction of the visual object (i.e., the optotype), the computing device 402 may determine that the subject 418 will not be able to identify the configuration of the optotype correctly. Conversely, if the gaze direction of the subject's eyes, as determined using the eye movement tracking devices 474, 476, is consistent with the location of the visual object (i.e., the optotype), the computing device 402 may determine that the subject 418 will be able to identify the configuration of the optotype correctly. However, in the other embodiments of the invention, it is preferred to have the subject 418 identify the optotype during the head impulse test while his or her eye movement is simultaneously measured.

Figure 24:
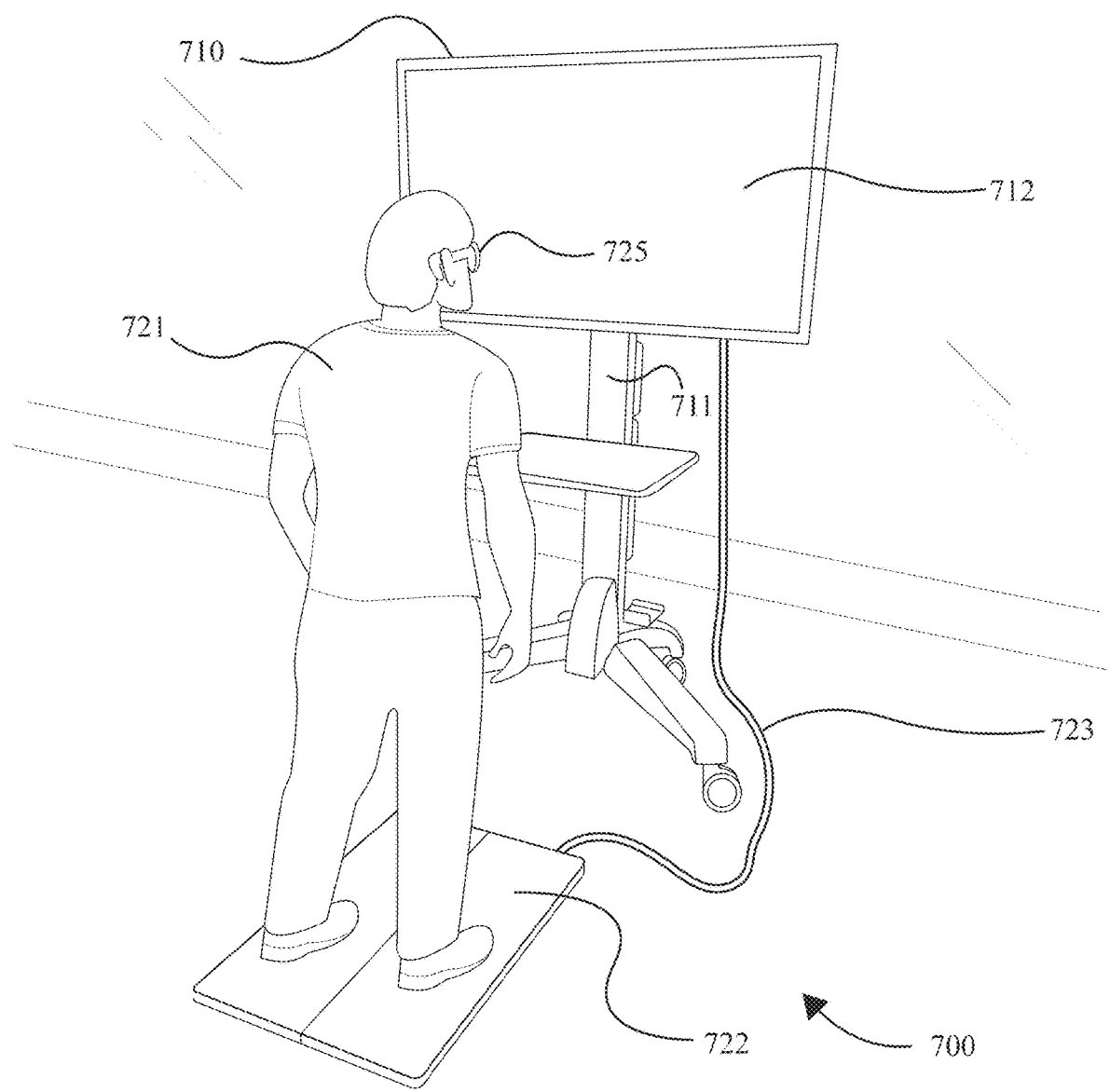
FIG. 24 is a diagrammatic perspective view of a third exemplary vision testing/training system, according to still a further embodiment of the invention.

In accordance with yet a further illustrative embodiment of the invention, a vision testing/training system is disclosed that is particularly configured for tracking eye movements and/or eye positions of a user 721 performing a vision test or vision training session. An illustrative embodiment of a vision testing/training system with eye movement tracking is seen generally at 700 in FIG. 24. In the illustrative embodiment, the vision testing/training system 700 generally comprises a visual display device 710 and a data processing device and/or data processing and data acquisition device 714 (e.g., a computing device or a small-form-factor personal computer, such as the Intel® NUC—see FIG. 25). The small-form-factor personal computer 714 is one illustrative form of a data processing device and/or data processing and data acquisition device. In FIG. 24, the small-form-factor personal computer 714 may be mounted on the back of the visual display device 710 (e.g., mounted on the back panel of a touchscreen visual display device with output screen 712). In one or more embodiments, the screen images of the training modes described hereinafter are displayed on the output screen 712 of the visual display device 710 so that the user 721 is able to interact with one or more visual objects in the screen images.

In the illustrative embodiment of FIG. 24, the visual display device 710 is disposed on an adjustable height stand or cart 711 so that the height of the visual display device 710 is selectively adjustable by a user 721. Advantageously, prior to the testing/training session of the user 721, the height of the stand 711 may be adjusted such that the approximate center of the visual display device 710 is generally horizontally aligned with the eyes of the standing user 721 (i.e., so the user 721 is generally looking at the central portion of the visual display device 710 during the testing/training).

Figure 25:
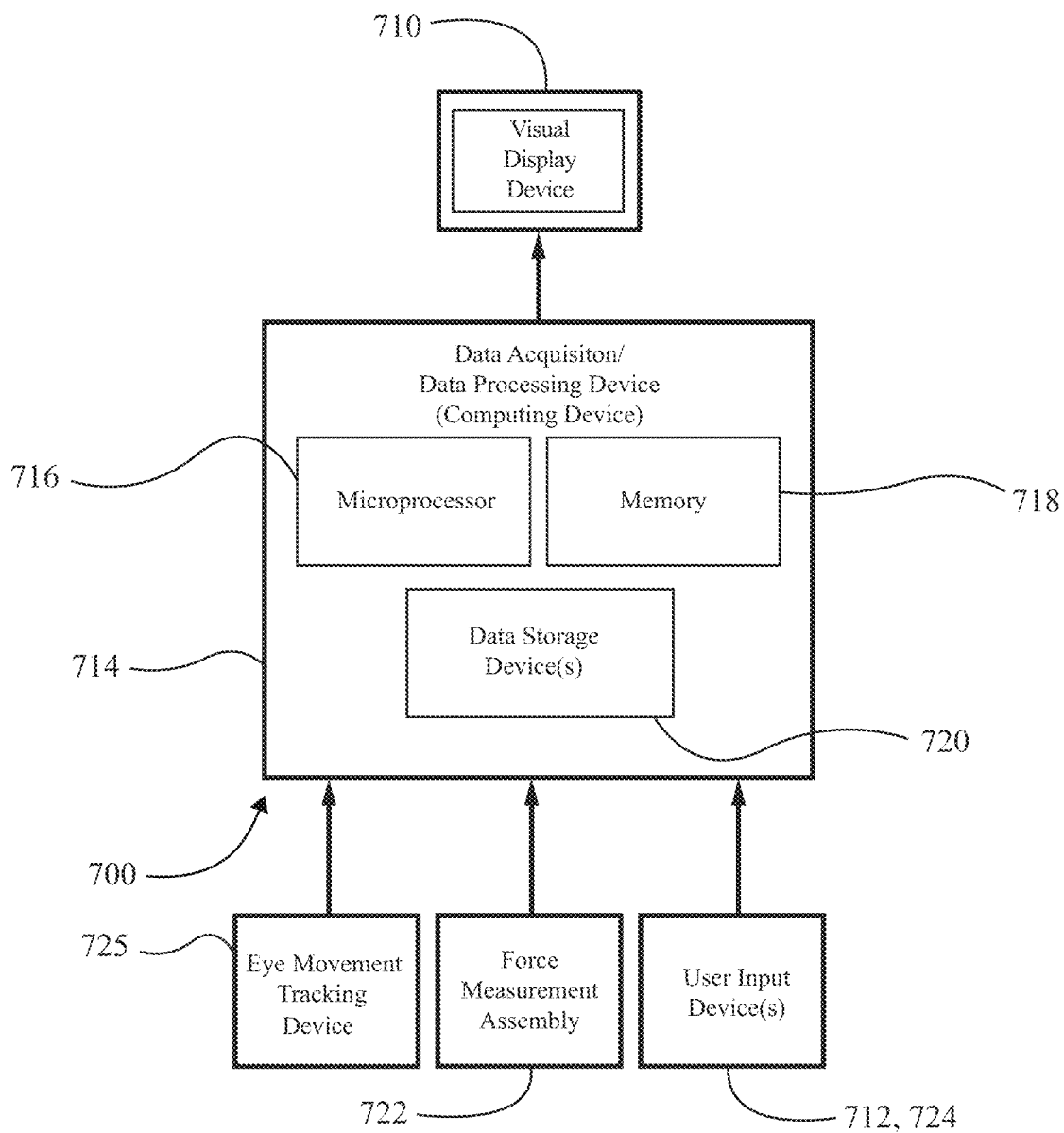
FIG. 25 is a block diagram of constituent components that may be utilized in the embodiment of the vision testing/training system of FIG. 24.

As shown in the illustrative block diagram of FIG. 25, the vision testing/training system 700 further includes one or more user input devices 712, 724. The user input device 712, 724 is configured to output a first signal based upon an input response by a user 721. In the illustrative embodiment, the user input device 712 may comprise the touchscreen user interface of the visual display device 710. The touchscreen user interface may be a force/pressure based touchscreen that is able to measure the amount of force applied to the touchscreen by the user (touchscreen force data based on subject and hardware interaction can enhance data collected, force data can be used, for example, to determine intent versus hesitancy in sports such as boxing). In other embodiments, the user input device may alternatively comprise at least one of: (i) a voice recognition device, (ii) a wireless remote control with one or more buttons, (iii) a keyboard (i.e., a virtual or physical keyboard), (iv) a clicking device, (v) a joystick, and (vi) a pointing device. Also, in one or more further embodiments, the primary user input device 712 may comprise the touchscreen user interface of the visual display device 710, and the supplementary user input device 724 may comprise one of: (i) a voice recognition device, (ii) a wireless remote control with one or more buttons, (iii) a keyboard (i.e., a virtual or physical keyboard), (iv) a clicking device, (v) a joystick, and (vi) a pointing device.

In the illustrative embodiment, during the testing/training of the user 721, the user 721 may use the user input device 712, 724 in order to enter and transmit his or her response to the data processing device 714 (e.g., the selection of a particular visual object on the output screen 712 of the visual display device 710).

In addition, as shown in FIGS. 24 and 25, the vision testing/training system 700 further includes an eye movement tracking device 725. During the vision testing/training conducted by the system 700, the eye movement tracking device 725 is configured to track eye movement and/or eye position of the user 721, and output a second signal based upon the tracked eye movement and/or eye position of the user 721. As shown in FIG. 25, the eye movement tracking device 725 is operatively coupled to the computing device 714 such that data is capable of being transferred to the computing device 714 from the eye movement tracking device 725. The eye movement tracking device 725 of the system 700 may be in the form of the eye movement measurement devices 100, 200 described above, or the eye movement tracking device 725 may comprise a different type of eye movement tracking device.

Now, turning again to FIG. 25, it can be seen that the data processing device 714 (e.g., the small-form-factor personal computer 714) of the vision testing/training system 700 comprises a microprocessor 716 for processing data, memory 718 (e.g., random access memory or RAM) for storing data during the processing thereof, and data storage device(s) 720, such as one or more internal solid state drives, external flash drives, or any combination thereof. As shown in FIG. 25, the visual display device 710 is operatively coupled to the computing device 714 such that data is capable of being transferred between these devices (e.g., the visual display device 710 may be a touchscreen visual display device with a touchscreen user interface as described above). Also, as illustrated in FIG. 25, one or more data input devices 712, 724, such as the touchscreen user interface or a voice recognition sensor are operatively coupled to the computing device 714 so that a user is able to enter data into the computing device 714. In one or more alternative embodiments, the computing device 714 may be in the form of a laptop computing device or a desktop computer, rather than the small-form-factor personal computer of the illustrative embodiment. Also, in one or more alternative embodiments, the visual display device 710 may be in the form of a head-mounted visual display device (e.g., a display incorporated in a pair of goggles), and the user input device 724 may be in the form of a voice recognition device or a touchpad interface.

Referring again to FIG. 25, it can be seen that the illustrative vision system 700 may further include a force measurement assembly 722 for measuring the ground reaction forces and/or moments of the user. In particular, the force measurement assembly 722 may comprise a static dual force plate that is configured to rest on the floor of the room in which the system 700 is disposed (see FIG. 24). The dual force plate 722 comprises a plurality of force transducers or load cells for measuring the forces and/or moments generated on the two plate surfaces thereof by respective feet of the user. As such, the center of pressure (COP), center of gravity (COG), and/or sway angle of the user may be determined while the user undergoes training on the force measurement assembly 722. For example, in the illustrative embodiment, the dual force plate 722 may use the force plate technology described in U.S. Pat. No. 8,544,347, the entire disclosure of which is incorporated herein by reference.

In addition, as illustrated in FIG. 24, the force measurement assembly 722 is operatively coupled to the data processing device 714 by virtue of an electrical cable 723.

In one embodiment, the electrical cable 723 is used for data transmission, as well as for providing power to the force measurement assembly 722. Various types of data transmission cables can be used for cable 723. For example, the cable 723 can be a Universal Serial Bus (USB) cable or an Ethernet cable. Preferably, the electrical cable 723 contains a plurality of electrical wires bundled together, with at least one wire being used for power and at least another wire being used for transmitting data. The bundling of the power and data transmission wires into a single electrical cable 723 advantageously creates a simpler and more efficient design. In addition, it enhances the safety of the training environment for the user. However, it is to be understood that the force measurement assembly 722 can be operatively coupled to the data processing device 714 using other signal transmission means, such as a wireless data transmission system. If a wireless data transmission system is employed, it is preferable to provide the force measurement assembly 722 with a separate power supply in the form of an internal power supply or a dedicated external power supply.

Now, the acquisition and processing of the load data carried out by the illustrative embodiment of the vision testing/training system 700 will be described. Initially, a load is applied to the force measurement assembly 722 by the user disposed thereon. The load is transmitted from the first and second plate components of the dual force plate to its force transducer beams. In the illustrative embodiment, each plate component of the dual force plate is supported on a pair of force transducer beams disposed thereunder. In the illustrative invention, each of the force transducer beams includes a plurality of strain gages wired in one or more Wheatstone bridge configurations, wherein the electrical resistance of each strain gage is altered when the associated portion of the associated beam-type force transducer undergoes deformation (i.e., a measured quantity) resulting from the load (i.e., forces and/or moments) acting on the first and second plate components. For each plurality of strain gages disposed on the force transducer beams, the change in the electrical resistance of the strain gages brings about a consequential change in the output voltage of the Wheatstone bridge (i.e., a quantity representative of the load being applied to the measurement surface). Thus, in the illustrative embodiment, the pair of force transducer beams disposed under the plate components output a total of six (6) analog output voltages (signals). In the illustrative embodiment, the six (6) analog output voltages from dual force plate are then transmitted to a preamplifier board (not shown) for preconditioning. The preamplifier board is used to increase the magnitudes of the transducer analog voltages, and preferably, to convert the analog voltage signals into digital voltage signals as well. After which, the force measurement assembly 722 transmits the force plate output signals $S_{FPO1}$-$S_{FPO6}$ to a main signal amplifier/converter. Depending on whether the preamplifier board also includes an analog-to-digital (A/D) converter, the force plate output signals $S_{FPO1}$-$S_{FPO6}$ could be either in the form of analog signals or digital signals. The main signal amplifier/converter further magnifies the force plate output signals $S_{FPO1}$-$S_{FPO6}$, and if the signals $S_{FPO1}$-$S_{FPO6}$ are of the analog-type (for a case where the preamplifier board did not include an analog-to-digital (A/D) converter), it may also convert the analog signals to digital signals. In the illustrative embodiment, the force plate output signals $S_{FPO1}$-$S_{FPO6}$ may also be transformed into output forces and/or moments (e.g., $F_{Lz}$, $M_{Lx}$, $M_{Ly}$, $F_{Rz}$, $M_{Rx}$, $M_{Ry}$) by the firmware of the dual force plate by multiplying the voltage signals $S_{FPO1}$-$S_{FPO6}$ by a calibration matrix prior to the force plate output data being transmitted to the data processing device 714. Alternatively, the data acquisition/data processing device 714 may receive the voltage signals $S_{FPO1}$-$S_{FPO6}$, and then transform the signals into output forces and/or moments (e.g., $F_{Lz}$, $M_{Ly}$, $F_{Rz}$, $M_{Rx}$, $M_{Ry}$) by multiplying the voltage signals $S_{FPO1}$-$S_{FPO6}$ by a calibration matrix.

After the voltage signals $S_{FPO1}$-$S_{FPO6}$ are transformed into output forces and/or moments (e.g., $F_{Lz}$, $M_{Lx}$, $M_{Ly}$, $F_{Rz}$, $M_{Rx}$, $M_{Ry}$), the center of pressure for each foot of the user (i.e., the x and y coordinates of the point of application of the force applied to the measurement surface by each foot) may be determined by the data acquisition/data processing device 714. If the force transducer technology described in U.S. Pat. No. 8,544,347 is employed, it is to be understood that the center of pressure coordinates ($x_{P_L}$, $y_{P_L}$, $x_{P_R}$, $x_{P_R}$) can be computed in the particular manner described in that patent. Also, as described below, rather than computing two sets of center of pressure coordinates (i.e., one for each foot of the user), a single set of overall center of pressure coordinates ($x_P$, $y_P$) may be computed in one or more embodiments.

In one or more alternative embodiments, the data processing device 714 determines the vertical forces $F_{Lz}$, $F_{Rz}$ exerted on the surface of the first and second force plates by the feet of the user and the center of pressure for each foot of the user, while in another embodiment where a six component force plate is used, the output forces of the data processing device 714 includes all three (3) orthogonal components of the resultant forces acting on the two plate components (i.e., $F_{Lx}$, $F_{Ly}$, $F_{Lz}$, $F_{Rx}$, $F_{Ry}$, $F_{Rz}$) and all three (3) orthogonal components of the moments acting on the two plate components (i.e., $M_{Lx}$, $M_{Ly}$, $M_{Lz}$, $M_{Rx}$, $M_{Ry}$, $M_{Rz}$). In yet other embodiments of the invention, the output forces and moments of the data processing device 714 can be in the form of other forces and moments as well.

In the illustrative embodiment, where a single set of overall center of pressure coordinates ($x_P$, $y_P$) are determined for the force measurement assembly 722, the center of pressure of the force vector F applied by the user to the measurement surface of the force plate 722 is computed as follows:

$$x_P = \frac{-M_y}{F_Z} \quad (14)$$

$$y_P = \frac{M_x}{F_Z} \quad (15)$$

where:

$x_P$, $y_P$: coordinates of the point of application for the force (i.e., center of pressure) on the force plate assembly 722;

$F_z$: z-component of the resultant force acting on the force plate assembly 722;

$M_x$: x-component of the resultant moment acting on the force plate assembly 722; and $M_y$: y-component of the resultant moment acting on the force plate assembly 722.

In addition, in a further embodiment, the vision testing/training system 700 further comprises a data interface configured to operatively couple the data processing device 714 to a remote computing device (e.g., remote laptop or desktop computing device) so that data from the data processing device 714 is capable of being transmitted to the remote computing device. In one or more embodiments, the data interface may comprise a wireless data interface or a wired data interface operatively coupling the data processing device 714 to the remote computing device.

Now, with reference to the screen images of FIGS. 26 and 27, the vision testing/training modes carried out by the vision testing/training system 700 will be described in detail. In the illustrative embodiment, the data processing device 714 is programmed to execute each of the testing/training modes described hereinafter.

In the first testing/training mode carried out by the illustrative vision testing/training system 700, a target appears randomly on the output screen 712 of the visual display device 710 in either green or red. The user must touch the green targets and avoid the red targets. Once the user touches the target, it will disappear, and another target will appear on the output screen 712. If the user does not touch the target after a predetermined period of time has elapsed, the target will disappear and then the target will reappear after a specified time period. This process continues for the duration of the testing/training mode.

Figure 26:
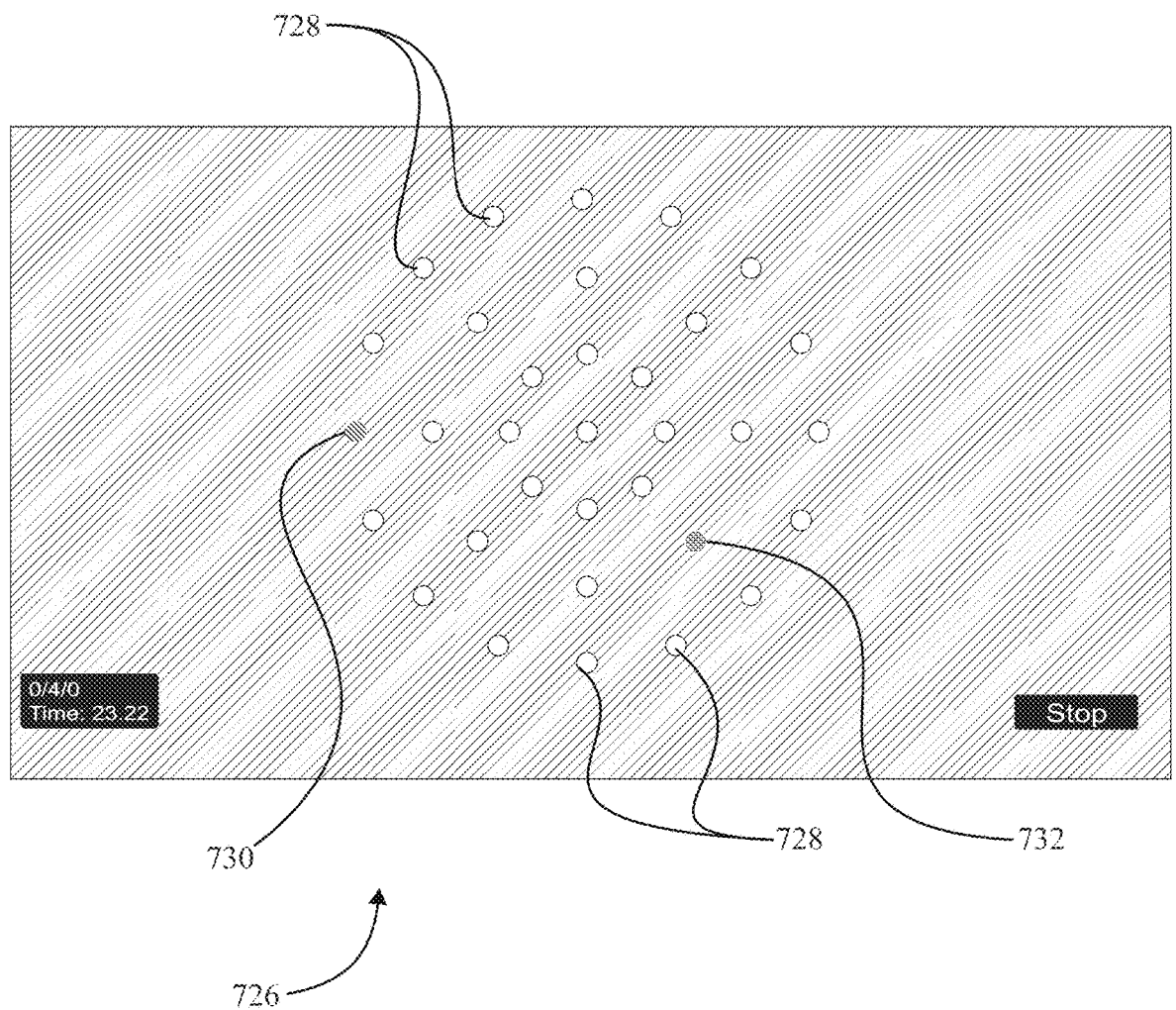
FIG. 26 is a screen image of a first testing/training mode displayed on the output screen of the visual display device of the vision testing/training system of FIG. 24.

In particular, with reference to the screen image 726 depicted in FIG. 26, in the first illustrative testing/training mode, the data processing device 714 is programmed to generate and display a plurality of visual objects on the output screen 712 of the visual display device 710 in a plurality of different sequential locations on the output screen 712. For example, as shown in FIG. 26, the targets that are generated by the data processing device 714 may appear sequentially in a plurality of different locations 728 on the output screen 712 that are arranged in a circular grid pattern. For example, in the illustrative embodiment, the user may first be presented with a first visual object having a first color or shape (e.g., a target that is green in color, which is represented by the target 730 in FIG. 26 with the diagonal hatching pattern). In this case, because the first target is in the form of a green target, the correct action to be taken by the user is to select the green target by using the user input device (e.g., the touchscreen user interface of the visual display device 710). Once the user touches the target on the touchscreen user interface of the visual display device 710, the data processing device 714 receives an input signal from the touchscreen user interface based upon an input response by the user. Then, the data processing device 714 is programmed to determine whether the user has performed the correct action by selecting the first visual object. In this case, because the first target was green, the user performed the correct action by selecting the target on the output screen 712. In addition, the data processing device 714 is programmed to determine, based upon the output signal received from the eye movement tracking device 725, whether the user is generally looking in a direction that corresponds to a location of the first target 730 on the output screen 712 of the visual display device 710. Advantageously, determining the gaze direction of the user allows the user's score for a particular vision test and/or vision training session to be correlated with the user's eye direction. The gaze direction determination also enables one to determine how the eye movement and the motor skills of the user integrate. Also, after the user touches the first green target using the touchscreen user interface of the visual display device 710, the target disappears, and a second target appears on the output screen 712. For example, in the illustrative embodiment, the user may be presented with a second visual object having a second color or shape (e.g., a target that is red in color, which is represented by the target 732 in FIG. 26 with the criss-cross hatching pattern). In this case, because the second target is in the form of a red target, the correct action to be taken by the user is to not select the red target on the output screen 712. The data processing device 714 is programmed to determine whether the user has performed the correct action by not selecting the first visual object. In this case, because the second target was red, the user performed the correct action by not selecting the target on the output screen 712. In addition, the data processing device 714 is programmed to determine, based upon the output signal received from the eye movement tracking device 725, whether the user is generally looking in a direction that corresponds to a location of the second target 732 on the output screen 712 of the visual display device 710. Also, after a predetermined time period has elapsed, the second target disappears from the output screen 712, and a third target appears on the output screen 712 for evaluation by the user (e.g., the third target may be in the form of either a red or green target). In the illustrative embodiment, the first training mode continues in this manner for a predetermined duration of time while the user is presented with either a green target requiring selection by the user or a red target requiring non-selection by the user in different locations on the output screen 712.

In one or more embodiments of the first testing/training mode carried out by the illustrative vision testing/training system 700, the one or more visual objects 730, 732 generated by the data processing device 714 and displayed on the output screen 712 of the visual display device 710 are displaced to different discrete locations on the output screen 712; and the data processing device 714 is further programmed to determine saccadic eye movements of the user (i.e., the rapid movement of the eyes of the user between fixation points) from the output signal outputted by the eye movement tracking device 725 as the user gazes at the one or more visual objects 730, 732 in the different discrete locations on the output screen 712. During saccadic testing, the user's eyes are jumping from one target to another target.

In one or more other embodiments of the first testing/training mode carried out by the illustrative vision testing/training system 700, the one or more visual objects 730, 732 generated by the data processing device 714 and displayed on the output screen 712 of the visual display device 710 are displaced in a continuous manner on the output screen 712; and the data processing device 714 is further programmed to determine smooth pursuits eye movements of the user (i.e., the opposite of saccades) from the output signal outputted by the eye movement tracking device 725 as the user attempts to follow the one or more visual objects 730, 732 being displaced on the output screen 712. In these embodiments, the eye movement tracking device 725 is used to determine how closely the eyes of the user follow a target 730, 732 on the output screen 712 of the visual display device 710.

In yet one or more other embodiments of the first testing/training mode carried out by the illustrative vision testing/training system 700, the one or more visual objects 730, 732 generated by the data processing device 714 and displayed on the output screen 712 of the visual display device 710 are displaced to different discrete locations on the output screen 712; and the data processing device 714 is further programmed to determine anti-saccadic eye movements of the user from the output signal outputted by the eye movement tracking device 725 as the user looks away from the one or more visual objects 730, 732 in the different discrete locations on the output screen 712. For example, in these one or more other embodiments, the user may be presented with one or more visual objects 730, 732 on one side of the screen, and then the user is instructed to look at the other side of the screen away from the one or more visual objects 730, 732. When a subject has sustained a concussion or has a disease, such as Parkinson's disease, dementia, Alzheimer's disease, etc., the cognitive skill during the anti-saccade test cannot overcome the reflex of the user. This type of test could be used for a return-to-play determination after a user has sustained a concussion, or it could be used for the diagnosis of one of these diseases.

In still one or more other embodiments of the first testing/training mode carried out by the illustrative vision testing/training system 700, the data processing device 714 is further programmed to: (i) determine a first vision performance score based upon an ability of the user to gaze in the direction that corresponds to the location of the one or more visual objects 730, 732 on the output screen 712 of the visual display device 710, the first vision performance score being determined using the second signal outputted by the eye movement tracking device 725; (ii) determine a second motor skills score based upon an ability of the user to perform the correct action with respect to the one or more visual objects 730, 732 displayed on the output screen 712, the second motor skills score being determined using the first signal outputted by the user input device 712, 724; and (iii) determine a combined performance score for the user as a function of the first vision performance score and the second motor skills score of the user (e.g., a combined performance score based on a summation of the first vision performance score and the second motor skills score of the user).

In yet one or more other embodiments of the first testing/training mode carried out by the illustrative vision testing/training system 700, the one or more visual objects 730, 732 generated by the data processing device 714 and displayed on the output screen 712 of the visual display device 710 comprise a series of black and white stripes that are displaced horizontally and/or vertically on the output screen 712; and the data processing device 714 is further programmed to determine optokinetic eye movements of the user from the second signal outputted by the eye movement tracking device 725 as the user gazes at the one or more visual objects 730, 732 with the series of horizontally and/or vertically displaced black and white stripes on the output screen 712. In these one or more embodiments, as the black and white stripes are displaced horizontally and/or vertically on the output screen 712, the eye movement tracking device 725 is used to determine if the eyes of the user are following the one or more visual objects 730, 732. The eye movement tracking device 725 may also be used to quantify eye movements with optokinetic patterns.

In still one or more other embodiments of the first testing/training mode carried out by the illustrative vision testing/training system 700, the data processing device 714 is further programmed to determine a visual midline shift of the user from the second signal outputted by the eye movement tracking device 725 as the user gazes at the one or more visual objects 730, 732 on the output screen 712. Visual midline shift often happens after a person has sustained a concussion. With visual midline shift, a person tends to see objects shifted to the right or left.

In yet one or more other embodiments of the first testing/training mode carried out by the illustrative vision testing/training system 700, the data processing device 714 is further programmed to determine a cognitive load (i.e., amount of working memory resources) for the user based on a pupil dilation of one or more eyes of the user determined from the second signal outputted by the eye movement tracking device 725 as the user gazes at the one or more visual objects 730, 732 on the output screen 712. For example, if a subject understands what is being said to him or her, then his or her pupil will dilate in an oscillatory manner. However, if the subject does not understand what is being said to him or her, then his or her pupil will not dilate much. As such, pupil dilation can be used in the context of a concussion test to determine if a person has sustained a concussion. If virtually no dilation is taking place when someone is talking to the person, then the person has likely sustained a concussion.

In still one or more other embodiments of the first testing/training mode carried out by the illustrative vision testing/training system 700, the one or more visual objects 730, 732 generated by the data processing device 714 and displayed on the output screen 712 of the visual display device 710 are displaced into and out of the output screen 712; and the data processing device 714 is further programmed to record eye movements of the user as the user gazes at the one or more visual objects 730, 732 being displaced into and out of the output screen 712 so that the convergence and/or divergence of the eye of the user is able to be determined. That is, the data processing device 714 uses the recording features that are available with the eye movement tracking device 725 to measure the convergence and divergence of the eyes of the user.

In yet one or more other embodiments of the first testing/training mode carried out by the illustrative vision testing/training system 700, the one or more visual objects 730, 732 generated by the data processing device 714 and displayed on the output screen 712 of the visual display device 710 are rotated in a first direction on the output screen 712; and the data processing device 714 is further programmed to determine a torsional eye movement of the user from the second signal outputted by the eye movement tracking device 725 as one or more eyes of the user rotate in a second direction as the user attempts to follow the one or more visual objects 730, 732 being rotated on the output screen 712, the second rotational direction of the one or more eyes of the user being opposite to the first rotational direction of the one or more visual objects 730, 732 on the output screen 712. For example, the torsional movement of the eye may be assessed in order to determine if a patient has vertigo.

In still one or more other embodiments of the first testing/training mode carried out by the illustrative vision testing/training system 700, the balance of the user is analyzed using the force measurement assembly 722. In these one or more embodiments, the data processing device 714 is configured to receive the one or more measurement signals that are generated based upon the user's contact with the surface of the force measurement assembly 722 and to compute one or more numerical values using the one or more measurement signals, the data processing device 714 is further configured to determine a balance parameter for the user based on the one or more computed numerical values. In these one or more embodiments, the data processing device 714 is further programmed to: (i) determine a first vision performance score based upon an ability of the user to gaze in the direction that corresponds to the location of the one or more visual objects 730, 732 on the output screen 712 of the visual display device 710, the first vision performance score being determined using the second signal outputted by the eye movement tracking device 725; (ii) determine a second motor skills score based upon an ability of the user to perform the correct action with respect to the one or more visual objects 730, 732 displayed on the output screen 712, the second motor skills score being determined using the first signal outputted by the user input device 712, 724; (iii) determine a third balance score using the balance parameter for the user determined from the one or more numerical values computed using the one or more measurement signals of the force measurement assembly 722; and (iv) determine a combined performance score for the user as a function of the first vision performance score, the second motor skills score, and the third balance score of the user. In these one or more embodiments, the eye movement tracking device 725 is used with force measurement assembly 722 and a touchscreen visual display device to measure combined eye/balance/hand assessments.

In yet one or more other embodiments of the first testing/training mode carried out by the illustrative vision testing/training system 700 (see FIGS. 24-26), the data processing device 714 is programmed to: (i) generate and display at least one visual object 730, 732 on the output screen 712 of the visual display device 710; (ii) displace the at least one visual object 730, 732 across the output screen 712 of the visual display device 710; and (iii) determine, based upon the signal received from the eye movement tracking device 725, whether the user 721 is able to accurately track the at least one visual object 730, 732 as the at least one visual object 730, 732 is displaced across the output screen 712 of the visual display device 710.

In these one or more other embodiments of the first testing/training mode carried out by the illustrative vision testing/training system 700, prior to determining whether the user 721 is able to accurately track the at least one visual object 730, 732 as the at least one visual object 730, 732 is displaced across the output screen 712 of the visual display device 710, the data processing device 714 is further programmed to maintain the at least one visual object 730, 732 in a generally stationary position on the output screen 712, and to determine whether the user 721 is able to maintain a center point of fixation of his or her eyes on the at least one visual object 730, 732 that is stationary. Also, in these one or more other embodiments, the data processing device may be programmed to generate and display the at least one visual object 730, 732 on the output screen 712 of the visual display device 710 in a pop-up manner after the at least one visual object 730, 732 is maintained in the generally stationary position on the output screen 712. In addition, in these one or more other embodiments, when determining whether the user 721 is able to maintain a center point of fixation of his or her eyes on the at least one visual object 730, 732 in the generally stationary position on the output screen 712, the data processing device 714 is further programmed to determine a degree of stability of the center point of fixation of the eyes of the user 721. That is, the data processing device 714 determines the stability of the user's central fixation when the user 721 is asked to fix his or her eyes on a target and not move. The data processing device 714 determines the ability of the eyes of the user 721 to stay on the target, and the variability of this ability is a measure of the "stability" of the eyes of the user 721 (i.e., a measure of fixational stability).

Further, in these one or more other embodiments of the first testing/training mode carried out by the illustrative vision testing/training system 700, a center point of fixation may be required on a target, which subsequently moves after an arbitrary amount of time (400 milliseconds to 5000 milliseconds). The goal is for the eyes of the user 721 to stay on the target for a given amount of time, which if successfully performed, counts as successfully "hitting" the target. In these one or more other embodiments, the performance of the user 721 in maintaining his or her pursuit eye movement is tracked.

In still one or more other embodiments of the first testing/training mode carried out by the illustrative vision testing/training system 700, the user 721 is first instructed to fixate his or her eyes at some point on the screen 712. Once that condition is satisfied for an arbitrarily selected amount of time, a target is spawned by the data processing device 714, and the user 721 makes a saccadic eye movement toward the target. The eyes of the user 721 are then required to fixate on this second target. The eye movement tracking device 725 measures the accuracy (gain) of each saccade in consecutively spawned target. Then, the data processing device 714 compares the center of fixation calculated from the eye movement tracking device 725, when the user 721 makes saccadic eye movements with the eyes and moves the center of fixation cursor to the target.

In yet one or more other embodiments of the first testing/training mode carried out by the illustrative vision testing/training system 700, the data processing device 714 is further programmed to determine whether both eyes of the user are looking at the at least one visual object 730, 732 on the output screen 712 of the visual display device 710 so as to assess binocular vision capabilities of the user 721. In these other embodiments, eye tracking is used to determine whether the eyes of the user 721 are looking at the same position on the screen 712, and thus whether there is binocular vision in response to a target being displayed on the screen 712.

In still one or more other embodiments of the first testing/training mode carried out by the illustrative vision testing/training system 700, when determining whether the user 721 is able to accurately track the at least one visual object 730, 732 as the at least one visual object 730, 732 is displaced across the output screen 712 of the visual display device 710, the data processing device 714 is programmed to determine saccadic eye movements of the user 721 from the signal outputted by the eye movement tracking device 725 as the user 721 attempts to track the at least one visual object 730, 732 as the at least one visual object 730, 732 is displaced across the output screen 712.

In yet one or more other embodiments of the first testing/training mode carried out by the illustrative vision testing/training system 700, the data processing device 714 is further programmed to determine binocular stability of the user 721 during pursuit eye movements that involve tracking the at least one visual object 730, 732, saccadic eye movements that involve tracking the at least one visual object 730, 732, and fixation of the eyes of the user on the at least one visual object 730, 732.

Figure 28:
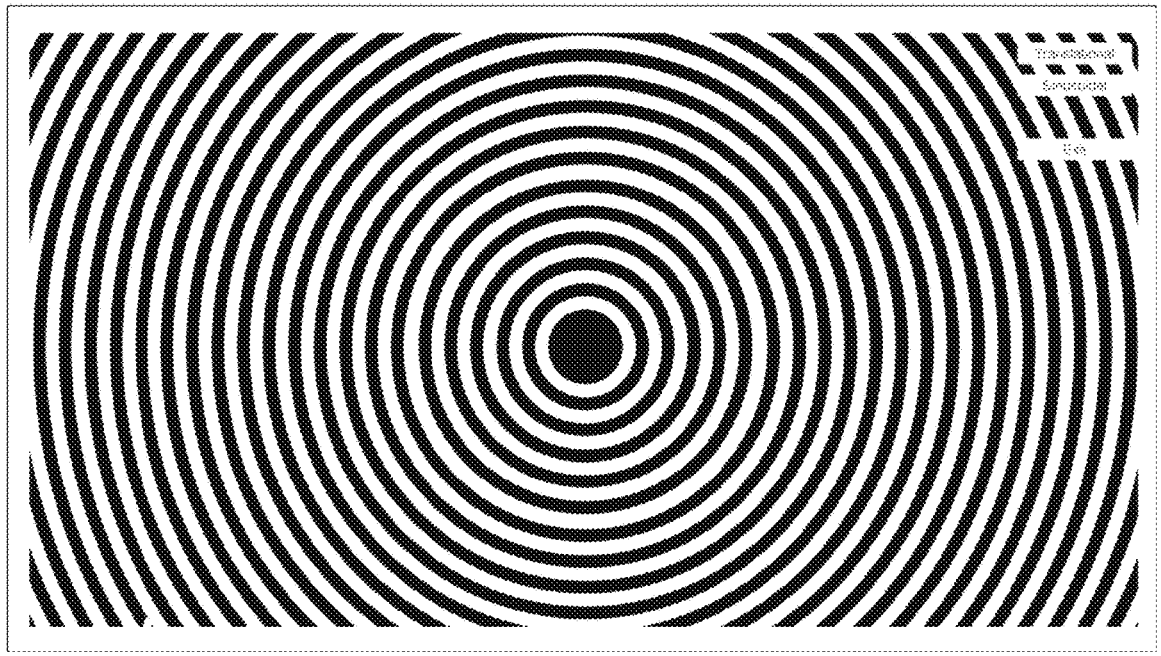
FIG. 28 is an exemplary screen image of an optic flow pattern, which may be used to create an optokinetic illusion for a user during testing or training performed using the vision testing/training system of FIG. 24.

With reference to FIG. 28, an exemplary screen image 764, which may be used during the first testing/training mode carried out by the illustrative vision testing/training system 700, is depicted. The optic flow pattern in the screen image 764 of FIG. 28 may be used during smooth pursuit eye movements that involve tracking the at least one visual object 730, 732 and/or saccadic eye movements that involve tracking the at least one visual object 730, 732. The optic flow pattern in the screen image 764 of FIG. 28 creates an optokinetic illusion for the user 721 that is able to induce illusory feelings of self-motion. During testing or training, the screen image 764 may be used as an illusory background, and the at least one visual object 730, 732 may be displaced across the illusory background. In other embodiments, rather than using the screen image 764 of FIG. 28, a star field pattern may be used as the illusory background for the user 721.

In still one or more other embodiments of the first testing/training mode carried out by the illustrative vision testing/training system 700, the system further comprises a head position measurement device (e.g., inertial measurement unit 428 described above) configured to measure an angular position of a head of the user 721. In these one or more other embodiments, the data processing device 714 is further programmed to determine an angular position of the head of the user 721 while the user 721 attempts to track the at least one visual object 730, 732 as the at least one visual object 730, 732 is displaced across the output screen 712 of the visual display device 710, and assess a performance of the user 721 based upon a combination of the angular position of the head of the user 721 determined from the head position measurement device 428 and eye tracking data determined from the eye movement tracking device 725. In these one or more embodiments, the data processing device 714 may be programmed to utilize head tracking head position in unison with eye tracking to measure the angle of head movement versus eye movement comparison in response to a target being spawned in the vision field of the patient. Also, using the output of the head position measurement device 428 and the eye movement tracking device 725, the data processing device 714 is able to determine the gaze point of the user 721 on the output screen 712 of the visual display device 710. Then, during a training routine, the user 721 may be required to fixate his or her eyes on a target while simultaneously using the center of pressure trace from the force balance plate to hover over the same target. During this training routine, the user 721 is require to hover his or her vision center point of fixation and center of pressure over the target for an arbitrary period (i.e., the user 721 is able to converge his or her vision center point of fixation and center of pressure on the same target).

In these one or more other embodiments of the first testing/training mode carried out by the illustrative vision testing/training system 700, the head position measurement device may comprise at least one of the following: (i) one or more inertial measurement units, (ii) a video camera (e.g., two or more video cameras), (iii) an infrared sensor, (iv) an ultrasonic sensor, (v) a light source configured to project a light beam onto a surface, (vi) a markerless motion capture device, (vii) a remote eye tracker, and (viii) a 3-D camera.

In these one or more other embodiments, the head position measurement device may comprise one or more video cameras configured to capture a plurality of images of a head (e.g., of a face) of a user during a vision test or vision training routine. The data processing device 402, 714 may determine a head position, head velocity, and/or head speed of the user during the vision test or vision training routine from the plurality of images of the head of the user captured by the one or more video cameras. More specifically, the data processing device 402, 714 is further programmed to determine the head position, the head velocity, and/or the head speed of the user from the plurality of images of the head of the user captured by the one or more video cameras by performing the following additional steps: (i) extracting features from the plurality of images of the head of the user for providing inputs to a trained neural network; (ii) determining one or more head poses and/or head movements of the user using the output of the trained neural network; and (iii) determining the head position, the head velocity, and/or the head speed of the user from the one or more head poses and/or head movements of the user. In these one or more other embodiments, the output of the trained neural network comprises a plurality of keypoints for facial features of the user; and the data processing device 402, 714 is further programmed to determine the one or more head poses and/or head movements of the user from the plurality of keypoints for the facial features of the user. Also, in these one or more other embodiments, the data processing device 402, 714 may be further programmed to estimate a gaze direction of the user using at least some of the plurality of keypoints for the facial features of the user outputted by the trained neural network.

For example, in these one or more other embodiments, in order to determine head position, head velocity, and/or head speed of the user from the output of the one or more video cameras, a perspective-n-Point (PnP) solution may be determined using markerless face tracking (e.g., by tracking a 3D surface of the face). The camera intrinsic parameters (e.g., focal length $f_x$ and $f_y$, principal point $c_x$ and $x_y$) of the one or more video cameras are determined from camera calibration (e.g., removing distortions of the camera). The 2D coordinates of a few points on the face of the user and 3D locations of the same points are determined from the keypoint detector of a trained neural network (e.g., a trained convolutional neural network (CNN)). For example, for an average human face, exemplary coordinates are as follows:

Tip of the nose: (0.0, 0.0, 0.0)<===Selected as the zero position of head pose,
Chin: (0.0, −330.0, −65.0),
Left corner of the left eye: (−225.0f, 170.0f, −135.0),
Right corner of the right eye: (225.0, 170.0, −135.0),
Left corner of the mouth: (−150.0, −150.0, −125.0), and
Right corner of the mouth: (150.0, −150.0, −125.0)

In this example, these points are in some arbitrary reference frame/coordinate system. This is called the world coordinates. Coordinates followed by the letter "f" are used to indicate floating point coordinates (coordinate values varying depending on face geometry of a user). Based upon the keypoints from the trained neural network (e.g., a trained convolutional neural network (CNN)), the data processing device 402, 714 is able to determine: (1) head pose estimation and (2) gaze estimation. In these one or more other embodiments, the head pose estimation may comprise a 3D pose estimation system similar to that described in U.S. Pat. No. 10,853,970, the entire disclosure of which is incorporated herein by reference.

In further embodiments, the illustrative vision testing/training system 700 collect additional sensor data from the head position measurement device 428 and the eye movement tracking device 725 (e.g., eye position and velocity, head position and velocity, body position and velocity, etc.). Also, additional metrics can be derived from this additional collected data, such as eye position/head position, eye velocity/head velocity, and the impact of body pose on metrics. In addition, other new metrics (delta, time, response/reactive time, gain) and their first and second order derivatives may be determined as well. Further, using gait/pose data, the response time based on pose, left hand versus right hand detection and midline shift data analysis may be determined. The average head velocity during a trial (head sway score) may also be determined. Center of gravity (COG) type metrics for head position and body pose may also be determined for the subject using the vision testing/training system 700.

In the second vision testing/training mode carried out by the illustrative vision testing/training system 700, the center of pressure of the user, which is determined by the data processing device 714 from the force and moment output data of the force measurement assembly 722 described above, is used to control the displacement of a cursor on the output screen 712 of the visual display device 710. In the second vision testing/training mode, the user must move the cursor into a circular zone of a target that is randomly generated on the output screen 712. Once the cursor has remained in the circular zone of the target for a user-specified amount of time, the target disappears, and is randomly generated in another location on the output screen 712 by the data processing device 714.

Figure 27:
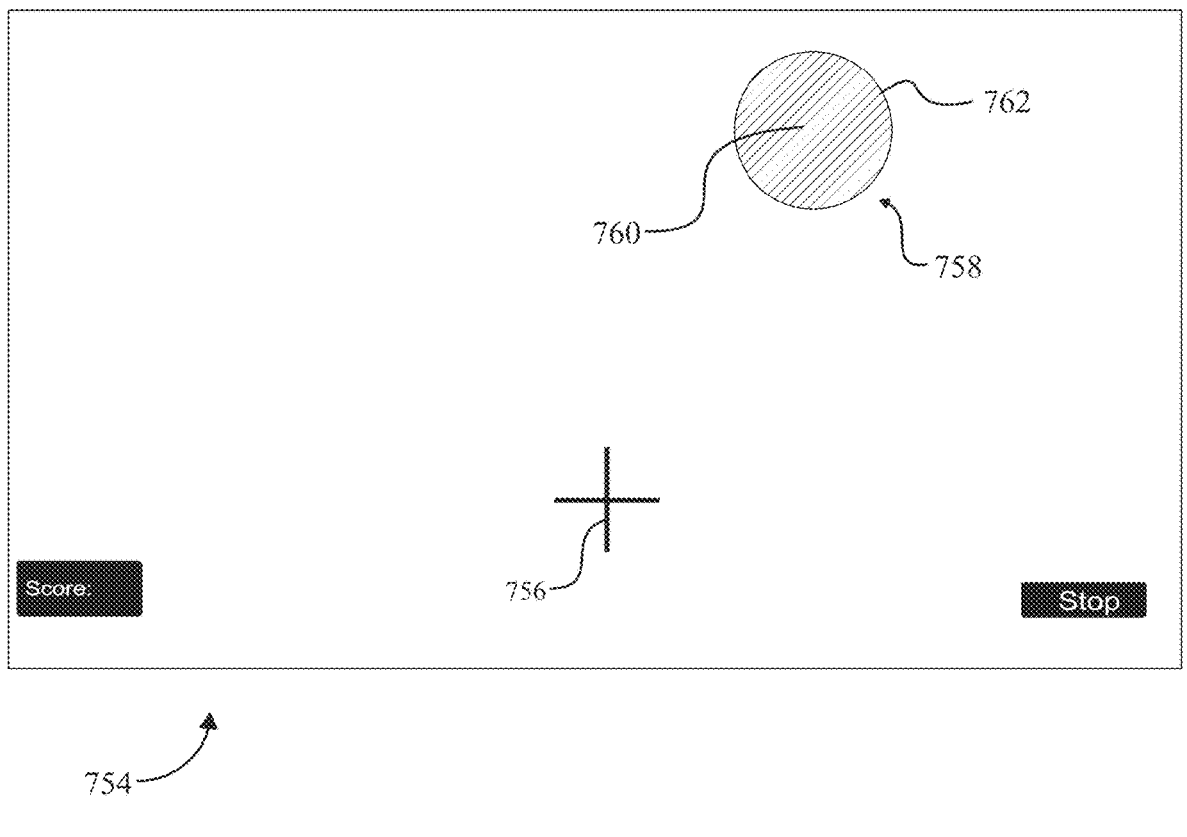
FIG. 27 is a screen image of a second testing/training mode displayed on the output screen of the visual display device of the vision testing/training system of FIG. 24.

In particular, with reference to the screen image 754 depicted in FIG. 27, in the illustrative second vision testing/training mode, the data processing device 714 is programmed to generate and display a visual target 758 defining a boundary 762 on the output screen 712 of the visual display device 710. The data processing device is further programmed to generate and display a displaceable cursor 756 on the output screen 712. In one illustrative embodiment, the user input device for the second testing/training mode comprises the force measurement assembly 722 described above. In the second testing/training mode, the center of pressure (COP) determined from the force and moment output data of the force measurement assembly 722 in the manner described above (e.g., see equations (14) and (15) above), is used to control the movement of the displaceable cursor 756 on the output screen 712 of the visual display device 710. For example, after being presented with the visual target 758 on the screen 712, the correct action to be taken by the user is to displace the cursor 756 into the interior region 760 defined by the circular boundary 762 of the visual target 758. Based upon the user's movement on the force measurement assembly 722 (i.e., shifting his weight to the right, to the left, up, or down), the cursor 756 is displaced accordingly on the screen 712 based upon the computed COP of the user. During the second testing/training mode, the data processing device 714 is programmed to determine whether the user performs the correct action by displacing the cursor 756 into the interior region 760 defined by the boundary 762 of the visual target 758. The data processing device 714 is further programmed to determine whether the displaceable cursor 756 has remained within the interior region 760 of the visual target 758 for a predetermined period of time. And, when the data processing device 714 has determined that the displaceable cursor 756 has remained within the interior region 760 of the visual target 758 for the predetermined period of time, the data processing device is additionally programmed to generate and display the visual target 758 in another random location on the output screen 712 of the visual display device 710. In the illustrative embodiment, the second testing/training mode continues in this manner for a predetermined duration of time while the user is presented with visual targets 758 in different locations on the output screen 712. For each of the visual targets 758 displayed in the second testing/training mode, the user is required to displace the cursor 756 into the interior region 760 of the visual target 758 by controlling the movement of the cursor 756 by shifting his or her weight on the force measurement assembly 722 on which he or she is standing during the second testing/training mode.

In one or more embodiments of the second testing/training mode carried out by the illustrative vision testing/training system 700, the data processing device 714 is further programmed to determine, based upon the output signal received from the eye movement tracking device 725, whether the user is generally looking in the direction that corresponds to the location of the one or more visual objects 756 on the output screen 712 of the visual display device 710 as the user moves the cursor 756 into the circular boundary 762 of the visual target 758. In these one or more embodiments, the eye movement tracking device 725 is used with eye and balance integration on the vision testing/training system 700. For example, as the cursor 756 is displaced based upon the center of pressure (COP) determined from the force measurement assembly 722, the eye movement tracking device 725 may be used to determine if the user's eyes engage in a smooth pursuits movement or a saccadic movement (i.e., a jumping movement). In these one or more embodiments, the movement of both eyes of the user and the balance of the user may be analyzed with regard to the cursor 756 on the output screen 712 of the visual display device 710. The data processing device 714 is programmed to determine if the user is looking at the cursor 756, and to determine if the user is keeping the balance cursor 756 on the visual target 758.

In one or more other embodiments of the second testing/training mode carried out by the illustrative vision testing/training system 700, the eye movement tracking device 725 may be used to control the cursor 756 rather than the force measurement assembly 722. In these one or more other embodiments, after being presented with the visual target 758 on the screen 712, the correct action to be taken by the user is to displace the cursor 756 into the interior region 760 defined by the circular boundary 762 of the visual target 758. Based upon the movement of the user's eyes measured using the eye movement tracking device 725 (i.e., moving his eyes to the right, to the left, up, or down), the cursor 756 is displaced accordingly on the screen 712 based upon the computed eye movement. In these one or more other embodiments, during the second testing/training mode, the data processing device 714 is programmed to determine whether the user performs the correct action by displacing the cursor 756 into the interior region 760 defined by the boundary 762 of the visual target 758 by using the eye movement tracking device 725 to control the position of the cursor 756. The data processing device 714 is further programmed to determine whether the displaceable cursor 756 has remained within the interior region 760 of the visual target 758 for a predetermined period of time. And, when the data processing device 714 has determined that the displaceable cursor 756 has remained within the interior region 760 of the visual target 758 for the predetermined period of time, the data processing device is additionally programmed to generate and display the visual target 758 in another random location on the output screen 712 of the visual display device 710, and the second testing/training mode proceeds in the manner described above.

In yet one or more other embodiments of the second testing/training mode carried out by the illustrative vision testing/training system 700, when the visual display device 710 is in the form of a head-mounted visual display device (e.g., a display incorporated in a pair of goggles), the displaceable cursor 756 and the visual target 758 are displayed on the head-mounted visual display device. In these one or more embodiments, the head-mounted visual display device may be in the form of a virtual reality headset or an augmented reality headset.

In still one or more other embodiments of the second testing/training mode carried out by the illustrative vision testing/training system 700, the visual display device 710 is not a touchscreen visual display device with a touchscreen user interface because the eye movement tracking device 725 is used in place of the touchscreen user interface.

In yet one or more other embodiments of the second testing/training mode carried out by the illustrative vision testing/training system 700, the data processing device 714 is programmed to independently control the center of the background or target location based on the center of fixation of the user 721. For example, a person walking through a path may be displayed on the output screen 712 of the visual display device 710, and the user 721 may control the movement of the person on the screen 712 with his or her eyes. Also, in these one or more embodiments, the data processing device 714 is programmed to independently control the center of the background to move to the center of fixation of the user 721 in real-time. Essentially, the data processing device 714 is programmed to move the background center to the new eye position, so the point of focus is always the same and the peripheral vision moves with the eye movement. Another way is to move the background to adjust to the center of fixation. If the user 721 looks left, the center shifts left, as if the user 721 is turning their head to the left. In addition, the data processing device 714 may be programmed to move the center of the background based on the eye position of the user 721. For example, if a user 721 is looking at a scene and he or she looks left, the scene follows his or her gaze and moves left such that the left side of the scene becomes the center of the screen and the new focal point for the user 721 (i.e., syncing peripheral and central vision).

In the third vision testing/training mode carried out by the illustrative vision testing/training system 700, the data processing device 714 is programmed to compute a plurality of numerical values using the one or more signals that are generated based upon the user's contact with the surface of the force measurement assembly 722 (see FIGS. 24 and 25). The data processing device 714 is further programmed to control a movement parameter of at least one visual object 730, 732 on the output screen 712 of the visual display device 710 by using a first one of the plurality of numerical values (see FIG. 26), and to assess the probability that the user 721 will fall based upon a combination of the first one of the plurality of numerical values and a second one of the plurality of numerical values.

In the third vision testing/training mode carried out by the illustrative vision testing/training system 700, the first one of the plurality of numerical values computed using the one or more signals of the force measurement assembly 722 comprise x and/or y coordinates specifying the center of pressure of a force vector applied by the user 721 on the force measurement assembly 722, and the movement parameter of the at least one visual object 730, 732 on the output screen 712 of the visual display device 710 is controlled by a fore/aft displacement of the center of pressure of the user 721 on the force measurement assembly 722. In other embodiments, rather than using a force measurement assembly 722, a balance measurement assembly also may be used in the vision testing/training system 700 to generate the plurality of numerical values.

In one or more embodiments of the third vision testing/training mode carried out by the illustrative vision testing/training system 700, the movement parameter of the at least one visual object 730, 732 on the output screen 712 of the visual display device 710 comprises a speed or acceleration of the at least one visual object 730, 732 in an interactive game, a virtual reality scenario, and/or an immersive graphic environment.

In one or more other embodiments of the third vision testing/training mode carried out by the illustrative vision testing/training system 700, the movement parameter of the at least one visual object 730, 732 on the output screen 712 of the visual display device 710 comprises a displacement of the at least one visual object 730, 732 in an interactive game, a virtual reality scenario, and/or an immersive graphic environment.

In one or more embodiments of the third vision testing/training mode carried out by the illustrative vision testing/training system 700, the second one of the plurality of numerical values computed using the one or more signals comprise a shear force applied by the user 721 on the force measurement assembly 722, and the data processing device 714 is configured to assess the probability that the user 721 will fall based upon a combination of the center of pressure of the user and the shear force applied by the user 721 on the force measurement assembly 722.

In one or more embodiments of the third vision testing/training mode carried out by the illustrative vision testing/training system 700, a turning direction of the at least one visual object 730, 732 on the output screen 712 of the visual display device 710 to the right or left is controlled by a lateral displacement of the center of pressure of the user 721 on the force measurement assembly 722.

It is apparent from the above detailed description that the vision testing/training systems 400, 401, 700 and the methods performed thereby significantly advance the field of vision and vestibular assessment. For example, the vision testing/training systems 400, 401, 700 described herein implement a customizable and accurate protocol for testing/training the vestibulo-ocular reflex (VOR) and/or visual motor performance of a subject. In addition, the method described herein accurately tests the vestibulo-ocular reflex (VOR) and/or visual motor performance of a subject by utilizing a test that is customized for the particular subject being tested.

In accordance with still a further illustrative embodiment of the invention, a neurocognitive training system for improving visual motor responses of individuals having impairments and/or athletes seeking performance enhancement is disclosed.

Hereinafter, the neurocognitive training system is described herein, in an exemplary manner, with reference to computer system architecture and exemplary processes carried out by the computer system. In one or more embodiments, the functionality described herein can be implemented by computer system instructions. These computer program instructions may be loaded directly onto an internal data storage device of a computing device (e.g., an internal data storage device of a tablet computing device). Alternatively, these computer program instructions could be stored on a portable computer-readable medium (e.g., a flash drive, etc.), and then subsequently loaded onto a computing device such that the instructions can be executed thereby. In other embodiments, these computer program instructions could be embodied in the hardware of the computing device, rather than in the software thereof. It is also possible for the computer program instructions to be embodied in a combination of both the hardware and the software.

This description describes in general form the computer program(s) required to carry out the neurocognitive training and/or testing of a user. Any competent programmer in the field of information technology could develop a system using the description set forth herein.

For the sake of brevity, conventional computer system components, conventional data networking, and conventional software coding will not be described in detail herein. Also, it is to be understood that the connecting lines shown in the block diagram(s) included herein are intended to represent functional relationships and/or operational couplings between the various components. In addition to that which is explicitly depicted, it is to be understood that many alternative or additional functional relationships and/or physical connections may be incorporated in a practical application of the system.

1. Illustrative Neurocognitive Training System

Figure 29:
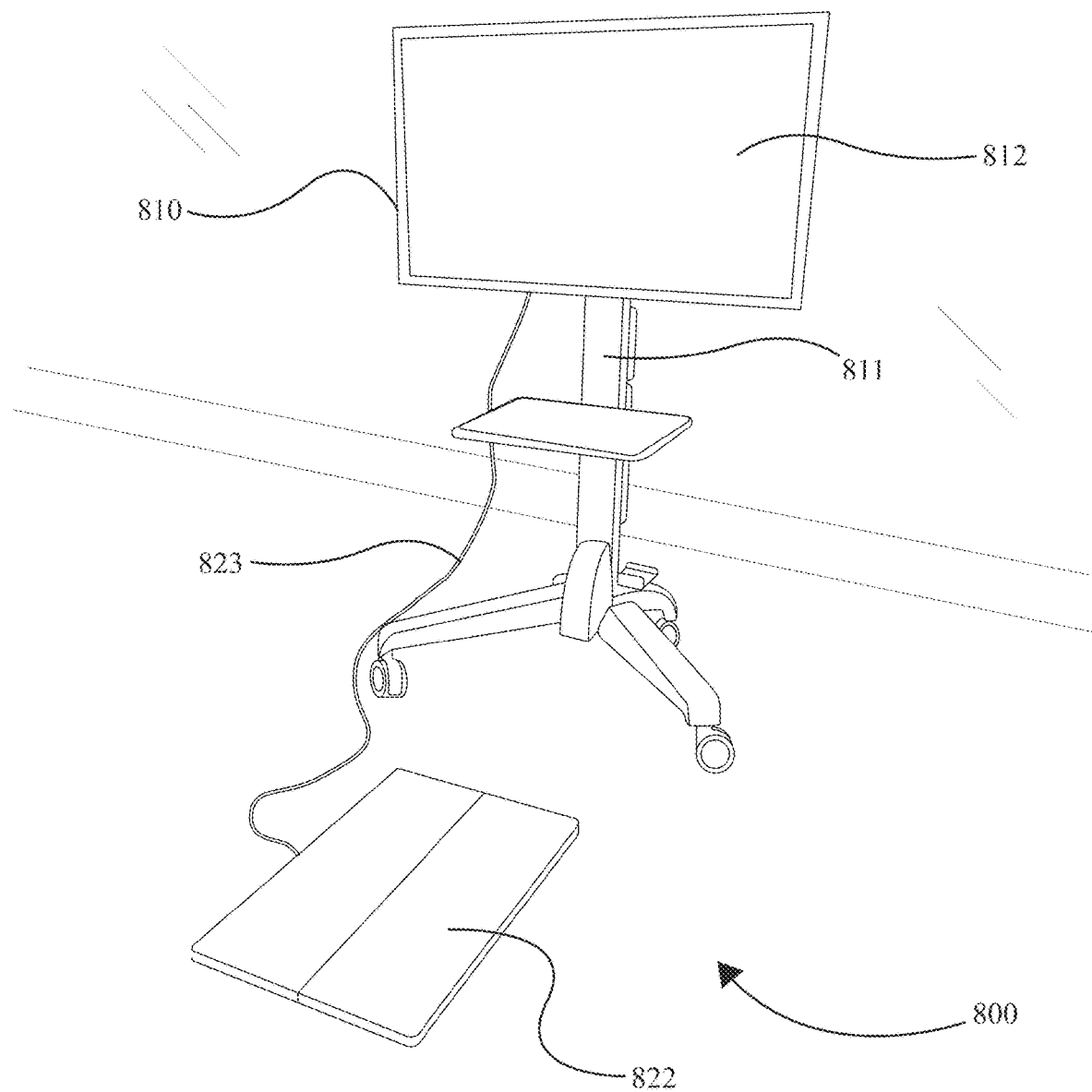
FIG. 29 is a diagrammatic perspective view of a neurocognitive training system, according to an illustrative embodiment of the invention.
Figure 30:
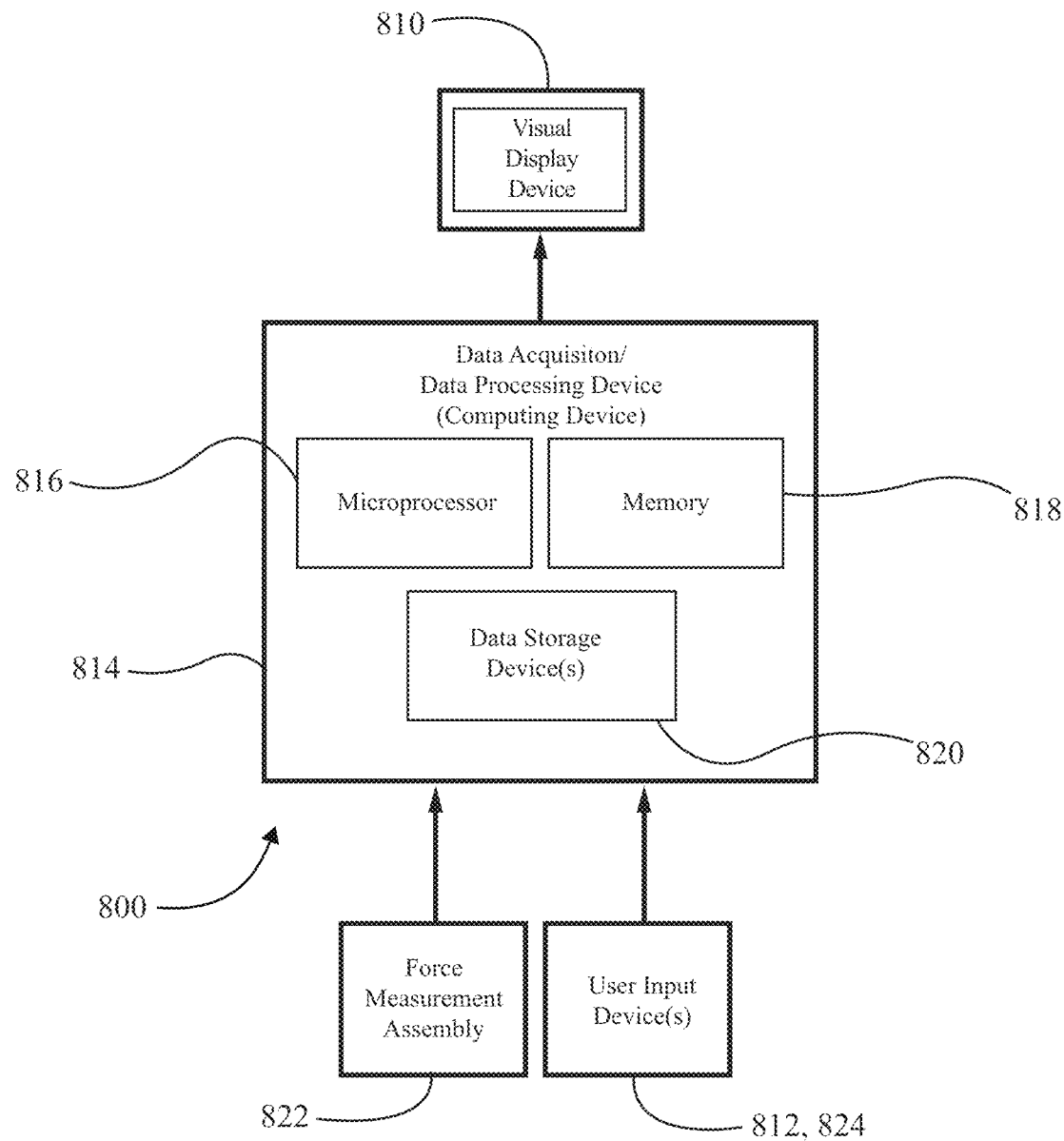
FIG. 30 is a block diagram of constituent components that may be utilized in the illustrative embodiment of the neurocognitive training system described herein.

An illustrative embodiment of the neurocognitive training system is seen generally at 800 in FIGS. 29 and 30. In the illustrative embodiment, the neurocognitive training system 800 generally comprises a visual display device 810 and a data processing device and/or data processing and data acquisition device 814 (e.g., a computing device or a small-form-factor personal computer, such as the Intel® NUC). The small-form-factor personal computer 814 is one illustrative form of a data processing device and/or data processing and data acquisition device. In FIG. 29, the small-form-factor personal computer 814 may be mounted on the back of the visual display device 810 (e.g., mounted on the back panel of a touchscreen visual display device with output screen 812). In one or more embodiments, the screen images of the training modes described hereinafter are displayed on the output screen 812 of the visual display device 810 so that the user is able to interact with one or more visual objects in the screen images.

In the illustrative embodiment of FIG. 29, the visual display device 810 is disposed on an adjustable height stand or cart 811 so that the height of the visual display device 810 is selectively adjustable by a user. Advantageously, prior to the training session of the user, the height of the stand 811 may be adjusted such that the approximate center of the visual display device 810 is generally horizontally aligned with the eyes of the standing user (i.e., so the user is generally looking at the central portion of the visual display device 810 during the training).

As shown in the illustrative block diagram of FIG. 30, the neurocognitive training system 800 further includes one or more user input devices 812, 824. The user input device 812, 824 is configured to output a signal based upon an input response by a user. In the illustrative embodiment, the user input device 812 may comprise the touchscreen user interface of the visual display device 810. In other embodiments, the user input device may alternatively comprise at least one of: (i) a voice recognition device, (ii) a wireless remote control with one or more buttons, (iii) a keyboard (i.e., a virtual or physical keyboard), (iv) a clicking device, (v) a joystick, and (vi) a pointing device. Also, in one or more further embodiments, the primary user input device 812 may comprise the touchscreen user interface of the visual display device 810, and the supplementary user input device 824 may comprise one of: (i) a voice recognition device, (ii) a wireless remote control with one or more buttons, (iii) a keyboard (i.e., a virtual or physical keyboard), (iv) a clicking device, (v) a joystick, and (vi) a pointing device.

In the illustrative embodiment, during the neurocognitive training of the user, the user may use the user input device 812, 824 in order to enter and transmit his or her response to the data processing device 814 (e.g., the selection of a particular visual object on the output screen 812 of the visual display device 810).

Now, turning again to FIG. 30, it can be seen that the data processing device 814 (e.g., the small-form-factor personal computer 814) of the neurocognitive training system 800 comprises a microprocessor 816 for processing data, memory 818 (e.g., random access memory or RAM) for storing data during the processing thereof, and data storage device(s) 820, such as one or more internal solid state drives, external flash drives, or any combination thereof. As shown in FIG. 30, the visual display device 810 is operatively coupled to the computing device 814 such that data is capable of being transferred between these devices (e.g., the visual display device 810 may be a touchscreen visual display device with a touchscreen user interface as described above). Also, as illustrated in FIG. 30, one or more data input devices 812, 824, such as the touchscreen user interface or a voice recognition sensor are operatively coupled to the computing device 814 so that a user is able to enter data into the computing device 814. In one or more alternative embodiments, the computing device 814 may be in the form of a laptop computing device or a desktop computer, rather than the small-form-factor personal computer of the illustrative embodiment. Also, in one or more alternative embodiments, the visual display device 810 may be in the form of a head-mounted visual display device (e.g., a display incorporated in a pair of goggles), and the user input device 824 may be in the form of a voice recognition device or a touchpad interface.

Referring again to FIG. 30, it can be seen that the illustrative neurocognitive training system 800 may further include a force measurement assembly 822 for measuring the ground reaction forces and/or moments of the user. In particular, the force measurement assembly 822 may comprise a static dual force plate that is configured to rest on the floor of the room in which the system 800 is disposed. The dual force plate 822 comprises a plurality of force transducers or load cells for measuring the forces and/or moments generated on the two plate surfaces thereof by respective feet of the user. As such, the center of pressure (COP), center of gravity (COG), and/or sway angle of the user may be determined while the user undergoes training on the force measurement assembly 822. For example, in the illustrative embodiment, the dual force plate 822 may use the force plate technology described in U.S. Pat. No. 8,544,347, the entire disclosure of which is incorporated herein by reference.

In addition, as illustrated in FIG. 29, the force measurement assembly 822 is operatively coupled to the data processing device 814 by virtue of an electrical cable 823. In one embodiment, the electrical cable 823 is used for data transmission, as well as for providing power to the force measurement assembly 822. Various types of data transmission cables can be used for cable 823. For example, the cable 823 can be a Universal Serial Bus (USB) cable or an Ethernet cable. Preferably, the electrical cable 823 contains a plurality of electrical wires bundled together, with at least one wire being used for power and at least another wire being used for transmitting data. The bundling of the power and data transmission wires into a single electrical cable 823 advantageously creates a simpler and more efficient design. In addition, it enhances the safety of the training environment for the user. However, it is to be understood that the force measurement assembly 822 can be operatively coupled to the data processing device 814 using other signal transmission means, such as a wireless data transmission system. If a wireless data transmission system is employed, it is preferable to provide the force measurement assembly 822 with a separate power supply in the form of an internal power supply or a dedicated external power supply.

Now, the acquisition and processing of the load data carried out by the illustrative embodiment of the neurocognitive training system 800 will be described. Initially, a load is applied to the force measurement assembly 822 by the user disposed thereon. The load is transmitted from the first and second plate components of the dual force plate to its force transducer beams. In the illustrative embodiment, each plate component of the dual force plate is supported on a pair of force transducer beams disposed thereunder. In the illustrative invention, each of the force transducer beams includes a plurality of strain gages wired in one or more Wheatstone bridge configurations, wherein the electrical resistance of each strain gage is altered when the associated portion of the associated beam-type force transducer undergoes deformation (i.e., a measured quantity) resulting from the load (i.e., forces and/or moments) acting on the first and second plate components. For each plurality of strain gages disposed on the force transducer beams, the change in the electrical resistance of the strain gages brings about a consequential change in the output voltage of the Wheatstone bridge (i.e., a quantity representative of the load being applied to the measurement surface). Thus, in the illustrative embodiment, the pair of force transducer beams disposed under the plate components output a total of six (6) analog output voltages (signals). In the illustrative embodiment, the six (6) analog output voltages from dual force plate are then transmitted to a preamplifier board (not shown) for preconditioning. The preamplifier board is used to increase the magnitudes of the transducer analog voltages, and preferably, to convert the analog voltage signals into digital voltage signals as well. After which, the force measurement assembly 822 transmits the force plate output signals $S_{FPO1}$-$S_{FPO6}$ to a main signal amplifier/converter. Depending on whether the preamplifier board also includes an analog-to-digital (A/D) converter, the force plate output signals $S_{FPO1}$-$S_{FPO6}$ could be either in the form of analog signals or digital signals. The main signal amplifier/converter further magnifies the force plate output signals $S_{FPO1}$-$S_{FPO6}$, and if the signals $S_{FPO1}$-$S_{FPO6}$ are of the analog-type (for a case where the preamplifier board did not include an analog-to-digital (A/D) converter), it may also convert the analog signals to digital signals. In the illustrative embodiment, the force plate output signals $S_{FPO1}$-$S_{FPO6}$ may also be transformed into output forces and/or moments (e.g., $F_{Lz}$, $M_{Lx}$, $M_{Ly}$, $F_{Rz}$, $M_{Rx}$, $M_{Ry}$) by the firmware of the dual force plate by multiplying the voltage signals $S_{FPO1}$-$S_{FPO6}$ by a calibration matrix prior to the force plate output data being transmitted to the data processing device 814. Alternatively, the data acquisition/data processing device 814 may receive the voltage signals $S_{FPO1}$-$S_{FPO6}$, and then transform the signals into output forces and/or moments (e.g., $F_{Lz}$, $M_{Ly}$, $F_{Rz}$, $M_{Rx}$, $M_{Ry}$) by multiplying the voltage signals $S_{FPO1}$-$S_{FPO6}$ by a calibration matrix.

After the voltage signals $S_{FPO1}$-$S_{FPO6}$ are transformed into output forces and/or moments (e.g., $F_{Lz}$, $M_{Lx}$, $M_{Ly}$, $F_{Rz}$, $M_{Rx}$, $M_{Ry}$), the center of pressure for each foot of the user (i.e., the x and y coordinates of the point of application of the force applied to the measurement surface by each foot) may be determined by the data acquisition/data processing device 814. If the force transducer technology described in U.S. Pat. No. 8,544,347 is employed, it is to be understood that the center of pressure coordinates ($x_{P_L}$, $y_{P_L}$, $x_{P_R}$, $x_{P_R}$) can be computed in the particular manner described in that patent. Also, as described below, rather than computing two sets of center of pressure coordinates (i.e., one for each foot of the user), a single set of overall center of pressure coordinates ($x_P$, $y_P$) may be computed in one or more embodiments.

In one or more alternative embodiments, the data processing device 814 determines the vertical forces $F_{Lz}$, $F_{Rz}$ exerted on the surface of the first and second force plates by the feet of the user and the center of pressure for each foot of the user, while in another embodiment where a six component force plate is used, the output forces of the data processing device 814 includes all three (3) orthogonal components of the resultant forces acting on the two plate components (i.e., $F_{Lx}$, $F_{Ly}$, $F_{Lz}$, $F_{Rx}$, $F_{Ry}$, $F_{Rz}$) and all three (3) orthogonal components of the moments acting on the two plate components (i.e., $M_{Lx}$, $M_{Ly}$, $M_{Lz}$, $M_{Rx}$, $M_{Ry}$, $M_{Rz}$). In yet other embodiments of the invention, the output forces and moments of the data processing device 814 can be in the form of other forces and moments as well.

In the illustrative embodiment, where a single set of overall center of pressure coordinates ($x_P$, $y_P$) are determined for the force measurement assembly 822, the center of pressure of the force vector $\vec{F}$ applied by the user to the measurement surface of the force plate 822 is computed as follows:

$$x_P = \frac{-M_y}{F_Z} \quad (16)$$

$$y_P = \frac{M_x}{F_Z} \quad (17)$$

where:

$x_P$, $y_P$: coordinates of the point of application for the force (i.e., center of pressure) on the force plate assembly 822;

$F_z$: z-component of the resultant force acting on the force plate assembly 822;

$M_x$: x-component of the resultant moment acting on the force plate assembly 822; and $M_y$: y-component of the resultant moment acting on the force plate assembly 822.

In addition, in a further embodiment, the neurocognitive training system 800 further comprises a data interface configured to operatively couple the data processing device 814 to a remote computing device (e.g., remote laptop or desktop computing device) so that data from the data processing device 814 is capable of being transmitted to the remote computing device. In one or more embodiments, the data interface may comprise a wireless data interface or a wired data interface operatively coupling the data processing device 814 to the remote computing device.

2. Neurocognitive Training Modes of the Neurocognitive Training System

Now, with reference to the screen images of FIGS. 31-36, the neurocognitive training modes carried out by the neurocognitive training system 800 will be described in detail. In the illustrative embodiment, the data processing device 814 is programmed to execute each of the training modes described hereinafter.

In the first training mode carried out by the illustrative neurocognitive training system 800, a target appears randomly on the output screen 812 of the visual display device 810 in either green or red. The user must touch the green targets and avoid the red targets. Once the user touches the target, it will disappear, and another target will appear on the output screen 812. If the user does not touch the target after a predetermined period of time has elapsed, the target will disappear and then the target will reappear after a specified time period. This process continues for the duration of the training mode.

Figure 31:
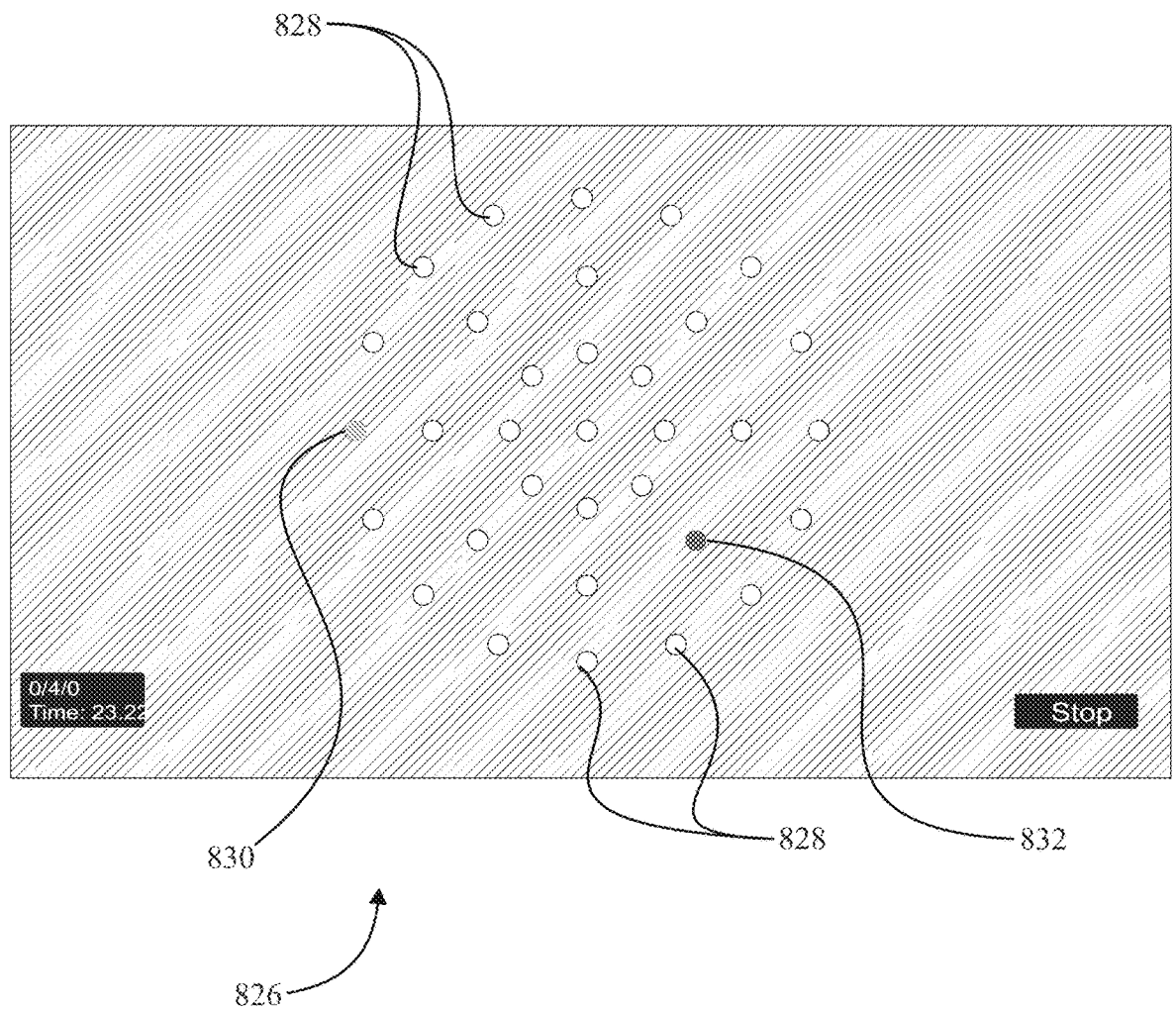
FIG. 31 is a screen image of a first training mode displayed on the output screen of the visual display device of the neurocognitive training system, according to the illustrative embodiment of the invention.

In particular, with reference to the screen image 826 depicted in FIG. 31, in the first illustrative training mode, the data processing device 814 is programmed to generate and display a plurality of visual objects on the output screen 812 of the visual display device 810 in a plurality of different sequential locations on the output screen 812. For example, as shown in FIG. 31, the targets that are generated by the data processing device 814 may appear sequentially in a plurality of different locations 828 on the output screen 812 that are arranged in a circular grid pattern. For example, in the illustrative embodiment, the user may first be presented with a first visual object having a first color or shape (e.g., a target that is green in color, which is represented by the target 830 in FIG. 31 with the diagonal hatching pattern). In this case, because the first target is in the form of a green target, the correct action to be taken by the user is to select the green target by using the user input device (e.g., the touchscreen user interface of the visual display device 810).

Once the user touches the target on the touchscreen user interface of the visual display device 810, the data processing device 814 receives an input signal from the touchscreen user interface based upon an input response by the user. Then, the data processing device 814 is programmed to determine whether the user has performed the correct action by selecting the first visual object. In this case, because the first target was green, the user performed the correct action by selecting the target on the output screen 812. Also, after the user touches the first green target using the touchscreen user interface of the visual display device 810, the target disappears, and a second target appears on the output screen 812. For example, in the illustrative embodiment, the user may be presented with a second visual object having a second color or shape (e.g., a target that is red in color, which is represented by the target 832 in FIG. 31 with the criss-cross hatching pattern). In this case, because the second target is in the form of a red target, the correct action to be taken by the user is to not select the red target on the output screen 812. The data processing device 814 is programmed to determine whether the user has performed the correct action by not selecting the first visual object. In this case, because the second target was red, the user performed the correct action by not selecting the target on the output screen 812. Also, after a predetermined time period has elapsed, the second target disappears from the output screen 812, and a third target appears on the output screen 812 for evaluation by the user (e.g., the third target may be in the form of either a red or green target). In the illustrative embodiment, the first training mode continues in this manner for a predetermined duration of time while the user is presented with either a green target requiring selection by the user or a red target requiring non-selection by the user in different locations on the output screen 812.

In the second training mode carried out by the illustrative neurocognitive training system 800, the user is presented a number of targets in a grid pattern for a set time period. After the time period has elapsed, the targets disappear from the output screen 812, and the user must repeat the pattern by touching the grid locations where the targets were presented, and replicating the sequence in which the targets were presented. This process continues for the duration of the training mode with targets being arranged in different patterns during each trial of the training mode.

Figure 32:
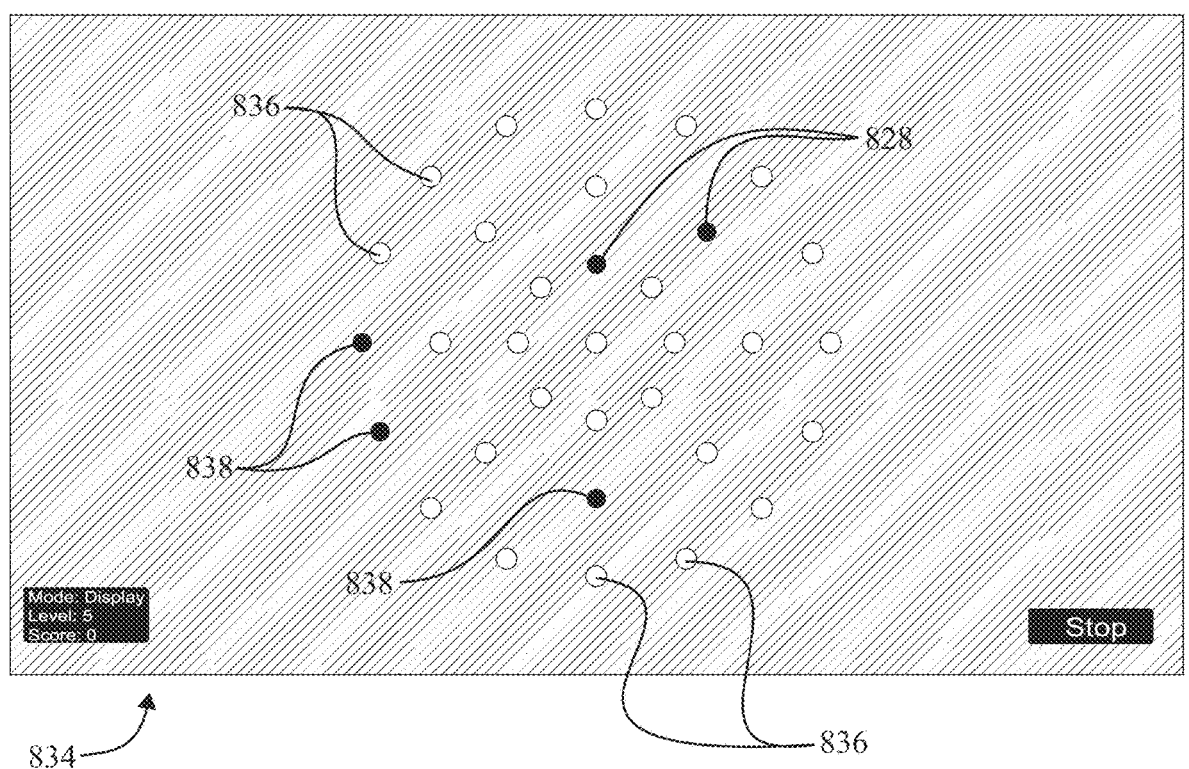
FIG. 32 is a screen image of a second training mode displayed on the output screen of the visual display device of the neurocognitive training system, according to the illustrative embodiment of the invention.

In particular, with reference to the screen image 834 depicted in FIG. 32, in the second illustrative training mode, the data processing device 814 is programmed to generate and display a plurality of visual objects on the output screen 812 of the visual display device 810 arranged in a predetermined pattern for a predetermined period of time. For example, as shown in FIG. 32, the targets 838 that are generated by the data processing device 814 may be arranged in a predetermined grid pattern (e.g., the targets 838 may be disposed in any of the locations 836 in the circular grid pattern of FIG. 32). In the illustrative embodiment of FIG. 32, it can be seen that a total of five (5) targets 838 are presented on the output screen 812 for identification by the user. After the predetermined period of time for display of the targets 838 has elapsed, the data processing device 814 is programmed to remove the plurality of targets 838 from the output screen 812 and receive input signals from the user input device (e.g., the touchscreen user interface of the visual display device 810) based upon input responses by the user that are indicative of the user's perceived replication of the location and sequence of the plurality of targets 838 arranged in the predetermined pattern. That is, the user selects the positions on the output screen 812 where he or she believes the targets 838 were located, and the user selects the positions in sequence in which he or she believes the targets 838 were presented. Then, the data processing device 814 is programmed to determine, based upon the input signals received from the user input device, whether the user has correctly identified the location and sequence of the plurality of targets 838 arranged in the predetermined grid pattern. In the illustrative embodiment, the second training mode continues in this manner for a predetermined duration of time while the user is presented with different quantities of targets that are arranged in varying grid patterns on the output screen 812 for identification by the user.

In the third training mode carried out by the illustrative neurocognitive training system 800, targets appearing sequentially on the output screen 812 of the visual display device 810 get progressively closer to the color of the background throughout the duration of the training mode. In this third training mode, the primary objective is to train the contrast sensitivity of the user (e.g., the athlete).

Figure 33:
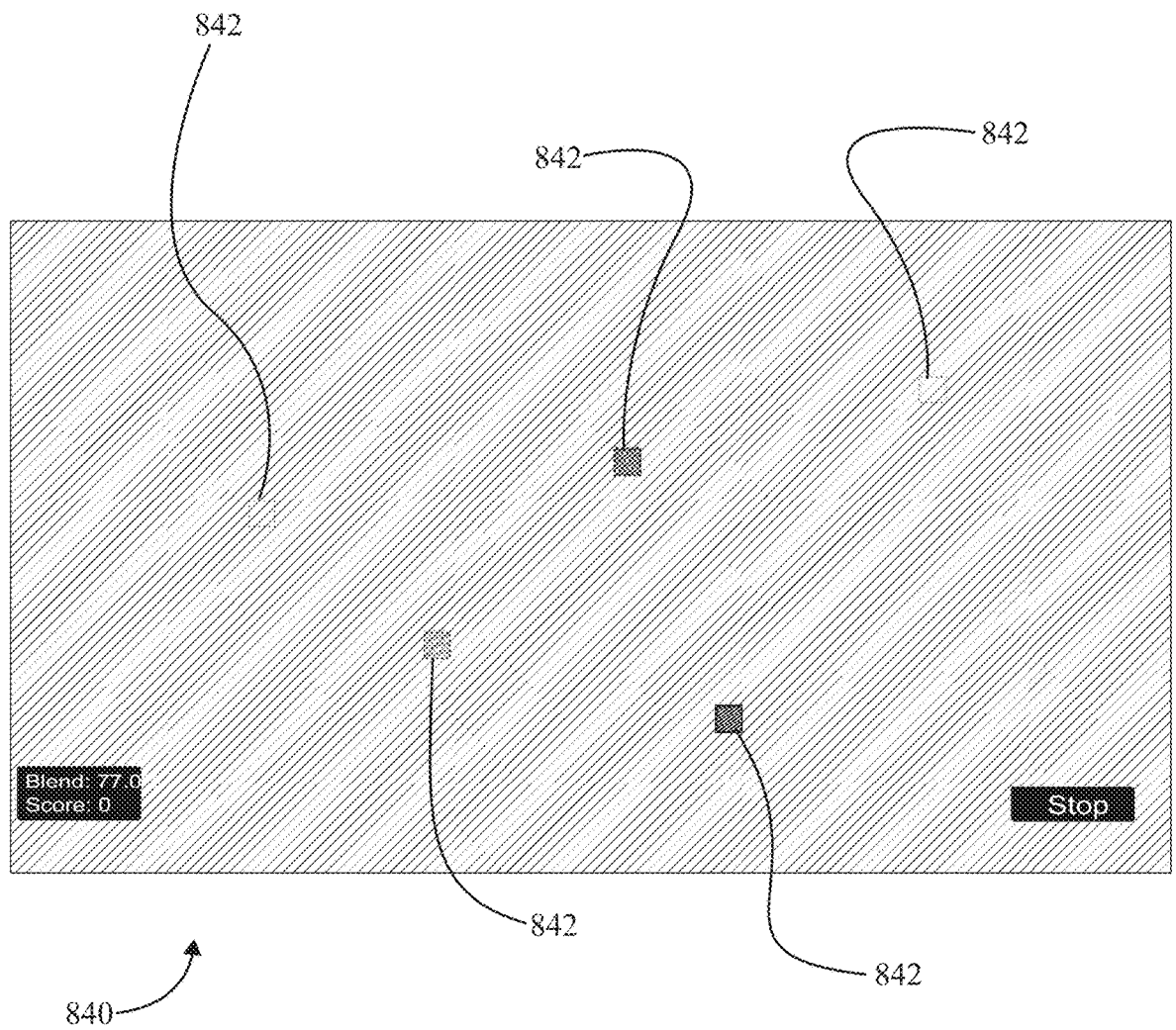
FIG. 33 is a screen image of a third training mode displayed on the output screen of the visual display device of the neurocognitive training system, according to the illustrative embodiment of the invention.

In particular, with reference to the screen image 840 depicted in FIG. 33, in the illustrative third training mode, the data processing device 814 is programmed to generate and display a plurality of visual objects on the output screen 812 of the visual display device 810 in a plurality of different sequential locations on the output screen 812. For example, as shown in FIG. 33, the targets 842 that are generated by the data processing device 814 may appear sequentially in a plurality of different locations on the output screen 812 (e.g., the target 842 depicted in the darker color in FIG. 33 is displayed first on the screen 812, then the targets 842 depicted in lighter colors in FIG. 33 are displayed sequentially after the first target 842). In the third training mode, the contrast between the targets 842 and the screen background is progressively reduced such that the targets 842 become increasing more difficult for the user to identify. For example, in the illustrative embodiment, the user may first be presented with the first target 842 (e.g., the target 842 depicted in the darkest color in FIG. 33) that has a particular color which is easily distinguishable from the screen background (e.g., a first target with a bright red color that is easily distinguishable from a black background color). After being presented with the target 842 on the screen 812, the correct action to be taken by the user is to select the target 842 by using the user input device (e.g., the touchscreen user interface of the visual display device 810). Once the user touches the target 842 on the touchscreen user interface of the visual display device 810, the data processing device 814 receives an input signal from the touchscreen user interface based upon an input response by the user. Then, the data processing device 814 is programmed to determine whether the user has performed the correct action by selecting the first target 842. Also, after the user touches the first target 842 using the touchscreen user interface of the visual display device 810, the target 842 disappears, and a second target 842 with a reduced contrast appears on the output screen 812 (e.g., one of the targets 842 in lighter colors in FIG. 33). For example, in the illustrative embodiment, the second target 842 having the reduced contrast may be a darker shade of red that is harder for the user to distinguish from the black screen background. In the illustrative embodiment, the third training mode continues in this manner for a predetermined duration of time while the user is presented with targets 842 having successively reduced contrast compared to the screen background. That is, in the illustrative third training mode, the data processing device 814 is programmed to continually reduce the contrast between the targets 842 and the screen background by progressively making a color of the one or more visual objects closer to a background color of the screen background (e.g., starting with a target 842 that is bright red, and then gradually changing the color of the target 842 such that it becomes closer and closer to the black background color).

In the fourth training mode carried out by the illustrative neurocognitive training system 800, single or multiple pairs of orbiting targets appear on the output screen 812 of the visual display device 810. The user must track one of the targets in each pair as they are displaced in an orbital path for a predetermined time period. Once the time period is over, the orbiting ceases and the user must identify the target or targets that he or she was tracking. This process continues for the duration of the training mode with orbiting targets being arranged in different patterns during each trial of the training mode.

Figure 34:
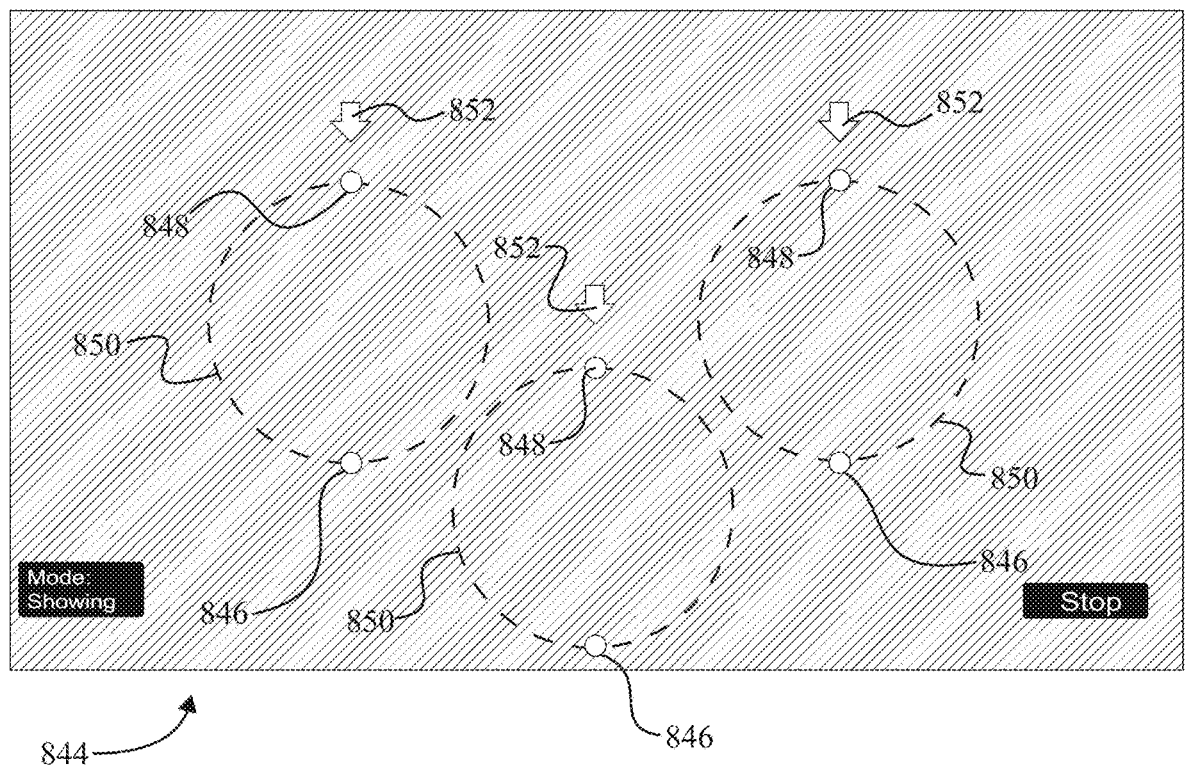
FIG. 34 is a screen image of a fourth training mode displayed on the output screen of the visual display device of the neurocognitive training system, according to the illustrative embodiment of the invention.

In particular, with reference to the screen image 844 depicted in FIG. 34, in the fourth illustrative training mode, the data processing device 814 is programmed to generate and display one or more pairs of displaceable visual objects 846, 848 on the output screen 812 of the visual display device 810. The one or more pairs of displaceable visual objects 846, 848 are configured to continually orbit in a predetermined path on the output screen 812 of the visual display device 810. For example, as shown in FIG. 34, the three (3) pairs of displaceable visual targets 846, 848 orbit in respective circular orbit paths 850. In FIG. 34, arrows 852 are used to identify the three (3) displaceable visual targets 848 that are to be followed by the user during the trial of the training mode. The three (3) displaceable visual targets 846 orbit about the same circular paths 850 as the displaceable visual targets 848, but they are not to be followed by the user. After the displaceable visual targets 846, 848 have orbited in the circular path 850 for a predetermined period of time, the data processing device 814 is programmed to stop the orbital movement of the displaceable visual targets 846, 848 so that the user is able to identify the displaceable visual targets 848. The data processing device 814 is programmed to receive input signals from the user input device (e.g., the touchscreen user interface of the visual display device 810) based upon input responses by the user that are indicative of the user's perceived identification of the orbiting visual targets 848. That is, the user selects the targets on the output screen 812 that he or she believes are the orbiting visual targets 848. A selection of any one of the orbiting visual targets 846 by the user constitutes an incorrect answer because they are not the targets that the user is required to follow on the output screen 812. Then, the data processing device 814 is programmed to determine, based upon the input signals received from the user input device, whether the user has correctly identified the orbiting visual targets 848 that have been displaced in the orbital paths 850 on the output screen 812 of the visual display device 810. In the illustrative embodiment, the fourth training mode continues in this manner for a predetermined duration of time while the user is presented with different quantities and patterns of orbiting targets to track and identify using the user input device (e.g., the touchscreen user interface of the visual display device 810).

In the fifth training mode carried out by the illustrative neurocognitive training system 800, the center of pressure of the user, which is determined by the data processing device 814 from the force and moment output data of the force measurement assembly 822 described above, is used to control the displacement of a cursor on the output screen 812 of the visual display device 810. In the fifth training mode, the user must move the cursor into a circular zone of a target that is randomly generated on the output screen 812. Once the cursor has remained in the circular zone of the target for a user-specified amount of time, the target disappears, and is randomly generated in another location on the output screen 812 by the data processing device 814.

Figure 35:
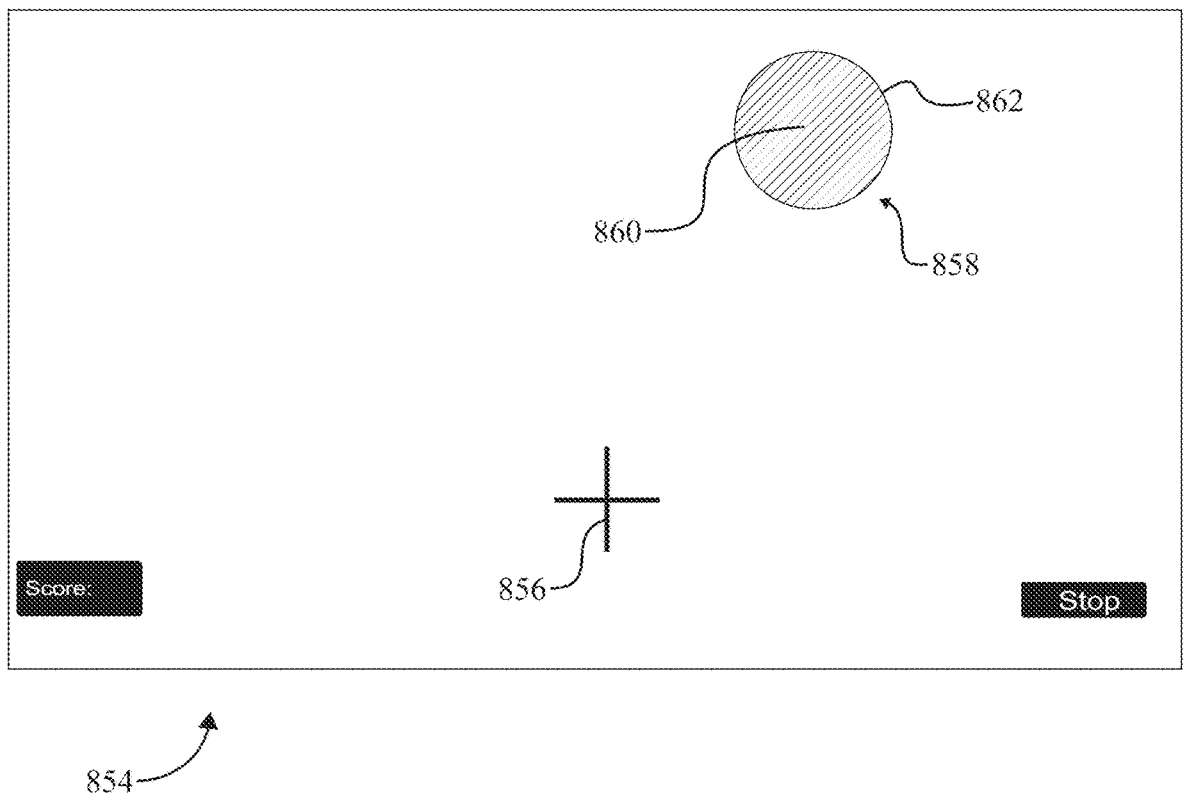
FIG. 35 is a screen image of a fifth training mode displayed on the output screen of the visual display device of the neurocognitive training system, according to the illustrative embodiment of the invention.

In particular, with reference to the screen image 854 depicted in FIG. 35, in the illustrative fifth training mode, the data processing device 814 is programmed to generate and display a visual target 858 defining a boundary 862 on the output screen 812 of the visual display device 810. The data processing device is further programmed to generate and display a displaceable cursor 856 on the output screen 812. In the illustrative embodiment, the user input device for the fifth training mode comprises the force measurement assembly 822 described above. In the fifth training mode, the center of pressure (COP) determined from the force and moment output data of the force measurement assembly 822 in the manner described above (e.g., see equations (16) and (17) above), is used to control the movement of the displaceable cursor 856 on the output screen 812 of the visual display device 810. For example, after being presented with the visual target 858 on the screen 812, the correct action to be taken by the user is to displace the cursor 856 into the interior region 860 defined by the circular boundary 862 of the visual target 858. Based upon the user's movement on the force measurement assembly 822 (i.e., shifting his weight to the right, to the left, up, or down), the cursor 856 is displaced accordingly on the screen 812 based upon the computed COP of the user. During the fifth training mode, the data processing device 814 is programmed to determine whether the user performs the correct action by displacing the cursor 856 into the interior region 860 defined by the boundary 862 of the visual target 858. The data processing device 814 is further programmed to determine whether the displaceable cursor 856 has remained within the interior region 860 of the visual target 858 for a predetermined period of time. And, when the data processing device 814 has determined that the displaceable cursor 856 has remained within the interior region 860 of the visual target 858 for the predetermined period of time, the data processing device is additionally programmed to generate and display the visual target 858 in another random location on the output screen 812 of the visual display device 810. In the illustrative embodiment, the fifth training mode continues in this manner for a predetermined duration of time while the user is presented with visual targets 858 in different locations on the output screen 812. For each of the visual targets 858 displayed in the fifth training mode, the user is required to displace the cursor 856 into the interior region 860 of the visual target 858 by controlling the movement of the cursor 856 by shifting his or her weight on the force measurement assembly 822 on which he or she is standing during the fifth training mode.

In the sixth training mode performed using the illustrative neurocognitive training system 800, the center of pressure of the user is determined by the data processing device 814 from the force and moment output data of the force measurement assembly 822 described above, while the user performs a series of trials with varying conditions. In addition to training, the sixth mode of the system 800 also may be used for the testing of the user.

In the illustrative embodiment, the sixth training mode performed using the neurocognitive training system 800 comprises eight (8) conditions under which a user is trained or tested (i.e., eight training or testing stages). In accordance with the first training and/or testing condition, a user simply stands in a stationary, upright position on the force measurement assembly 822 in a normal stance with his or her eyes open. In particular, the user stands still with his or her feet approximately placed on the force measurement assembly 822 according to instructions on the output screen 812 of the visual display device 810. While standing still on the force measurement assembly 822 during the trial(s) of the first condition, the hands of the user are placed on his or her hips, and the user looks straight ahead with his or her eyes open. If a clinician is present during the testing and/or training, the clinician may instruct the user as to the proper form during the first training condition. Then, the user begins the initial trial of the first training and/or testing condition. In addition, if a clinician is present during the training and/or testing, the clinician may use a user input device 824, such as a wireless remote control with a plurality of buttons, to record any errors performed by the user. For example, quantifiable errors that may be recorded by the clinician include: (i) the user lifting his or her hands off his or her hips, (ii) the user opening his or her eyes during a closed eyes trial, (iii) the user stepping off the force measurement assembly 822 or moving from the starting position, and (iv) an inability of the user to maintain action with the beat of the metronome for two or more consecutive beats. During the first condition, the data processing device 814 may be programmed to generate and display a solid color background image on the output screen 812 of the visual display device 810.

In accordance with the second training and/or testing condition of the sixth mode, a user stands in a stationary, upright position on the force measurement assembly 822 in a normal stance with his or her eyes closed. In particular, the user stands still with his or her feet approximately placed on the force measurement assembly 822 according to instructions on the output screen 812 of the visual display device 810. While standing still on the force measurement assembly 822 during the trial(s) of the second condition, the hands of the user are placed on his or her hips, and the eyes of the user are closed. If a clinician is present during the testing and/or training, the clinician may instruct the user as to the proper form during the second training condition. Then, the user begins the initial trial of the second training and/or testing condition. As described above, if a clinician is present during the training and/or testing, the clinician may use a user input device 824, such as a wireless remote control with a plurality of buttons, to record any errors performed by the user. Similar to the first condition, during the second condition, the data processing device 814 may be programmed to generate and display a solid color background image on the output screen 812 of the visual display device 810.

In accordance with the third training and/or testing condition, a block of foam is placed on the top surface of the force measurement assembly 822 before a user stands on the force measurement assembly 822. Then, the user stands in a stationary, upright position on the top surface of the foam, which is disposed on the force measurement assembly 822, in a normal stance with his or her eyes open. In particular, similar to the first condition described above, during the third condition, the user stands still with his or her feet approximately placed on the force measurement assembly 822 according to instructions on the output screen 812 of the visual display device 810. While standing still on the foam during the trial(s) of the third condition, the hands of the user are placed on his or her hips, and the user looks straight ahead with his or her eyes open. If a clinician is present during the testing and/or training, the clinician may instruct the user as to the proper form during the third training condition. Then, the user begins the initial trial of the third training and/or testing condition. As described above, if a clinician is present during the training and/or testing, the clinician may use a user input device 824, such as a wireless remote control with a plurality of buttons, to record any errors performed by the user. Similar to the first and second conditions, during the third condition, the data processing device 814 may be programmed to generate and display a solid color background image on the output screen 812 of the visual display device 810.

In accordance with the fourth training and/or testing condition, the user stands in a stationary, upright position on the top surface of the foam, which is disposed on the force measurement assembly 822, in a normal stance with his or her eyes closed. In particular, similar to the third condition described above, during the fourth condition, the user stands still with his or her feet approximately placed on the force measurement assembly 822 according to instructions on the output screen 812 of the visual display device 810. While standing still on the foam during the trial(s) of the fourth condition, the hands of the user are placed on his or her hips, and the eyes of the user are closed. If a clinician is present during the testing and/or training, the clinician may instruct the user as to the proper form during the fourth training condition. Then, the user begins the initial trial of the fourth training and/or testing condition. As described above, if a clinician is present during the training and/or testing, the clinician may use a user input device 824, such as a wireless remote control with a plurality of buttons, to record any errors performed by the user. Similar to the first three conditions described above, during the fourth condition, the data processing device 814 may be programmed to generate and display a solid color background image on the output screen 812 of the visual display device 810.

In accordance with the fifth training and/or testing condition of the sixth mode, a user stands in a stationary, upright position on the force measurement assembly 822 with his or her feet close together and his or her eyes closed while the user rotates his or her head back-and-forth. In particular, the user stands still with his or her feet approximately placed on the force measurement assembly 822 according to instructions on the output screen 812 of the visual display device 810. While standing still on the force measurement assembly 822 during the trial(s) of the fifth condition, the hands of the user are placed on his or her hips, and the eyes of the user are closed while the user rotates his or her head back-and-forth in an oscillatory manner. For example, the user may rotate his or her head plus or minus 30 degrees from a neutral center position in sync with an audible metronome (e.g., at 120 beats per minute). If a clinician is present during the testing and/or training, the clinician may instruct the user as to the proper form during the fifth training condition. Then, the user begins the initial trial of the fifth training and/or testing condition. As described above, if a clinician is present during the training and/or testing, the clinician may use a user input device 824, such as a wireless remote control with a plurality of buttons, to record any errors performed by the user.

Figure 36:
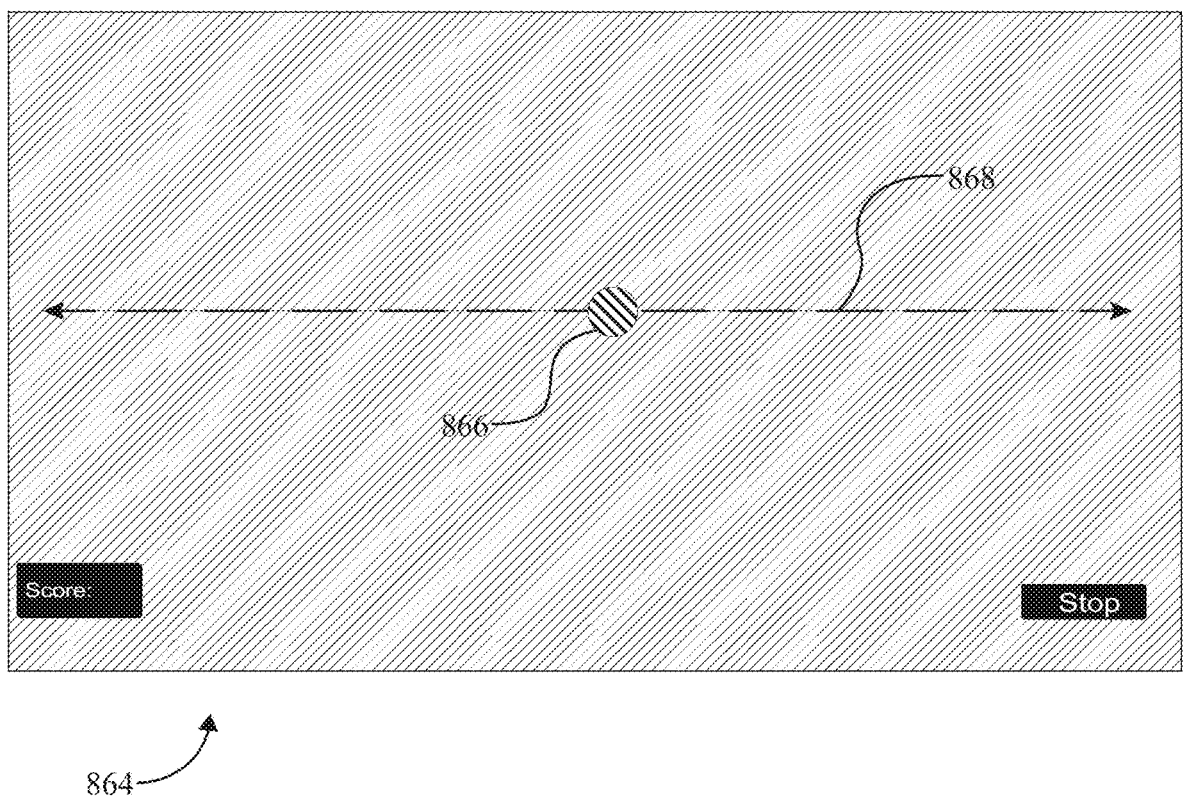
FIG. 36 is a screen image of a sixth training mode displayed on the output screen of the visual display device of the neurocognitive training system, according to the illustrative embodiment of the invention.

In accordance with the sixth training and/or testing condition of the sixth mode, a user stands in an upright position on the force measurement assembly 822 with his or her eyes open while the user rotates his or her body back-and-forth. In particular, the user stands at the approximate center of the force measurement assembly 822 with his or her feet close together, and both of his or her arms extended out in front with his or her hands clasped together and his or her thumbs straight up. While focusing on his or her thumbs, the user rotates his or her entire body back-and-forth in an oscillatory manner. For example, while focusing on his or her thumbs, the user rotates his or her entire body plus or minus 30 degrees from a neutral center position (i.e., over an overall angular range of 60 degrees) in sync with a metronome set to a predetermined number of beats per minute (e.g., 40 beats per minute) and/or a visual object displaced across the output screen 812 of the visual display device 810. If a clinician is present during the testing and/or training, the clinician may instruct the user as to the proper form during the sixth training condition. Then, the user begins the initial trial of the sixth training and/or testing condition. As described above, if a clinician is present during the training and/or testing, the clinician may use a user input device 824, such as a wireless remote control with a plurality of buttons, to record any errors performed by the user. As shown in FIG. 36, during the sixth condition, the data processing device 814 may be programmed to generate and display a screen image 864 on the output screen 812 of the visual display device 810 that includes a ball 866 being displaced across the output screen 812 along the path 868, which operates as a visual metronome. That is, in the illustrative embodiment, the user tries to rotate his or her entire body in sync with the ball 866 displaced across the output screen 812 so that he or she maintains the proper body rotation timing. In an alternative embodiment, rather than displaying the screen image 864 of FIG. 36 on the output screen 812 during the performance of the sixth condition, the data processing device 814 may be programmed to generate and display a stationary screen image on the output screen 812 of the visual display device 810. In this alternative embodiment, the stationary screen image may include a plurality of vertical indicator lines that assist the user in achieving the proper rotational displacement path (e.g., the stationary screen image may contain a center vertical indicator line that represents the neutral center position, a first vertical indicator line disposed on a left side of the center vertical indicator line that represents the −30 degree rotational displacement limit, and a second vertical indicator line disposed on a right side of the center vertical indicator line that represents the 30 degree rotational displacement limit).

In accordance with the seventh training and/or testing condition, similar to the third and fourth conditions described above, a block of foam is placed on the top surface of the force measurement assembly 822 before a user stands on the force measurement assembly 822. Then, the user stands in a stationary, upright position on the top surface of the foam, which is disposed on the force measurement assembly 822, in a normal stance with his or her eyes closed while the user rotates his or her head back-and-forth. In particular, while standing still on the foam during the trial(s) of the seventh condition, the hands of the user are placed on his or her hips, and the eyes of the user are closed while the user rotates his or her head back-and-forth in an oscillatory manner. For example, the user may rotate his or her head plus or minus 30 degrees from a neutral center position in sync with an audible metronome (e.g., at 120 beats per minute). If a clinician is present during the testing and/or training, the clinician may instruct the user as to the proper form during the seventh training condition. Then, the user begins the initial trial of the seventh training and/or testing condition. As described above, if a clinician is present during the training and/or testing, the clinician may use a user input device 824, such as a wireless remote control with a plurality of buttons, to record any errors performed by the user.

In accordance with the eighth training and/or testing condition, similar to the seventh condition described above, a block of foam is placed on the top surface of the force measurement assembly 822 before a user stands on the force measurement assembly 822. Then, the user stands in an upright position on the foam with his or her eyes open in a narrow stance while the user rotates his or her body back-and-forth. In particular, the user stands in a narrow stance with both of his or her arms extended out in front, his or her hands clasped together, and his or her thumbs straight up. While focusing on his or her thumbs, the user rotates his or her entire body back-and-forth in an oscillatory manner. For example, while focusing on his or her thumbs, the user rotates his or her entire body plus or minus 30 degrees from a neutral center position (i.e., over an overall angular range of 60 degrees) in sync with an audible metronome set to a predetermined number of beats per minute (e.g., 40 beats per minute) and/or a visual object displaced across the output screen 812 of the visual display device 810. If a clinician is present during the testing and/or training, the clinician may instruct the user as to the proper form during the eighth training condition. Then, the user begins the initial trial of the eighth training and/or testing condition. As described above, if a clinician is present during the training and/or testing, the clinician may use a user input device 824, such as a wireless remote control with a plurality of buttons, to record any errors performed by the user. Similar to the sixth condition described above, during the eighth condition, the data processing device 814 may be programmed to generate and display the screen image 864 on the output screen 812 of the visual display device 810 that includes the ball 866 being displaced across the output screen 812 along the path 868 (refer to FIG. 36), which operates as a visual metronome. That is, in the illustrative embodiment, the user tries to rotate his or her entire body in sync with the ball 866 displaced across the output screen 812 so that he or she maintains the proper body rotation timing. In an alternative embodiment, as described above for the sixth condition, rather than displaying the screen image 864 of FIG. 36 on the output screen 812 during the performance of the eighth condition, the data processing device 814 may be programmed to generate and display the stationary screen image explained above.

In the seventh training mode carried out by the illustrative neurocognitive training system 800, similar to the fifth training mode described above, the center of pressure of the user, which is determined by the data processing device 814 from the force and moment output data of the force measurement assembly 822, is used to control the displacement of a cursor on the output screen 812 of the visual display device 810. In the seventh training mode, the user must move the cursor into circular zones of a plurality of different targets that are randomly generated on the output screen 812. Once the cursor has remained in a circular zone of one of the targets for a predetermined amount of time, the user is prompted to displace the cursor to one or more additional targets in other locations on the output screen 812 by the data processing device 814.

Figure 38:
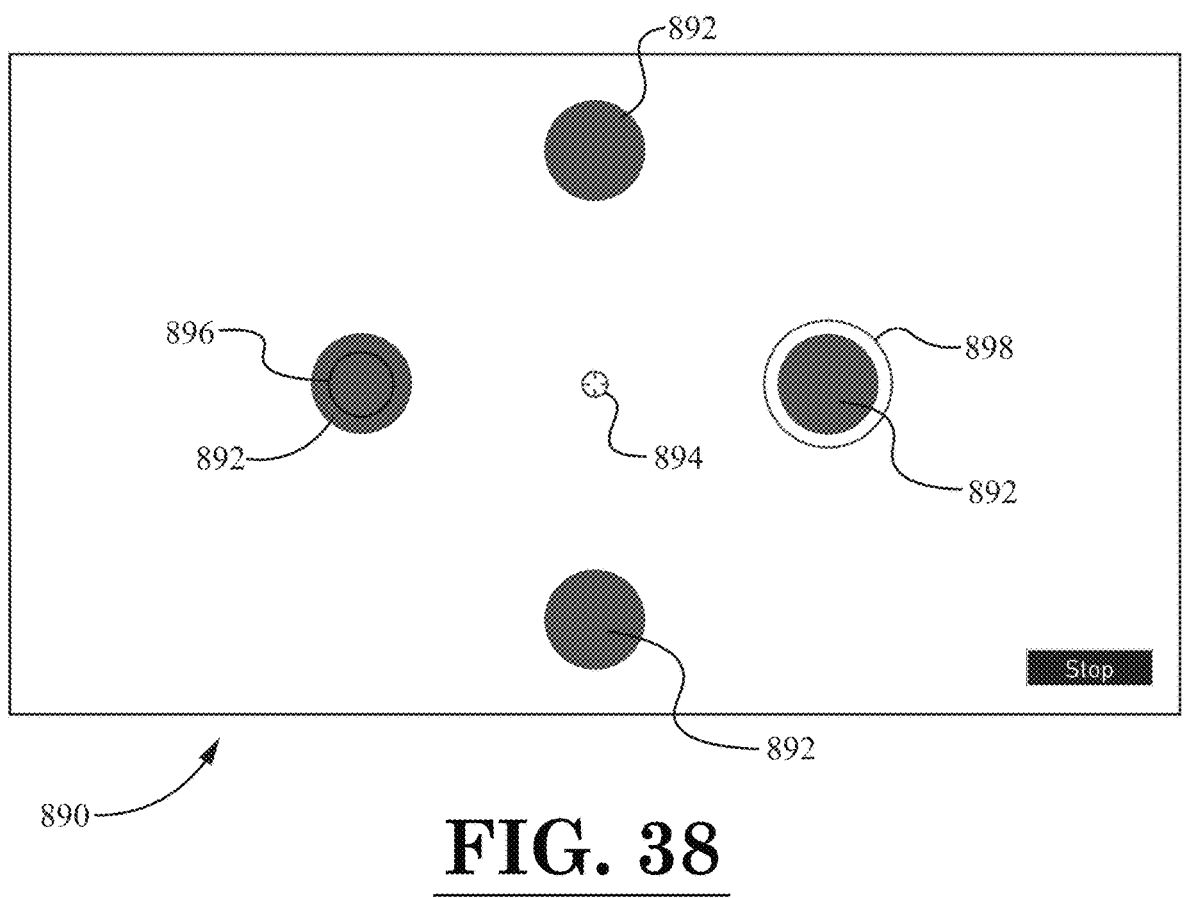
FIG. 38 is a screen image of a seventh training mode displayed on the output screen of the visual display device of the neurocognitive training system, according to the illustrative embodiment of the invention.

In particular, with reference to the screen image 890 depicted in FIG. 38, in the illustrative seventh training mode, the data processing device 814 is programmed to generate and display a plurality of visual targets 892 defining respective boundaries on the output screen 812 of the visual display device 810. The data processing device 814 is further programmed to generate and display a displaceable cursor 894 on the output screen 812. In the illustrative embodiment, the user input device for the seventh training mode comprises the force measurement assembly 822 described above. In the seventh training mode, the center of pressure (COP) determined from the force and moment output data of the force measurement assembly 822 in the manner described above (e.g., see equations (16) and (17) above), is used to control the movement of the displaceable cursor 894 on the output screen 812 of the visual display device 810. For example, in the seventh training mode, the user is initially required to hover the displaceable cursor 894 controlled by his or her center of pressure (COP) trace over the target sensitivity area of the initial target 892 (i.e., the shaded area defined by the target 892 on the left side of the screen image 890 in FIG. 38). When the displaceable cursor 894 is within the sensitivity area of the target 892, a clock generated by the data processing device 814 begins to count down toward zero. Once the clock reaches zero, the second target 892 (i.e., the target 892 on the right side of the screen image 890 in FIG. 38) will spawn by the data processing device 814 generating a pulsating concentric ring 898 around the outer zone of the target 892, and a second clock generated by the data processing device 814 begins counting down. This is the "reaction time" clock, which counts how long it takes for the user to move the displaceable cursor 894 out of the initial target sensitivity area and when the user has made it to the final target, reported as the "Time to Target." In the illustrative embodiment, the seventh training mode continues in this manner for a predetermined duration of time while the user is presented with visual targets 892 in different locations on the output screen 812. In the seventh training mode, a pulsating concentric ring 896 within the target sensitivity area of the target 892 may be used to designate that the target 892 is active (i.e., the ring 896 moves in and out concentrically to indicate that the target 892 on the left side of the screen image 890 in FIG. 38 is active). For each of the visual targets 892 displayed in the seventh training mode, the user is required to displace the cursor 894 into the target sensitivity area of the visual target 892 by controlling the movement of the cursor 894 by shifting his or her weight on the force measurement assembly 822 on which he or she is standing during the seventh training mode.

Advantageously, in the seventh training mode, the data processing device 814 may be programmed to record the user's body reaction time and eye-body coordination to give a unique measurement of reaction time. Also, in the illustrative embodiment, the user is instructed to "hover" his or her body weight over the second target, requiring an additional measure of body control and stability.

In one or more embodiments of the seventh training mode, the data processing device 814 measures not only the traditional eye/hand reaction time, but also how quickly the body can accurately shift balance based on a visual stimulus. The data processing device 814 measures in various directions, such as up, down, right and left, but also at different separation or distances between targets. The data processing device 814 breaks down the process into two parts, the initial time it takes the subject to see target 892, process the information and start the cursor to move; and the subsequent time it actually takes the cursor to move to the second target 892 and select it. The first part is the visual component and the second part is the motor component. Both of these skills can be affected post-concussion and post traumatic brain injury.

Also, in one or more embodiments of the seventh training mode, the data processing device 814 is programmed with several variables that may be selected by the user beyond the background, touch sensitivity, and target type. One variable is grid size, the larger the grid size chosen, the great the distance between the targets 892. The other variable is target size, which also relates to sensitivity. Also, in the seventh training mode, the data processing device 814 selects random pacing by default, which means that the time from a user moving the displaceable cursor 894 on the initial target 892, to when the user is prompted to move it to the next target 892, varies randomly. This is done so that the user cannot predict when to start moving his or her hand. An auditory clue may also be given by a user selecting the appropriate box on the output screen 812 of the visual display device 810.

In the eighth training mode carried out by the illustrative neurocognitive training system 800, a target appears randomly on the output screen 812 of the visual display device 810 with a "tunnel" video background. The user must then touch the target. Once the user touches the target, it will disappear, and another target will appear on the output screen 812. If the user does not touch the target after a predetermined period of time has elapsed, the target will disappear and then the target will reappear after a specified time period. This process continues for the duration of the training mode.

Figure 39:
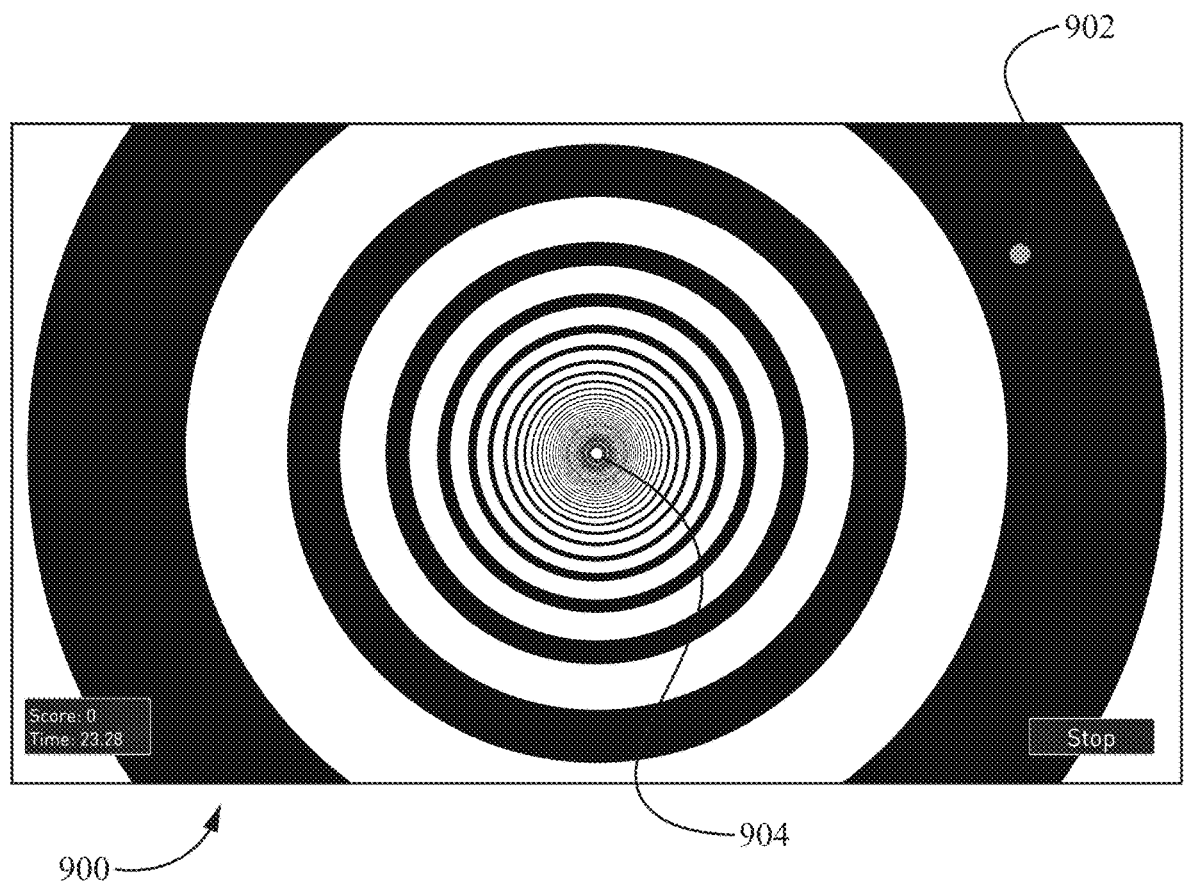
FIG. 39 is a screen image of an eighth training mode displayed on the output screen of the visual display device of the neurocognitive training system, according to the illustrative embodiment of the invention.

In particular, with reference to the screen image 900 depicted in FIG. 39, in the eighth illustrative training mode, the data processing device 814 is programmed to generate and display a plurality of visual objects on the output screen 812 of the visual display device 810 in a plurality of different sequential locations on the output screen 812. For example, as shown in FIG. 39, a first target 902 that is generated by the data processing device 814 may appear on "tunnel" video background displayed on the output screen 812. Advantageously, the "tunnel" video background is generated by the data processing device 814 so as to make the user feel as if he or she is immersed in the scene, moving either forward or backward depending on the movement of the concentric lines in FIG. 39. In the eighth illustrative training mode, the data processing device 814 may be programmed to control the point of origin 904 of the "tunnel" video background based on the center of pressure (COP) of the user determined from the force measurement assembly 822, such that as the user moves, the center of the "tunnel" video background also moves. In the exemplary screen image 900 depicted in FIG. 39, the point of reference of the target 902 may either be fixed to the screen or fixed to the "tunnel" video background, which comprise concentric white and black circles in the exemplary case. When the concentric rings in the screen image 900 of FIG. 39 are moving from the outer periphery to the center, then the user perceives the effect of moving away from the output screen 812 (i.e., moving backwards). Conversely, when the concentric rings in the screen image 900 of FIG. 39 are moving from the center to the outer periphery, then the user perceives the effect of moving into the output screen 812 (i.e., moving forwards). Once the user touches the target 902 on the touchscreen user interface of the visual display device 810, the data processing device 814 receives an input signal from the touchscreen user interface based upon an input response by the user. Then, the data processing device 814 is programmed to determine whether the user has performed the correct action by selecting the target 902. After the user touches the first target 902 using the touchscreen user interface of the visual display device 810, the target 902 disappears, and a second target appears on the output screen 812.

In a further embodiment of the neurocognitive training system 800, the data processing device 814 may be programmed to generate a visual target and 'hit zone' that are individually scalable. That is, the data processing device 814 is programmed so as to enable the radius about the visual target that registers a 'hit' by a user to be made smaller or larger than the actual image used for the visual target. In particular, in this further embodiment, the data processing device 814 is programmed to form each target from two separate images. The first image is the visual cue that the user selects. In this further embodiment, the first image may be a basic circle, a football, a smiley face, a flower, or any other suitable visual object. The second image generated by the data processing device 814 forms 'sensitivity zone', which is the area about the visual cue that the user can touch and it will register as a hit. The sensitivity zone can either be hidden or shown to the user when a test is running. Both of these images can be scaled independently of one another to adjust the behavior of the test. However, in this further embodiment, the sensitivity zone is never smaller than the visual cue, meaning that if a user ever touches the cue directly, it will register as a hit. In this further embodiment, the sensitivity zone generated by the data processing device 814 has four levels of scaling (i.e., 100%, 125%, 150%, 200%). These are factors of the size of the visual cue, so if the visual cue has a diameter of X, the smallest possible sensitivity zone is X, and the largest possible sensitivity zone is 2*X. Increasing the size of the sensitivity zone allows the user to be less accurate when touching a target, and still have it register as a hit. This is useful when focusing on the speed of a patient hitting the target and not necessarily the accuracy, or when using a visual cue that is small or difficult for the user to see.

In yet a further embodiment of the neurocognitive training system 800, the data processing device 814 may be programmed to keep track of a number of different statistics regarding the user being trained and/or tested. For example, in this further embodiment, the data processing device 814 may be programmed to record each of the following parameters regarding the performance of the user: (i) the time to hit (i.e., how long the user takes to hit a target once it appears), (ii) accuracy (i.e., how close the user's touch is to the actual center of a presented target), and (iii) accuracy by zone (i.e., how accurate the user is in the various portions of the output screen 812 of the visual display device 810). In this further embodiment, the data processing device 814 is programmed so as to enable a user to view and compare all of these performance parameters across different tests and sessions. Also, in this further embodiment, there are two discrete events that are recorded by the data processing device 814 every time a target appears on the screen and the user touches it. These discrete events are: (i) time to hit and (ii) target accuracy. Supplementary data is stored with these discrete events to allow for a number of data comparisons and extrapolations. In this further embodiment, the 'time to hit' is the amount of time that passes from a target appearing and the user successfully pressing the target. In this embodiment, mis-hits (hitting the wrong target), are discarded and not stored. Likewise, in this embodiment, the very first target appearance in a test is not stored either. This is to account for start-up time, the patient getting acclimated to the test, and a 'fuzzy' reference as to when to actually begin timing. As such, timings are stored from the appearance of the second target until the end of the test. In addition to the timing, in this embodiment, a number of additional parameters are stored, such as the test type, the target position on the screen, target and sensitivity scaling, visual cue used, background type used, together with any test-specific options or parameters. In this further embodiment, the 'target accuracy' is linked closely to the target detection explained above. When a user successfully hits a target, that touch on the screen is at a given x/y coordinate (vector), this is compared to the centered position of the target and gives us a magnitude between the actual position of the target, and the location pressed by the user. The lower the magnitude, the closer to the 'true center' of the target that the user touched. As with the 'time to hit' explained above, all supplementary data is stored with this magnitude. Using the above events with their supplementary data, the data processing device 814 may be further programmed to generate useful data graphs and comparisons for the user. For example, in one or more embodiments, the data processing device 814 may be configured to generate data graphs, such as 'Accuracy by Target Scaling', 'Time to Hit Target on the Left Side of Screen versus Right Side of Screen', 'Overall Accuracy with a Specific Visual Cue', 'Accuracy with and without Audio Cues', etc.

In still a further embodiment of the neurocognitive training system 800, the data processing device 814 may be programmed to ensure that none of the visual targets appear off the output screen 812 of the visual display device 810. That is, the data processing device 814 establishes a 'safe zone' regardless of the screen size, resolution, or target size so that a visual target is not permitted to appear off the screen 812.

In yet a further embodiment of the neurocognitive training system 800, the data processing device 814 may be programmed so as to permit the user to create custom backgrounds and visual targets. In particular, the data processing device 814 is programmed so as to allow the user to add his or her own customized backgrounds and targets to an installation folder, then the data processing device 814 is programmed to add the customized backgrounds and targets to a list of available choices for the background and targets. For example, the user may upload one or more images containing customized background (e.g., a custom video background) for use during the different training modes described above. In the illustrative embodiment, the images containing the customized backgrounds may be in .png or .jpg format, and be capable of fitting a resolution of approximately 1920×1080 pixels. For example, a user may have the ability to upload a video of his or her own choosing to serve as the screen background. If the image containing the customized background has a different native resolution, it is scaled accordingly. In addition to the customized backgrounds, the data processing device 814 also is programmed so as to allow the user to select from a plurality of standard backgrounds, such as solid color backgrounds, outdoor backgrounds depicting sports fields, such as baseball fields, football fields, and soccer fields, and indoor backgrounds depicting the interior of sports arenas, such as basketball arenas and ice hockey rinks. In the illustrative embodiment, similar to the customized backgrounds, the images containing the customized targets may be in .png or .jpg format, and be capable of fitting a resolution of approximately 1920× 1080 pixels. If the image containing the customized target has a different native resolution, it is scaled accordingly. In addition to the customized targets, the data processing device 814 also is programmed so as to allow the user to select from a plurality of standard targets, such as targets having a simple geometric shape (e.g., circular targets and square targets) and targets in the shape of objects used in various sports (e.g., footballs, soccer balls, and hockey pucks).

In yet a further embodiment of the neurocognitive training system 800, the data processing device 814 may be programmed so as to allow a user to change the contrast display setting for the screen background. In this further embodiment, the data processing device 814 is programmed to: (i) generate and display at least one visual target and a screen background on the output screen of the visual display device, the at least one visual target being superimposed on the screen background; (ii) receive an input signal from the user input device based upon an input response by the user; and (iii) determine, based upon the input signal received from the user input device, a contrast display setting for the screen background relative to the at least one visual target, the contrast display setting enabling the user to gradually adapt to increasing levels of visual stimulation. In this further embodiment, the data processing device 814 is further programmed to generate a sliding scale and/or contrast value input box on the output screen of the visual display device for allowing the user to input a value for the contrast display setting for the screen background.

In this further embodiment, a system user (e.g., a therapist) adjusts the contrast display setting to "dim" or "tint" the screen background. Advantageously, the adjustment of the contrast display setting helps visually sensitive patients slowly adapt to increasing levels of visual stimulation. The contrast display setting adjustment may be provided in conjunction with all training modes of the neurocognitive training system 800 described herein. By default, the contrast display setting will be set to 100% by the data processing device 814, but can be scaled up to 0% and every integer in between, by typing a digit into a box on the training mode options panel or by moving a slider bar to adjust the contrast. The adjustment of the contrast display setting is particularly useful on video backgrounds, such as Optokinetics, to decrease the visual motion sensitivity and gradually increase it over time. The target appears in front of the screen background contrast overlay, meaning that the target is not be affected by the contrast display setting (i.e., the screen background is "dimmed" or "tinted" by the contrast display setting, but the display of the target is not affected by the contrast display setting). In this further embodiment, there may be an additional field in the settings bar at the bottom of the main screen that shows the "contrast overlay %" and the reported value (100-0). Also, the contrast display setting may be reported in the training report and to the database. In addition, the % contrast value (100-opacity) may be displayed to the user, and the user may be able to type in a desired value for the % contrast value.

In yet a further embodiment of the neurocognitive training system 800, the data processing device 814 is further programmed to generate one or more input screen elements for allowing the user to upload a custom video background that is able to be used as the screen background displayed on the output screen of the visual display device (e.g., the user can create a custom video background on his or her mobile phone and then upload the background to the data processing device); and determine, based upon the input signal received from the user input device, the contrast display setting for the custom video background relative to the at least one visual target (i.e., the user is able to change the contrast display setting for a custom video background that he or she has uploaded).

Figure 37:
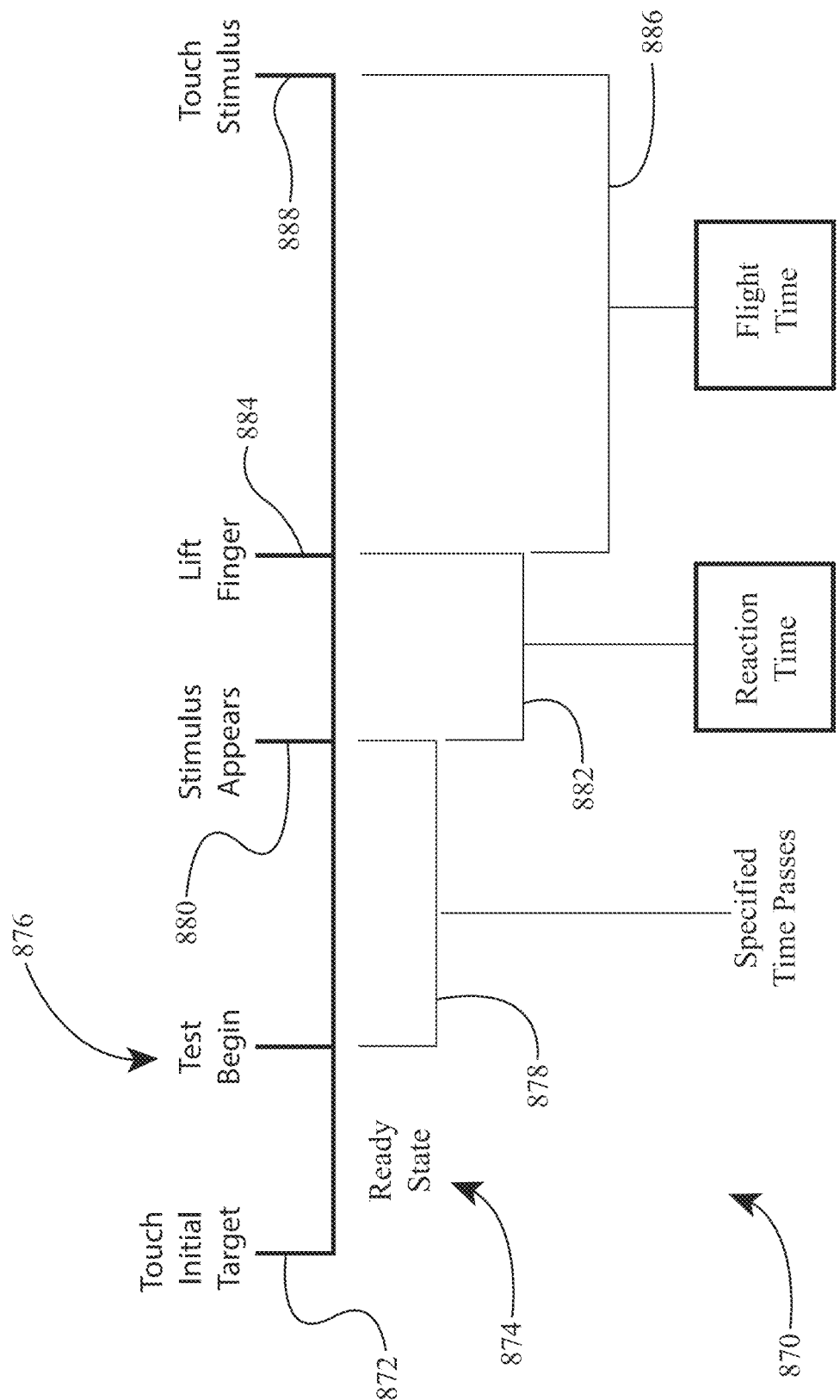
FIG. 37 is a diagrammatic timeline graphically depicting the time periods involved in computing the total reaction score for the user, according to a further illustrative embodiment of the invention.

In still a further embodiment of the neurocognitive training system 800, the data processing device 814 may be programmed to calculate the reaction time of the user based upon a plurality of different input data parameters. In this further embodiment, the data processing device 814 is programmed to generate three stages for the reaction time of the user: (i) reaction to stimulus, (ii) time to stimulus, and (iii) accuracy. Also, in this further embodiment, the data processing device 814 is programmed to track three input modes of the user (i.e., touch down, lift, and travel time) individually so as to generate the composite score for the user. In addition, in this further embodiment, the reaction time is a training that can measure how fast a user can react to a visual and/or audial stimulus. In general, during one or more training modes described above, with reference to the timeline 870 depicted in FIG. 37, the user places his or her finger on a target at point 872, some time passes, and then a second target appears at point 880 and the user has to move his or her finger from the first target to the second target as quickly as possible. In this embodiment, the training flow involves the following elements: (i) ready state, (ii) stimulus, (iii) reaction time, and (iv) flight time. During the 'ready state' condition 874 in FIG. 37, the user places and holds their finger on a designated target. This is analogous to 'On your marks, get set' to a sprinter. The 'ready state' condition 874 tells the software loaded on the data processing device 814 that the user is ready and the test actually begins at 876 in FIG. 37 once the user has had their finger in place for 500 milliseconds (ms) (this duration is adjustable, but this is the default). In this embodiment, the stimulus appears at 880 in FIG. 37 according to a few parameters. Once the 'ready state' time period 874 is concluded, the stimulus appears after an arbitrary amount of time 878 has passed (see FIG. 37). This time may be constant and set beforehand, or a random amount of time between 500 milliseconds (ms) and 5 seconds (s) may be used, all of which are user selectable. In this embodiment, the 'reaction time' 882 is the amount of time that passes from the stimulus appearing at 880, and the user lifting their finger at 884 from the ready state to move to the next stimulus target (refer to FIG. 37). In this embodiment, the 'flight time' 886 is the amount of time that passes from the user lifting his or her finger at 884 in reaction to the next stimulus appearing, and the user actually pressing the stimulus at 888 in FIG. 37. In this embodiment, the data processing device 814 determines the total reaction score as a function of both the reaction time and flight time. As one example, the data processing device 814 may compute the total reaction score for the user based upon the following formula: 10–(Reaction Time+Flight Time). This formula gives a theoretical maximum (though impossible) score of 10, and the worst possible score of 0 (meaning it took more than 10 seconds for the user to react and travel to the target). As with all targets accuracy other supplementary data is tracked and stored.

In yet a further embodiment of the neurocognitive training system 800, the data processing device 814 may be programmed to rank and score the training of the user based upon the output of the force measurement assembly 822 (i.e., based upon the user's center of pressure determined from the force measurement assembly 822 being in sync with a displaceable visual target on the output screen 812). For example, in this further embodiment, the user's center of pressure determined from the force measurement assembly 822 is compared to the displacement of a ball across the output screen 812 (e.g., the data processing device 814 determines if the user displaces his or her center of pressure in sync with the ball 866 displaced back-and-forth on the screen image 864 of FIG. 36). In this further embodiment, the timing of the change of direction of the user also may be compared to the change in the direction of the stimulus (i.e., how long does it take for the user to react to the change in the displacement direction of the ball 866 on the output screen 812).

In still a further embodiment of the neurocognitive training system 800, rather than determining the center of pressure of the user from the force measurement assembly 822, the displacement of the center of gravity (COG) for the user may be estimated from one or more inertial measurement units attached to the head of the user. More specifically, in this further embodiment, the displacement of the center of gravity (COG) for the user may be estimated by the data processing device 814 using the position of the head determined from the one or more inertial measurement units attached to the head of the user (i.e., computed using the equation (23) below). For example, the height of the user may be entered into the data processing device 814, and then using the entered height of the user, the center of gravity (COG) of the user may be estimated to be a predetermined distance (e.g., a specified number of inches) from the one or more inertial measurement units attached to the head of the user. Also, if the user is presumed to bend only at his or her ankles, the user may be modeled as an inverted pendulum by the data processing device 814, thus permitting the postural sway displacement and/or the postural sway angle for the user to be determined by the data processing device 814 based upon the positional output data from the one or more inertial measurement units attached to the head of the user. For example, the average of the sway displacement of the user may be presumed to be the upright zero sway position of user, and then the deviations from the zero sway position of the user determined by the positional output data from the one or more head-mounted inertial measurement units may be used to determine the postural sway displacement and/or the postural sway angle.

In this further embodiment, the one or more inertial measurement units may comprise a triaxial (three-axis) accelerometer sensing linear acceleration a', a triaxial (three-axis) rate gyroscope sensing angular velocity $\vec{\omega}'$, a triaxial (three-axis) magnetometer sensing the magnetic north vector $\vec{n}'$, and a central control unit or microprocessor operatively coupled to each of accelerometer, gyroscope, and the magnetometer. In addition, the one or more inertial measurement units each may comprise a wireless data interface for electrically coupling the inertial measurement unit to the data processing device 814.

Next, an illustrative manner in which the data processing device 814 of the neurocognitive training system 800 performs the inertial measurement unit (IMU) calculations will be explained in detail. In particular, this calculation procedure will describe the manner in which the orientation and position of the head of the user could be determined using the signals from the one or more inertial measurement units (IMUs) of the system 800. As explained above, in this further embodiment, each of the one or more inertial measurement units may include the following three triaxial sensor devices: (i) a three-axis accelerometer sensing linear acceleration $\vec{a}'$, (ii) a three-axis rate gyroscope sensing angular velocity $\vec{\omega}'$, and (iii) a three-axis magnetometer sensing the magnetic north vector Each inertial measurement unit senses in the local (primed) frame of reference attached to the IMU itself. Because each of the sensor devices in each IMU is triaxial, the vectors $\vec{a}'$, $\vec{\omega}'$, $\vec{n}'$ are each 3-component vectors. A prime symbol is used in conjunction with each of these vectors to symbolize that the measurements are taken in accordance with the local reference frame. The unprimed vectors that will be described hereinafter are in the global reference frame.

The objective of these calculations is to find the orientation $\vec{\theta}(t)$ and position $\vec{R}(t)$ in the global, unprimed, inertial frame of reference. Initially, the calculation procedure begins with a known initial orientation $\vec{\theta}_0$ and position $\vec{R}_0$ in the global frame of reference.

For the purposes of the calculation procedure, a right-handed coordinate system is assumed for both global and local frames of reference. The global frame of reference is attached to the Earth. The acceleration due to gravity is assumed to be a constant vector $\vec{g}$. Also, for the purposes of the calculations presented herein, it is presumed the sensor devices of the one or more inertial measurement units (IMUs) provide calibrated data. In addition, all of the signals from the IMUs are treated as continuous functions of time. Although, it is to be understood the general form of the equations described herein may be readily discretized to account for IMU sensor devices that take discrete time samples from a bandwidth-limited continuous signal.

The orientation $\vec{\theta}(t)$ is obtained by single integration of the angular velocity as follows:

$$\vec{\theta}(t) = \vec{\theta}_0 + \int_0^t \vec{\varpi}(t)dt \tag{18}$$

$$\vec{\theta}(t) = \vec{\theta}_0 + \int_0^t \Theta(t)\vec{\varpi}'(t)dt \tag{19}$$

where $\vec{\theta}(t)$ is the matrix of the rotation transformation that rotates the instantaneous local frame of reference into the global frame of reference.

The position is obtained by double integration of the linear acceleration in the global reference frame. The triaxial accelerometer of each IMU senses the acceleration $\vec{a}'$ in the local reference frame. The acceleration $\vec{a}'$ has the following contributors: (i) the acceleration due to translational motion, (ii) the acceleration of gravity, and (iii) the centrifugal, Coriolis and Euler acceleration due to rotational motion. All but the first contributor has to be removed as a part of the change of reference frames. The centrifugal and Euler accelerations are zero when the acceleration measurements are taken at the origin of the local reference frame. The first integration gives the linear velocity as follows:

$$\vec{v}(t) = \vec{v}_0 + \int_0^t \{\vec{a}(t) - \vec{g}\}dt \tag{20}$$

$$\vec{v}(t) = \vec{v}_0 + \int_0^t \{\Theta(t)[\vec{a}'(t) + 2\vec{\varpi}' \times \vec{v}'(t)] - \vec{g}\}dt \tag{21}$$

where $2\vec{\omega}' \times \vec{v}'(t)$ is the Coriolis term, and where the local linear velocity is given by the following equation:

$$\vec{v}'(t) = \vec{\theta}^{-1}(t)\vec{v}(t) \tag{22}$$

The initial velocity $\vec{v}_0$ can be taken to be zero if the motion is being measured for short periods of time in relation to the duration of Earth's rotation. The second integration gives the position as follows:

$$\vec{R}(t) = \vec{R}_0 + \int_0^t \vec{v}(t)dt \tag{23}$$

At the initial position, the IMU's local-to-global rotation's matrix has an initial value $\vec{\theta}(0) \equiv \vec{\theta}_0$. This value can be derived by knowing the local and global values of both the magnetic north vector and the acceleration of gravity. Those two vectors are usually non-parallel. This is the requirement for the $\vec{\theta}_0(\vec{g}', \vec{n}', \vec{g}, \vec{n})$ to be unique. The knowledge of either of those vectors in isolation gives a family of non-unique solutions $\vec{\theta}_0(\vec{g}', \vec{g})$ or $\theta_0(\vec{n}', \vec{n})$ that are unconstrained in one component of rotation. The $\vec{\theta}_0(\vec{g}', \vec{n}', \vec{g}, \vec{n})$ has many implementations, with the common one being the Kabsch algorithm. As such, using the calculation procedure described above, the data processing device 814 of the system 800 may determine the orientation $\vec{\theta}(t)$ and position $\vec{R}(t)$ of one or more body portions of the user. For example, the orientation of the head of the user may be determined by computing the orientation $\vec{\theta}(t)$ and position $\vec{R}(t)$ of two points on the head of the user (i.e., at the respective locations of two inertial measurement units (IMUs) disposed on the head of the user).

In one or more alternative embodiments, rather than using one or more inertial measurement units (IMUs) that include an accelerometer, a gyroscope, and a magnetometer, a single accelerometer may be used to simply measure the displacement of the head of the user (e.g., by using equation (23) described above). As explained above, the acceleration output from the accelerometer may be integrated twice in order to obtain the positional displacement of the head of the user.

It is readily apparent that the neurocognitive training system 800 described above offers numerous advantages and benefits for various treatment and performance enhancement applications involving neurocognitive training and/or testing. For example, the neurocognitive training system 800 may be used to diagnose and/or treat the effects of a concussion or traumatic brain injury (TBI) for either preventative maintenance or as part of a return to play protocol. In particular, the abovedescribed training modes of the neurocognitive training system 800 may be used to improve performance as a preventative measure and/or objectify visual-motor performance as a tool to determine return to play readiness in concussed athletes or athletes who have sustained a TBI. As another example, the neurocognitive training system 800 may be used by an athlete seeking performance enhancement of the visual-motor system. Specifically, functional improvements resulting from training on the aforedescribed neurocognitive training system 800 will translate to enhanced vision and athletic performance. As yet another example, the neurocognitive training system 800 may be used as part of a rehabilitation regime for an orthopedic and/or neurological injury. In particular, the neurocognitive training system 800 may be used to provide a unique rehabilitation modality that requires controlled movement and functional performance. In addition, in such an application, the aforedescribed neurocognitive training system 800 may be used in conjunction with other rehabilitation tools, such as a stability apparatus.

While reference is made throughout this disclosure to, for example, "one embodiment" or a "further embodiment", it is to be understood that some or all aspects of these various embodiments may be combined with one another as part of an overall embodiment of the invention. That is, any of the features or attributes of the aforedescribed embodiments may be used in combination with any of the other features and attributes of the aforedescribed embodiments as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A system for testing and/or training the vision of a user, said system comprising:
    at least one camera, the at least one camera configured to capture a plurality of images of a head of a user during a vision test or vision training routine;
    a visual display device having an output screen, the visual display device configured to display one or more visual objects on the output screen so that the one or more visual objects are visible to the user; and
    a data processing device, the data processing device operatively coupled to the at least one camera and the visual display device, the data processing device being programmed to:
        generate and display one or more configurations of a visual object on the output screen of the visual display device during the vision test or vision training routine;
        determine a head velocity or head speed of the user during the vision test or vision training routine from the plurality of images of the head of the user captured by the at least one camera; and
        determine whether or not the user correctly identifies the one or more configurations of the visual object displayed on the output screen of the visual display device;
    wherein the data processing device is further programmed to determine the head velocity or the head speed of the user from the plurality of images of the head of the user captured by the at least one camera by performing the following additional steps:
        extracting features from the plurality of images of the head of the user for providing inputs to a trained neural network;
        determining one or more head poses and/or head movements of the user using the output of the trained neural network; and
        determining the head velocity or the head speed of the user from the one or more head poses and/or head movements of the user.

2. The system according to claim 1, wherein the output of the trained neural network comprises a plurality of keypoints for facial features of the user; and wherein the data processing device is further programmed to determine the one or more head poses and/or head movements of the user from the plurality of keypoints for the facial features of the user.

3. The system according to claim 2, wherein the data processing device is further programmed to estimate a gaze direction of the user using at least some of the plurality of keypoints for the facial features of the user outputted by the trained neural network.

4. The system according to claim 1, further comprising a user input device, the user input device configured to output an input signal in response to a manipulation of the user input device by a system user, the user input device being operatively coupled to the data processing device; and
    wherein the determination of whether or not the user correctly identifies the one or more configurations of the visual object is based upon the input signal from the user input device.

5. The system according to claim 4, wherein the user input device comprises at least one of: (i) a mouse, (ii) a keyboard, (iii) a clicking device, (iv) a selection device with a plurality of buttons corresponding to different configurations of the visual object, (v) a voice recognition device, and (vi) a joystick.

6. The system according to claim 5, wherein the user input device comprises a voice recognition device configured to capture verbal responses of the user regarding the one or more configurations of the visual object that are identified by the user so as to obviate a need for a clinician that records the verbal responses of the user.

7. The system according to claim 1, wherein the visual object displayed on the output screen of the visual display device comprises an optotype, the optotype selected from the group consisting of: (i) a Tumbling E, (ii) a Landolt C, (iii) a house, (iv) a heart, (v) a circle, (vi) a square, (vii) a letter of a recognized alphabet, and (viii) any other identifiable symbol.

* * * * *